US010925939B2

(12) United States Patent
De Groot et al.

(10) Patent No.: US 10,925,939 B2
(45) Date of Patent: *Feb. 23, 2021

(54) REGULATORY T CELL EPITOPES, COMPOSITIONS AND USES THEREOF

(71) Applicant: EpiVax, Inc., Providence, RI (US)

(72) Inventors: Anne De Groot, Providence, RI (US); William Martin, Cumberland, RI (US); Daniel S. Rivera, Marshfield, MA (US)

(73) Assignee: EpiVax, Inc., Providence, RI (US)

( * ) Notice: Subject to any disclaimer, the term of this patent is extended or adjusted under 35 U.S.C. 154(b) by 208 days.

This patent is subject to a terminal disclaimer.

(21) Appl. No.: 16/015,796

(22) Filed: Jun. 22, 2018

(65) Prior Publication Data

US 2018/0289783 A1  Oct. 11, 2018

Related U.S. Application Data

(60) Continuation of application No. 14/857,693, filed on Sep. 17, 2015, now Pat. No. 10,213,496, which is a continuation of application No. 12/981,098, filed on Dec. 29, 2010, now abandoned, which is a division of application No. 12/021,832, filed on Jan. 29, 2008, now Pat. No. 7,884,184.

(60) Provisional application No. 60/898,347, filed on Jan. 30, 2007.

(51) Int. Cl.
| | |
|---|---|
| *A61K 39/00* | (2006.01) |
| *C07K 14/47* | (2006.01) |
| *C07K 14/75* | (2006.01) |
| *C07K 14/76* | (2006.01) |
| *C07K 14/78* | (2006.01) |
| *C07K 14/79* | (2006.01) |
| *A61K 38/00* | (2006.01) |

(52) U.S. Cl.
CPC .......... *A61K 39/0008* (2013.01); *C07K 14/47* (2013.01); *C07K 14/75* (2013.01); *C07K 14/76* (2013.01); *C07K 14/78* (2013.01); *C07K 14/79* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 4,719,107 A | 1/1988 | Carosella et al. | |
| 5,328,470 A | 7/1994 | Nabel et al. | |
| 5,817,308 A | 10/1998 | Scott et al. | |
| 5,854,027 A | 12/1998 | Steipe et al. | |
| 6,090,381 A | 7/2000 | Leung et al. | |
| 6,162,432 A | 12/2000 | Wallner et al. | |
| 6,254,868 B1 | 7/2001 | Leung et al. | |
| 6,838,281 B2 | 1/2005 | Scott et al. | |
| 2002/0193572 A1 | 12/2002 | Leung et al. | |
| 2005/0287632 A1 | 12/2005 | Holmquist et al. | |

FOREIGN PATENT DOCUMENTS

| | | |
|---|---|---|
| EP | 1803732 A2 | 7/2007 |
| EP | 1803732 B1 | 2/2012 |
| WO | 9958572 A1 | 11/1999 |
| WO | 0073481 A1 | 12/2000 |
| WO | 0073841 A1 | 12/2000 |
| WO | 02074783 A2 | 9/2002 |
| WO | 02074783 A3 | 8/2003 |
| WO | 2005063815 A2 | 7/2005 |
| WO | 2006017643 A1 | 2/2006 |
| WO | 2006017647 A1 | 2/2006 |
| WO | 2005063815 A3 | 3/2006 |
| WO | 2006032216 A2 | 3/2006 |
| WO | 2006082406 A2 | 8/2006 |
| WO | 2006083964 A2 | 8/2006 |
| WO | 2006121422 A2 | 11/2006 |
| WO | 2007002223 A2 | 1/2007 |
| WO | 2006082406 A2 | 2/2007 |
| WO | 2006082406 A3 | 2/2007 |
| WO | 2006121422 A3 | 3/2007 |
| WO | 2006121422 A8 | 4/2007 |
| WO | 2007002223 A3 | 4/2007 |
| WO | 2006032216 A3 | 5/2007 |
| WO | 2007076032 A2 | 7/2007 |
| WO | 2007107797 A2 | 9/2007 |
| WO | 2007107797 A3 | 11/2007 |
| WO | 2008021290 A2 | 2/2008 |
| WO | 2007076032 A3 | 4/2008 |
| WO | 2008021290 A8 | 4/2008 |
| WO | 2008021290 A3 | 11/2008 |
| WO | 2008151319 A2 | 3/2009 |
| WO | 2006083964 A3 | 4/2009 |

(Continued)

OTHER PUBLICATIONS

Jager et al.; Identification of tumor antigens as potential target antigens for immunotherapy by serological expression cloning; Jan. 15, 2004; Cancer Immunol Immunother (2004) 53: 144-147; Copyright Springer-Verlag 2004.

Koren et al.; Immune Responses to Therapeutic Proteins in Humans—Clinical Significance, Assessment and Prediction; Current Pharmaceutical Biotechnology, 2002, 3, 349-360; Copyright 2002 Bentham Science Publishers Ltd.

Lane et al.; Hotline Archive—Preliminary FDA Approval of Enbrel (etanercept); Sep. 1998; American College of Rheymatology; www.rheumatology.org/publications/hotline/archive/0998etan.asp.

Lee et al.; Effect of up-front daclizumab when combined with steroids for the treatment of acute graft-versus-host disease: results of a randomized trial; Sep. 1, 2004 vol. 104 No. 5 1559-1564; Copyright 2004; The American Society of Hematology.

Letter regarding Opposition proceedings; Sep. 25, 2014.

(Continued)

*Primary Examiner* — Amy E Juedes
(74) *Attorney, Agent, or Firm* — Dinsmore & Shohl LLP

(57) ABSTRACT

The invention is directed to T cell epitopes wherein said epitopes comprises a peptide or polypeptide chain comprising at least a portion of an immunoglobulin constant or variable region. The invention also relates to methods of using and methods of making the epitopes of the invention.

10 Claims, 23 Drawing Sheets
(2 of 23 Drawing Sheet(s) Filed in Color)

Specification includes a Sequence Listing.

(56) References Cited

FOREIGN PATENT DOCUMENTS

WO    2008021290 A9    4/2009

OTHER PUBLICATIONS

Lonberg; Human antibodies from transgenic animals; Nature Biotechnology; vol. 23, No. 9, Sep. 2005.
Magzoub et al.; Interaction and structure induction of cell-penetrating peptides int he presence of phospholipid vesicles; Biochimica et Biophysica Act 1512 (2001) 77-79; Copyright 2001 Elsevier Science B.V.
Main Request (marked-up); Sep. 29, 2014.
Main Request during Opposition procedure; Apr. 5, 2013.
Main Request during Opposition proceedings; Sep. 25, 2014.
Main Request: Sep. 29, 2014.
Main Request; Sep. 24, 2014.
Main Request; Claims; Aug. 1, 2014.
Main Request; Claims; Aug. 18, 2015.
Merkler; C-Terminal amidated peptides: Production by the in vitro enzymatic amidation of glycine-extended peptides and the important of the amide to bioactivity; Enzyme Microb. Technol.,1994, vol. 16, pp. 450-456; June; Copyright 1994 Butterworth-Heinemann.
Miller et al.; Specific Interaction of Lymphocyte Function-associated Antigen 3 with CD2 Can Inhibit T Cell Responses; J. Exp. Med.; vol. 178, Jul. 1993, 211-222; Copyright The Rockefeller University Press.
Murphy / ipulse; Letter to the European Patent Office—request for extension of time limit; Application No. 08713321.1 ; Nov. 19, 2012.
Murugan et al.; Prediction of MHC class II binding peptides based on an iterative learning model; Published Dec. 13, 2005; Immunome Research 2005; 1:6; Copyright 2005 Murugan and Dai.
Mutis et al.; Definition of a human suppressor T-cell epitope; Proc, Natl. Acad. Sci. USA; vol. 91, pp. 9456-9460, Sep. 1994 Immunology.
Novak et al.; Tetramer-Guided Epitope Mapping: Rapid Identification and Characterization of Immunodominant CD4 + T Cell Epitopes from Complex Antigens; J Immunol 2001;166;6665-6670; Copyright 2001 by The American Association of Immunologists.
Opponent: Advice of delivery; 20104-10-14.
Opponent: Advice of delivery; Jan. 22, 2015.
Opponent: Letter regarding Oral Proceedings; Application No. EP08713321.1; Sep. 29, 2014.
Opponent: Letter relating to Appeal Procedure; Appeal No. T0151/15-3.3.04; May 13, 2016.
Opponent: Notice of Appeal; Jan. 23, 2015.
Opponent; Advice of delivery; Sep. 30, 2014.
Opponent; Advice of delivery; Dec. 2, 2014.
Opponent; Advice of delivery; Application No. 08713321.1; Apr. 17, 2014.
Opponent; Advice of delivery; Application No. 08713321.1; Mar. 10, 2014.
Opponent; Annex to Written submission in preparation for Oral Proceedings; Sep. 17, 2014.
Opponent; Annex(2) to Written submission in preparation for Oral Proceedings; EP-B-2125883; Sep. 17, 2014.
Opponent; Change of all reference numbers for EP cases; Jul. 29, 2014.
Opponent; Letter regarding Opposition; Application No. EP08713321.1; Sep. 24, 2014.
Opponent; Letter regarding the opposition procedure; EP-B-2125883; Aug. 22, 2014.
Opponent; Letter regarding the opposition procedure; EP-B-2125883; Aug. 28, 2014.
Opponent; Letter relating to Appeal Procedure; Jan. 25, 2016.
Opponent; letter relating to Appeal Procedure; Appeal No. T0151.15-3.3.04; Apr. 21, 2017.
Opponent; Letter relating to Appeal Procedure; Appeal No. T0151/15-3.3.04; Dec. 17, 2015.
Opponent; Letter to European Patent Office; request for extension of time limit; Application No. 08713321.1 ; Feb. 1, 2013.
Opponent; Letter to the European Patent Office; Feb. 5, 2013.
Opponent; Request for change of Applicant's representative; Jan. 17, 2014.
Opponent; Request for change of applicant's representative; Jun. 29, 2016.
Opponent; Request for change of applicant's representative; May 9, 2016.
Opponent; Request for Change of Opponent's Representative; Jul. 2, 2015.
Opponent; Request for correction of the publication; Application No. 08713321.1; Apr. 5, 2013.
Opponent; Response to Grounds of Opposition; Reply of the patent proprietor to the notice(s) of opposition; Apr. 5, 2013.
Opponent; Response to the Statement of Grounds of Appeal by Strawman Limited; Aug. 17, 2015.
Opponent; Statement of Grounds of Appeal; In re: Opposition by Strawman Limited against European Patent EP-8-2125883; Mar. 31, 2015.
Opponent; Submissions prior to Oral Proceedings; Application No. 08713321.1; Aug. 1, 2014.
Ahlers, J. et al., "High-affinity T Helper Epitope Induces Complementary Helper and APC Polarization, Increased CTL, and Protection against Viral Infection," J Clin Invest., 2001;108(11)1677-1658.
Basner-Tschakarjan, et al., "Cell-Mediated Immunity to AAV Vectors, Evolving Concepts and Potential Solutions", Front Immunol, 2014; 5: 350, pp. 1-10.
Baxevanis et al., "Evidence for distinct epitopes on human IgG with T cell proliferative and suppressor function," Eur. J. Immunol., 16: 1013-1016, 1986.
Ben-David, H. et al., "A tolerogenic peptide down-regulates mature B cells in bone marrow of lupus-afflicted mice by inhibition of interleukin-7, leading opoptosis", Immunology, Oct. 2009; 128(2); 245-52.
Bischof, F. et al., "Specific treatment of autoimmunity with recombinant invariant chains in which CLIP is replaced by self-epitopes," Proceedings of the National Academy of Sciences of the United States of America, 98: 12168-73, 2001.
Bourdette, et al., "A highly immunogenic trivalent T cell receptor peptide vaccine for multiple sclerosis," Multiple Sclerosis, 2005, vol. 11, pp. 552-561.
Bowie, et al. "Deciphering the Message in Protein Sequences: Tolerance to Amino Acid Substitutions," Science, 247: 1306-1310 (1990).
Bren, Linda, "Alzheimer's: Searching for a Cure," Jul.-Aug. 2003, FDA Consumer Magazine, Pub No. FDA 04-1318C rev, pp. 1-7.
Caspi, "Tregitopes Switch on Tregs," Blood. Oct. 15, 2008; 112(8): 3003-3004.
Chen, et al., "Gene therapy for brain tumors: Regression of experimental gliomas by adenovirus-mediated gene transfer in vivo," Proc. Natl. Acad. Sci. USA; 91: 3054-3057 (1994).
Cobbold et al., "Immune privilege induced by regulatory T cells in transplantation tolerance," Immuological Reviews, 213: 239-255, 2006.
Cousens, et al., "Application of IgG-Derived Natural Treg Epitopes (IgG Tregitopes) to Antigen Specific Tolerance Induction in a Murine Mode of Type 1 Diabetes," J Diabetes Res. 2013: 621693 (17 pages).
Cousens, et al., "In Vitro and in Vivo Studies of IgG-derived Treg Epitopes (Tregitopes): A Promising New Tool for Tolerance Induction and Treatment of Autoimmunity," J. Clin Immunol. Jan. 2013; 33 (Suppl. 1) 43-49.
Cousens, et al., "Teaching tolerance: New approaches to enzyme replacement therapy for Pompe disease", Hum Vaccin Immunother. Oct. 1, 2012; 8(10): 1459-1464.
D'Ambrosio, D. et al., "Cutting Edge: Selective Up-Regulation of Chemokine Receptors CCR4 and CCR8 upon Activation of Polarized Human Type 2 Th Cells," J. Immunol., 161:5111-5, 1998.
De Groot, A. et al., "From genome to vaccine—new immunoinformatics tools for vaccine design," Methods, 34:425-428, 2004.

(56) References Cited

OTHER PUBLICATIONS

De Groot, A. et al., "An Interactive Web Site Providing Major Histocompatibility Ligand Predictions: Application to HIV Research," AIDS Res. Hum Retroviruses, 13:529-531, 1997.
De Groot, A. et al., "From genome to vaccine: in silico predictions, ex vivo verification," Vaccine, 19:4385-95, 2001.
De Groot, A. et al., "Immuno-informatics: Mining genomes for vaccine components", Immunology and Cell Biology, vol. 80, No. 3, Jun. 2002 (Jun. 2002), pp. 255-269.
De Groot, A. et al., "Mapping Cross-Clade HIV-1 Vaccine Epitopes Using a Bioinformatics Approach," Vaccine, 21: 4486-504, 2003.
De Groot, et al., "Beyond humanization and de-immunization: tolerization as a method for reducing the immunogenicity of biologics," Expert Rev Clin Pharmacol. Nov. 2013; 6(6): 651-662.
De Groot, et al., "Tregitope Peptides: The Active Pharmaceutical Ingredient of IVIG?", Clin Dev Immunol. 2013: 398138 (6 pages).
De Groot, et al., "Activation of Natural Regulatory T Cells by IgG Fc-Derived Peptide 'Tregitopes'," Blood, Oct. 15, 2008, vol. 112, pp. 3303-3311.
Decision of Rejection for JP Appl. No. 2011-247226 dated Apr. 2, 2014.
Dumont, et al., "Prolonged activity of a recombinant factor VIII-Fc fusion protein in hemophilia A mice and dogs", Blood, Mar. 29, 2012; 119(13): 3024-3030.
Durinovic-Bello, I. et al., "DRB1*0401-restricted human T cell clone specific for the major proinsulin73-90 epitope expresses a down-regulatory T helper 2 phenotype,"rpoc. Natl. Acad. Sci USA 103: 11683-11688, 2006.
El-Amine, M. et al., "In vivo induction of tolerance by an Ig peptide is not affected by the deletion of FcR or a mutated IgG Fc fragment," Int. Immuonl., 14:761-766, 2002.
El-Amine, M. et al., "Mechanisms of Tolerance Induction by a Gene-Transferred Peptide-IgG Fusion Protein Expressed in B Lineage Cells," J. Immunol., 165:5631-5636, 2000.
Elyaman, et al., "Potential Application of Tregitopes as Immunomodulating Agents in Multiple Sclerosis," Neurol Res Int. 2011; 2011:256460 (6 pages).
Examination Report for EP Appl. No. 11 177 609.2 dated May 10, 2013.
Examination Report for EP Appl. No. 11 177 625.8 dated May 10, 2013.
Examination Report for EP Appl. No. 11 177 630.8 dated May 10, 2013.
Examination Report for EP Appl. No. 11 177 634.0 dated May 10, 2013.
Examination Report for EP Appl. No. 12 153 164.4 dated Dec. 18, 2012.
Examination Report for EP Appl. No. 12 153 164.4 dated May 10, 2013.
Examination Report for EP Appl. No. 12 153 164.4 dated Oct. 18, 2013.
Examination Report for EP Appl. No. 12 153166.9 dated May 10, 2013.
Examination Report for EP Appl. No. 12 153 170.1 dated May 10, 2013.
Examination Report for EP Appl. No. 12 153 171.9 dated May 10, 2013.
Examination Report for EP Appl. No. 12 153 173.5 dated May 10, 2013.
Examination Report for EP Appl. No. 12 153174.3 dated May 10, 2013.
Examination Report for EP Appl. No. 12 153 177.6 dated May 10, 2013.
Extended European Search Report for EP 11177609.2 (077545-0240) dated Jan. 31, 2012.
Extended European Search Report for EP 11177625.8 (077545-0241) dated Jan. 31, 2012.
Extended European Search Report for EP 11177630.8 (077545-0242) dated Jan. 31, 2012.
Extended European Search Report for EP 11177634.0 (077545-0243) dated Jan. 31, 2012.
Extended European Search Report for EP 12153164.4 (077545-0245) dated Mar. 23, 2012.
Extended European Search Report for EP 12153166.9 (077545-0246) dated Mar. 14, 2012.
Extended European Search Report for EP 12153170.1 (077545-0247) dated Mar. 14, 2012.
Office Action for CA Appl. No. 2,677,073 dated Oct. 20, 2014.
Office Action for CA Application No. 2,677,073 dated Mar. 31, 2014.
Office Action for Chinese Patent Application No. 200880011016.5 dated Aug. 31, 2011.
Office Action for Chinese Patent Application No. 201310685046.7 dated Feb. 14, 2016.
Office Action for European Appl. No. 08 713 321.1 dated Feb. 1, 2010.
Office Action for Israeli Appl. No. 200129 dated Aug. 26, 2014.
Office Action for Israeli Appl. No. 200129 dated Jul. 17, 2011.
Office Action for Israeli Application No. 200129 dated Mar. 20, 2013.
Office Action for Israeli Application No. 200129 dated Nov. 29, 2015.
Office Action for JP Application No. 2011-247226 dated Jan. 30, 2013.
Office Action for KR Appl. No. 10-2009-7017996 dated Jan. 7, 2015.
Office Action for KR Appl. No. 10-2009-7017996 dated May 29, 2015.
Office Action for KR Appl. No. 10-2014-7024226 dated Nov. 25, 2014.
Office Action for KR Application No. 10-2009-7017996 dated May 29, 2014.
Office Action for KR Patent Application No. 10-2014-7024226 dated Feb. 5, 2016.
Office Action for MX Appl. No. MX/a/2009/008230 dated Mar. 19, 2013.
Office Action for MX Appl. No. MX/a/2009/008230 dated Nov. 13, 2013.
Office Action for MX Appl. No. MX/a/2009/008230 dated Sep. 27, 2012.
Office Action for MX Appl. No. MX/a/2013/002666 dated Dec. 10, 2014.
Office Action for MX Appl. No. MX/a/2013/008779 dated Apr. 9, 2015.
Office Action for MX Appl. No. MX/a/2013/008780 dated Apr. 10, 2015.
Office Action for MX Appl. No. MX/a/2013/008781 dated Apr. 10, 2015.
Offner, et al., "T Cell Receptor Peptide Therapy Triggers Autoregulation of Experimental Encephalmyelitis," Science, 1991, vol. 251, pp. 430-432.
Parsons, T. et al., "A novel CEA vaccine stimulates T cell proliferation, gammaiFN secretion and CEA specific CTL responses," Vaccine, (Sep. 3, 2004) vol. 22, No. 25-26 pp. 3487-3494.
Phillips, W. et al., "Recombinant Immunoglobulin-Based Epitope Delivery: A Novel Class of Autoimmune Regulators," Int. Rev. Immunol., 24: 501-17, 2005.
Ramakrishna, et al., "Passively Administered Pooled Human Immunoglobulins Exert IL-10 Dependent Anti-Inflammatory Effects that Protect against Fatal HSV Encephalitis", PLOS Pathog, Jun. 2011; 7(6): e1002071 (17 pages).
Ravetch, J. et al., "Structural Heterogeneity and Functional Domains of Murine Immunoglobulin G Fc Receptors," Science 234 4777 (1986): 718-725.
Reijonen, H. et al., "Use of HLA class II tetramers in tracking antigen-specific T cells and mapping T-cell epitopes," Methods, 29:282-288, 2003.
Reitan, S. et al., "Immunoglobulin heavy chain constant regions regulate immunity and tolerance to idiotypes of antibody variable regions," Proc. Natl. Acad. Sci. USA, vol. 99, No. 11, 7588-7593, 2002.

(56) References Cited

OTHER PUBLICATIONS

Restriction Requirement for U.S. Appl. No. 12/021,832 dated Oct. 16, 2009.
Ruitenberg, J. et al., "VACUTAINER® CPT™ and Ficoll density gradient separation perform equivalently in maintaining the quality and function of PBMC from HIV seropositive blood samples," BMC Immunol., 7:11, 2006.
Sander Van Der Marel, et al., "Adena-associated virus mediated delivery of Tregitope 167 ameliorates experimental colitis", World J Gastroenterol, Aug. 28, 2012; 18 (32): 4288-4299.
Schafer, J. et al., "Prediction of well-conserved HIV-1 ligands using a matrix-based algorithm, EpiMatrix," Vaccine, vol. 16, No. 19, 1880-1884, 1998.
Scott et al., "Progress toward inducing immunologic tolerance to factor VIII," Blood, May 30, 2013; 121(22) 4449-4456.
Second Office Action for CN Application No. 200880011016.5 dated Aug. 3, 2012.
Second Office Action for CN Application No. 201310685046.7 dated Sep. 17, 2015.
Seeliger, Daniel, "Development of Scoring Functions for Antibody Sequence Assessment and Optimization", PLOS One, 2013, 8(10): e76909 (8 pages).
Sela, et al., "A Peptide that Ameliorates Lupus Up-Regulates the Diminished Expression of Early Growth Response Factors 2 and 3," J. Immunol. Feb. 1, 2008; 180(3): 1584-91.
Sela, U. et al., "Down-Regulation of Stromal Cell-Derived Factor-1a-Induced T Cell Chemotaxis by a Peptide Based on the Complementarity-Determining Region 1 of an Anti-DNA Autoantibody via Up-Regulation of TGF-β Secretion1," The Journal of Immunology, 2005, vol. 174 pp. 302-309.
Sela, U. et al., "The Inhibition of Autoreactive T Cell Functions by a Peptide Based on the CDR1 of an Anti-DNA Autoantibody Is via TGF-β-Mediated Suppression of LFA-1 and CD44 Expression and Function1 ,"The Journal of Immunology, 2005, vol. 175, pp. 7255-7263.
Self, et al., "Divergent contributions of regulatory T cells to the pathogenesis of chronic hepatitis C", Hum Vaccin Immunother, Jul. 1, 2013; 9(7): 1569-1576.
Sharabi A, et al., "Bcl-xL is required for the development of functional regulatory CD4 cells in lupus-afflicted mice following treatment with a tolerogenic peptide", J. Autoimmun. Mar. 2010; 34(2): 87-95.
Sharabi A., et al., "Harnessing regulatory T cells for the therapy of lupus and other autoimmune diseases," Immunotherapy, May 2009; 1 (3): 385-401.
Shevach, E. et al., "The lifestyle of naturally occurring CD4+CD25+ Foxp3+ regulatory T cells," Immunol. Rev., 212:60-73, 2006.
Shevach, E., "CD4+CD25+ Suppressor T Cells: More Questions Than Answers," Nat. Rev. Immunol., 2:389-400, 2002.
Shioji, K. et al., "Fe Receptor-Mediated Inhibitory Effect of Immunoglobulin Therapy on Autoimmune Giant Cell Myocarditis: Concomitant Suppression of the Expression of Dendritic Cells," Circ. Res., 89:540-546, 2001.
Southwood, S. et al., "Several Common HLA-DR Types Share Largely Overlapping Peptide Binding Repertoires," J. Immunol., 160:3363-3373, 1998.
St. Clair, E. et al., "New Reagents on the Horizon for Immune Tolerance," Annu. Rev. Med., 58:329-346, 2007.
Sthoeger, Z.M. et al., "Treatment of lupus patients with a tolerogenic peptide, hCDR1 (Edratide): Immunomodulation of gene expression," J. Autoimmun., Aug. 2009: 33(1):77-82.
Stock, P. et al., "Inhibition of the Allergic Response by Regulatory T Cells," Curr. Opin. Allergy Clin. Immunol., 6:12-16, 2006.
Extended European Search Report for EP 12153171.9 (077545-0248) dated Mar. 14, 2012.
Extended European Search Report for EP 12153173.5 (077545-0249) dated Mar. 14, 2012.
Extended European Search Report for EP 12153174.3 (077545-0250) dated Mar. 14, 2012.
Extended European Search Report for EP 15153177.6 (077545-0251) dated Mar. 14, 2012.
Extended European Search Report for EP 15153373.4 (077545-0262) dated Jun. 17, 2015.
Eyerman, M. et al., "T Cell Recognition and Tolerance of Antibody Diversity," The Journal of Immunology, 1996, vol. 157, pp. 1037-1046.
Feng, 1., et al., "HBcAg-specific CD4+CD25+regulatory T cells modulate immune tolerance and acute exacerbation on the natural history of chronic hepatitis B virus infection," J. Biomed Sc., 14:43-57, 2007.
First Examination Report for AU Application No. 2008211227 dated Jun. 28, 2012.
First Examination Report for AU Application No. 2014201846 dated Jun. 23, 2015.
First Office Action for Chinese Appl. No. 201310685046.7 dated Feb. 28, 2015.
Grant et al., "Testing Agents for Prevention or Reversal of Type 1 Diabetes in Rodents", PLOS One. 2013; 8(8): e72989 (14 pages).
Guo, W. et al., "T Cell Tolerance to Germline-Encoded Antibody Sequences in a Lupus-Prone Mouse," The Journal of Immunology, 2005, vol. 175, pp. 2184-2190.
Hahn, B. et al., "Tolerogenic Treatment of Lupus Mice with Consensus Peptide Induces Foxp3-Expressing Apoptosis-Resistant, TCF-Secreting CD8+ T Cell Suppressors1," The Journal of Immunology, 2005, vol. 175, pp. 1728-7737.
Hahn, B. et al., "Treatment With a Consensus Peptide Based on Amino Acid Sequences in Autoantibodies Prevents T Cell Activation by Autoantigens and Delays Disease Onset in Murine Lupus," Arthritis & Rheumatism, vol. 44, No. 2, pp. 432-441 (2001).
Hall, et al., "Interleukin-10-Mediated Regulatory T-Cell Responses to Epitopes on a Human Red Blood Cell Autoantigens", Blood, Dec. 15, 2002, vol. 100, No. 13, pp. 4529-4536.
Hjelm, F. et al., "Antibody-Mediated Regulation of the Immune Response," Scand. J. Immunol., 64: 177-184, 2006.
Hochweller, K. et al., "Immunological Tolerance Using Synthetic Peptides—Basic Mechanisms and Clinical Application," Curr. Mol. Med, 6:631-43, 2006.
Huang, X. et al., "Protection against Autoimmunity in Nonlymphopenic Hosts by CD4+CD25+ Regulatory T Cells is Antigen-Specific Requires IL-10 and TGF-1," J. Immunol., 175: 4283-4291 2005.
Hudgens, M. et ai.,"Statistical considerations for the design and analysis of the ELISpot assay in HIV-1 vaccine trials", J. Immunol. Methods, 288: 19-34, 2004.
Hui et al., "Modulation of CD8+T cell responses to AAV vectors with IgG-derived MHC class II epitopes," Mol Ther. Sep. 2013; 21(9): 1727-1737.
Igawa, et al., "Engineering the variable region of therapeutic IgG antibodies," MAbs. May-Jun. 2011; 3(3): 243-252.
Intent to Grant for EP Appl. No. 08 713 321.1 dated Apr. 5, 2011.
International Preliminary Report on Patentability for PCT/US2008/001148 dated Aug. 4, 2009.
Ivanyi, "Function and Potentials of M. tuberculosis Epitopes", Front Immunol. 2014; 5: 107 (11 pages).
Jordan, S. et al., "Intravenous Gammaglobulin (IVIG): A Novel Approach to Improve Transplant Rates and Outcomes in Highly HLA-Sensitized Patients," American Journal of Transplantation, 6: 459-466, 2006.
Joshi, T. et al., "Molecular analysis of expression and function of hFcγRIIbI and b2 isoforms in myeloid cells," Molecular Immunology,43:839-850, 2006.
Journal of the Japanese Society for Food Science and Technology [in Japanese], 53[7] (2006) p. 399.
Kalsi, J. et al., "Peptides from Antibodies to DNA Elicit Cytokine Release from Peripheral Blood Mononuclear Cells of Patients with Systemic Lupus Erythematosus: Relation of Cytokine Pattern to Disease Duration," Lupus, 2004, vol. 13, pp. 490-500.
Kamphuis, et al., "Tolerogenic immune responses to novel T-cell epitopes from heat-shock protein 60 in juvenile idiopathic arthritis", Lancet, Jul. 2005, vol. 366, pp. 50-56.
Karlsson, et al., "Efficient IgG-mediated suppression of primary antibody responses in Fcgamma receptor-devicent mice", Proc. Natl. Acad. Sci., vol. 96, Mar. 2, 1999, pp. 2244-2249.

(56) References Cited

OTHER PUBLICATIONS

Kieber-Emmons, et al., "The promise of the anti-idiotype concept", Front Oncol. 2012; 2: 196 (12 pages).
Klee, L., et al., "Probable Epitopes Relationships Between Myelin Basic Protein Antigenic Determinants and Viral Bacterial Proteins," Neuroinformatics, 2:59-70, 2004.
La Cava, et al., "Ig-Reactive CD4+ CD25+ T Cells from Tolerized (New Zealand Black X New Zealand White)F1 Mice Suppress in Vitro Production of Antibodies to DNA1," The Journal of Immunology, 2004, vol. 173, pp. 3542-3548.
Lanza, et al., "Enhancement of Regulatory T Cells (Treg) Function by Epitope Specific Immunotherapy Leads to Clinical Control of Experimental Autoimmune Encephalomyelitis (EAE)", J. of Immunology, 2006, vol. 176, pp. S150, abstract.
Lei, et al., "Tolerance induction via a B-cell delivered gene therapy-based protocol: Optimization and role of the Ig scaffold," Cell. Immunol. 235:12-20, 2005.
Li, et al., "Defining Target Antigens for CD25(+)FOXP3(+)1FN-gamma(-) Regulatory T Cells in Chronic Hepatitis C Virus Infection", Immunology and Cell Biology, Jan. 2, 2007, vol. 85, pp. 197-204.
MacDonald, et al., "CD4 T Helper Type 1 and Regulatory T Cells Induced Against the Same Epitopes on the Core Protein in Hepatitis C Virus-Infected Persons", Journal of Infectious Diseases, Mar. 15, 2002, vol. 185, pp. 720-727.
Mishra, S. et al., "Dendritic Cell-Mediated, DNA-Based Vaccination against Hepatitis C Induces the Multi-Epitope-Specific Response of Humanized, HLA Transgenic Mice", PLOS One. 2014; 9(8): e104606 (8 pages).
Moise, et al., "The two-faced T cell epitope: Examining the host-microbe interface with JanusMatrix", Hum Vaccin Immunother. Jul. 1, 2013; 9(7):1577-1586.
Monneaux, F. et al., "Selective Modulation of CD4+ T Cells from Lupus Patients by a Promiscuous, Protective Peptide Analog," J. Immunol., 175:5839-5847.
Mudd, P. et al., "Regulatory T Cells and Systemic Lupus Erythematosus," Scandinavian Journal of Immunology, 64: 211-218, 2006.
Nagata, K. et al., "Selective Expression of a Novel Surface Molecule by Human Th2 Cells In Vivo," J. Immunol., 162:1278-86, 1999.
Ng, et al., "A vaccine directed to B cells and produced by cell-free protein synthesis generates potent antilymphoma immunity", Proc Natl Acad Sci USA Sep. 4, 2012; 109(36): 14526-141.
Nguyen, V. et al., "Role of Naturally Arising Regulatory T Cells in Hematopoietic Cell Transplantation," Biol. Blood Marrow Transplant, 12:995-1009, 2006.
Non-Final Office Action for U.S. Appl. No. 12/021,832 dated Feb. 24, 2010.
Non-Final Office Action for U.S. Appl. No. 12/981,098 dated Aug. 13, 2014.
Notice of Reasons for Rejection for JP Appl. No. 2009-548278 dated Jun. 22, 2011.
Notice of Reasons for Rejection for JP Appl. No. 2014-154372 dated Oct. 14, 2015.
Novak, E. et al., "Tetramer-Guided Epitope Mapping: Rapid Identification and Characterization of Immunodominant CD4+ T Cell Epitopes from Complex Antigens1," J. Immunol. 166:6665-6670, 2001.
Sturniolo, T. et al., "Generation of tissue-specific and promiscuous HLA ligand databases using DNA microarrays and virtual HLA class II matrices," Nat. Biotechnol., 17:555-561, 1999.
Su, et al., "B-Cell Gene Therapy for Tolerance Induction: Host but Not Donor B-Cell Derived IL-10 is Necessary for Tolerance", Front Microbiol., 2011; 2: 154 (7 pages).
Su, et al., Regulatory T cell epitopes (Tregitopes) in IgG induce tolerance in vivo and lack immunogenicity per se,: J. Leukoc Biol., Aug. 2013; 94(2): 377-383.
Sumida, T. et al., Regulatory T cell epitope recognized by T cells from labial salivary glands of patients with Sjögren's syndrome, Arthritis & Rheumatism, 40:12, 2271-2274, 1974.

Tang, Q. et al., "Regulatory T-cell physiology and application to treat autoimmunity," Immunological Reviews, 212: 217-237, 2006.
Third Office Action for Chinese Appl. No. 200880011016.5 dated Feb. 17, 2013.
Vandenbark, "TCR Peptide Vaccination in Multiple Sclerosis: Boosting a Deficient Natural Regulatory Network that may involve TCR-Specific CD4+CD25+ Treg Cells," Current Drug Targets—Inflammation & Allergy, 2005, vol. 4, pp. 217-229.
Vandenbark, et al., "Effects of vaccination with T cell receptor peptides: Epitope switching to a possible disease-protective determinant of myelin basic protein that is cross-reactive with a TCR BV peptide," Immunology and Cell Biology, 1998, vol. 76, pp. 83-90.
Vandenbark, et al., "TCR Peptide Therapy in Human Autoimmune Diseases," Neurochemical Research 2001, vol. 26, No. 6, pp. 713-730.
Warncke, et al., "Control of the specificity ofT cell-mediated anti-idiotype immunity by natural regulatory T Cells," Cancer Immunol Immunother, Jan. 2011; 60(1): 49-60.
Weber, et al., "P19-43. Regulatory T cell epitopes in a dendritic cell-targeted HIV vaccine delivery platform", Retrovirology, 2009; 6(Suppl 3): P363.
Wing, K. et al., "Regulatory T cells as potential immunotherapy in allergy," Curr. Opin. Allergy Clin. Immunol. 6:482-488, 2006.
Wohlleben, G. et al., "Immune Stimulatory Strategies for the Prevention and Treatment of Asthma," Curr. Pharm Des., 12:3281-92, 2006.
Zambidis, E. et al., "Epitope-specific Tolerance Induction with an Engineered Immunoglobulin," Proc. Natl. Acad. Sci. USA 93:5019-5024, 1996.
Zhang, et al., "A Receptor Presentation Hypothesis forT Cell Help That Recruits Autoreactive B Cells," The Journal of Immunology, 2001, vol. 166, pp. 1562-1571.
Examination Report for AU 2016203577 dated Dec. 19, 2016.
Examination Report for AU 2014201846 dated May 4, 2016.
Examination Report for EP15153373.4 dated Aug. 4, 2016.
Examination Report for IL 245478 dated Dec. 21, 2016, English Translation.
GenBank Accession No. CAA43356 Nov. 17, 2004.
Notice of Reasons of Rejection for JP2014-154372 dated Jul. 6, 2016.
Office Action for CA 2915168 dated Mar. 11, 2016.
Office Action issued for MX/a/2015/014429 dated Aug. 23, 2016.
Notice of Allowance U.S. Appl. No. 14/857,693 dated Oct. 22, 2018.
Notice of Acceptance Australian Application No. 2017268600A1 dated Oct. 4, 2018.
Decision to Grant Japanese Application No. 201706429 dated Dec. 25, 2018.
Examination Report pertaining to corresponding Australian Patent Application No. 2019200571, dated Oct. 8, 2019.
Election Restriction dated Nov. 27, 2019, for U.S. Appl. No. 16/015,828, filed Jun. 22, 2018.
Election Restriction dated Nov. 27, 2019, for U.S. Appl. No. 16/015,837, filed Jun. 22, 2018.
Election Restriction dated Dec. 11, 2019, for U.S. Appl. No. 16/161,671, filed Oct. 16, 2018.
Opponent: Opposition to: EP-B-2125883 Entitled: "Regulatory T Cell Epitopes, Compositions and Uses Thereof"; Epivax, Inc; Jun. 20, 2012.
Opponent; Written submission in preparation for Oral Proceedings; EP-B-2125883; Sep. 17, 2014.
Petersen; Effectiveness of intravenous gammaglobulin preparations; comparison between Sandoglobulin and gamma-Venin in the prevention of rubella infections; http://www.mendeley.com/research/effectiveness-of-intravenous-gammaglobulin-pre . . . ; Deutsche medizinische Wochenschrift 1946(1962) vol. 107, Issue; 49, pp. 1878-1881.
Ramos-Casals et al., Rituximab in systemic lupus erythematosusA systematic review of off-label use in 188 cases, Lupus, Aug. 2009, p. 1 of 1, vol. 18 No. 9 767-776, Sage Journals.
Reply Submissions In re: Opposition to: EP-B-2125883 Entitled: "Regulatory T-cell Epitopes, Compositions and Uses Thereof."

(56) References Cited

OTHER PUBLICATIONS

Results of Analysis of Human IgG1 C Region Using D75 Algorithm; May 13, 2016.
Rituxan Injection for Intravenous Use Final Labeling Test, 1997, p. 1-35.
Roche Pharmaceuticals; Zenapax (daclizumab) Sterile Concentrate for Injection; 3609650 USA 27899043; Sep. 2005; Copyright 1999-2005 by Hoffmann-La Roche Inc.
Roncarolo et al.; The validity of Foxp3 to define human and mouse regulatory T cells; Eur. J. Immunol. 2008. 38: 901-937; Copyright 2008 Wiley-VCH Verlag GmbH & Co KGaA, Weinheim.
Rutgeerts et al.; Review article: infliximab therapy for inflammatory bowel disease—seven years on; Copyright 2006 The Authors, Aliment Pharmacol Ther 23, 451-463; Journal compilation Copyright 2006 Blackwell Publishing Ltd.
Sailler L., Rituximab off label use for difficult-to-treat auto-immune diseases: reappraisal of benefits and risks., Clin Rev Allergy Immunol, Feb. 2008, p. 1 of 1, Service de Pharmacologie Clinique, Unite de Pharmacoepidemiologie, CHU de Toulouse, IFR INSERM 126, EA 3696, Toulouse, France.
Sakaguchi et al.; Regulatory T cells—a brief history and perspective; Eur. J. Immunol. 2007. 37: S116-1; 2007 Wiley-VCH Verlag GmbH & Co. KGaA, Weinheim.
Sakaguchi et al.; Regulatory T cells—a brief history and perspective; Eur. J. Immunol. 2007. 37: S116-12; Copyright 2007 Wiley-VCH Verlag GmbH & Co., KGaA, Weinheim.
Sakaguchi et al.; Regulatory T cells—a brief history and perspective; Eur. J. Immunol. 2007. 37: S116-123; Copyright 2007 Wiley-VCH Verlag GmbH & Co. KGaA, Weinheim.
Scandella et al.; Epitope mapping of hman factor VIII inhibitor antibodies by deletion analysis of factor VIII fragments expresssed in *Escherichia coli;* Proc. Natl. Acad. Sci. USA; vol. 85, pp. 6152-6156, Aug. 1988, Medical Sciences.
Scheinfeld MD JD; Adalimumab (Humira): A Review; JDD 2; 4; Aug. 2003: J Drugs Dermatol 2003; 2; 4; 375-377; Copyright 2003, Journal of Drugs in Dermatology.
Shevach; CD4+CD25+ Suppressor T cells; More Questions than Answers; Nature Reviews | Immunology; vol. 2; Jun. 2002; 389-400.
Shevach; The Resurrection of T Cell-Mediated Suppression; J. Immunol 2011; 186:3805-3807.
Siegel; Department of Health & Human Services: Letter to Mr. Martin Page; Aug. 24, 1998.
Siegel; Department of Health & Human Services; Letter to Ms. da Silva; Dec. 10, 1997.
Singh et al.; ProPred: prediction of HLA-DR binding sites; Bioinformatics Applications Note vol. 17 No. 12 2001; pp. 1236-1237; Copyright University Press 2001.
Sioud; Target Discovery and Validation Reviews and Protocols; Copyright 2007 Humana Press Inc.
Teles et al.; Regulatory T Cells are Baby's Best Friends; American Journal of Reproductive Immunology 69 (2013) 331-339; Copyright 2013 John Wiley & Sons A/S.
Traub: Failure of a Commercial, Intravenously Applicable IgG F(ab)2 Preparation (Bamma-Venin(r)) to Enhance Human Serum Bactericidal Activity Against Serratia marcescens; Z bl. Bakt. Hyg., I. Abt. Orig. A 249, 504-511 (1981).
Walker et al.; Mapping major and minor T-cell epitopes in vitro and their immunogenic or tolerogenic effect in vivo in non-human primates; Immunology 1993 80 209-216.
Wang et al.; CD8 regulatory T cells; What's old is now new; Immunology and Cell Biology (2009) 87, 192-193; Feb. 24, 2009; Copyright 2009 Australasian Society for Immunology Inc.
Weinblatt et al.; Adalimumab, a Fully Human Anti-Tumor Necrosis Factor α Monoclonal Antibody, for the Treatment of Rheumatoid Arthritis in Patients Taking Concomitant Methotrexate; The ARMADA Trial; Arthritis & Rheumatism; vol. 48, No. 1, Jan. 2003, pp. 35-45; DOI 10.1002/ART.10697; Copyright 2003, American College of Rheumatology.
Xuan et al.; In Vitro Reduction of Endotoxin Concentrations with the 5S Fragment of Immunoglobulin G; Antimicrobial Agents and Chemotherapy, Jul. 1997, p. 1512-1516, vol. 41, No. 7; Copyright 1997, American Society for Microbiology.
EPO; Interlocutory decision in Opposition proceedings (Art. 101(3)(a)and 106(2) EPC); Nov. 25, 2014.
EPO; Letter accompanying subsequently filed items; Jan. 23, 2015.
EPO; Letter accompanying subsequently filed items; Application No. 08713321.1; May 13, 2015.
EPO; Minutes of the oral proceedings—conclusion of the proceedings (2); Nov. 25, 2014.
EPO; Minutes of the oral proceedings—conclusion of the proceedings: Nov. 25, 2014.
EPO: Minutes of the oral proceedings before the Opposition Division; 20104-11-25.
EPO; Opposition addresses(2); 2014-11-25-23XX.
EPO; Opposition addresses; Nov. 25, 2014.
EPO; Provision of the minutes in accordance with Rule 124(4) EPC; Nov. 25, 2014.
EPO; Acknowledgement of receipt—Opposition proceedings in relation to EP08713321.1; Submission No. 3020488; Sep. 24, 2014.
EPO; Acknowledgement of receipt—Opposition proceedings in relation to EP08713321.1; Aug. 1, 2014.
EPO; Acknowledgement of receipt—Opposition proceedings in relation to EP08713321.1; Aug. 28, 2014.
EPO; Acknowledgement of receipt—Opposition proceedings in relation to EP08713321.1; Sep. 29, 2014.
EPO; Acknowledgement of receipt—Opposition proceedings in relation to EP08713321.1; Submission No. 2958110; Aug. 22, 2014.
EPO; Acknowledgement of receipt—Opposition proceedings in relation to EP08713321.1; Submission No. 3006754; Sep. 17, 2014.
EPO; Acknowledgement of receipt—Opposition proceedings in relation to EP08713321.1; Submission No. 3029640; Sep. 29, 2014.
EPO; Acknowledgement of receipt of a document; Application No. 08713321.1; Mar. 3, 2014.
EPO; Acknowledgement of receipt of document (2); Mar. 3, 2014.
EPO; Acknowledgement of receipt of document (2); Nov. 25, 2014.
EPO; Acknowledgement of receipt of document; Nov. 25, 2014.
EPO; Acknowledgement of receipt of Notice of Opposition; Submission No. 1697907; Application No. EP08713321.1; Patent No. EP2125883; Jun. 20, 2012.
EPO; Acknowledgement of receipt Opposition proceedings in relation to EP08713321.1; Submission No. 2275995; Aug. 28, 2013.
EPO; Acknowledgement of receipt; Application No. 08713321.1; Submission No. 2074735; Apr. 5, 2013.
EPO; Acknowledgement of receipt; Application No. EP08713321.1; Submission No. 3408579; Mar. 31, 2015.
EPO; Acknowledgement of receipt; Application No. EP08713321.1; Submission No. 3991506; Dec. 17, 2015.
EPO; Acknowledgement of receipt; Application No. EP08713321.1; Submission No. 4339517; May 13, 2016.
EPO; Acknowledgement of receipt; Application No. EP08713321.1; Submission No. 5218847; Apr. 21, 2017.
EPO; Acknowledgement of receipt; Applicaton No. EP08713321.1; Submission No. 3707811; Aug. 18, 2015.
EPO; Acknowledgement of receipt; Submission No. 1988409; Application No. 08713321.1; Feb. 1, 2013.
EPO; Acknowledgement of receipt; Submission No. 1991192; Application No. 08713321.1; Feb. 5, 2013.
EPO; Acknowledgement of receipt; Submission No. 2915247; Application No. 08713321.1; Jul. 30, 2014.
EPO; Acknowledgement of Receipt; Submission No. 1888832; Application No. 08713321.1-2115 / 2125883; Nov. 19, 2012.
EPO; Annex to the communication—opposition; Application No. 08713321.1; Mar. 3, 2014.
EPO; Boards of Appeal; Appeal No. T0151/15-3.3.04; Communication of amended entries in the Register of European patents; Jul. 17, 2015.
EPO; Boards of Appeal; Appeal No. T0151/15-3.3.04; Communication of the Registry; Aug. 21, 2015.
EPO; Boards of Appeal; Appeal No. T0151/15-3.3.04; forwarding of submissions to parties; May 20, 2016.

(56) References Cited

OTHER PUBLICATIONS

EPO; Boards of Appeal; Order: Composition of the Board; Appeal No. T0151/15-3.3.04; Jul. 21, 2015.
EPO; Brief Communication—Opposition proceedings (2); Application No. 08713321.1; Aug. 8, 2014.
EPO; Brief Communication—Opposition proceedings; Aug. 5, 2014.
EPO; Brief Communication—Opposition proceedings; Sep. 29, 2014.
EPO; Brief Communication—Opposition proceedings; Oct. 2, 2014.
EPO; Brief Communication—Opposition proceedings; Oct. 6, 2014.
EPO; Brief Communication—Opposition proceedings; Sep. 30, 2014.
EPO; Brief Communication—Opposition proceedings; Application No. 08713321.1; Sep. 2, 2013.
EPO; Brief Communication—Opposition proceedings; Application No. 08713321.1; Sep. 3, 2014.
EPO; Brief Communication—Opposition proceedings; Application No. 08713321.1; Feb. 4, 2014.
EPO; Brief Communication—Opposition proceedings; Application No. 08713321.1; Feb. 7, 2013.
EPO; Brief Communication—Opposition proceedings; Application No. 08713321.1; Aug. 27, 2014.
EPO; Brief Communication—Opposition proceedings; Application No. 08713321.1; Sep. 23, 2014.
Advice of Delivery; Sep. 25, 2014.
Allen et al.; Enhanced immunogenicity of a T cell immunogenic peptide by modifications of its N and C termini; International Immunology, vol. 1, No. 2; Copyright 1989 The Japanese Society for Immunology 0953 8178/89.
Annex 1—Full List of Citations; Nov. 15, 2014.
Annex 1; Claims as Granted; Jun. 20, 2012.
Annex 2—Main Request; Nov. 25, 2014.
Annex 3—Amended Pages; EP 2125883B1; Nov. 25, 2014.
Auxilary Request I; Sep. 24, 2014.
Auxilary Request I; Sep. 25, 2014.
Auxilary Request I; Claims. Aug. 1, 2014.
Auxilary Request II; Claims; Aug. 1, 2014.
Auxilary Request III; Claims; Aug. 1, 2014.
Auxilary Request IV; Claims; Aug. 1, 2014.
Auxiliary Request I (marked-up)—Sep. 29, 2014.
Auxiliary Request I; Sep. 29, 2014.
Auxiliary Request I; amended claims with annotations; Aug. 18, 2015.
Auxiliary Request I; claims; Aug. 18, 2015.
Auxiliary Request II (Marked up); Sep. 29, 2014.
Auxiliary Request II; Sep. 29, 2014.
Auxiliary Request II; amended claims with annotations; Aug. 18, 2015.
Auxiliary Request II; claims; Aug. 18, 2015.
Baecher-Allan et al.; Functional analysis of highly defined. FACS-isolated populations of human regulatory CD4+CD25+ T cells; Clinical Immunology 115 (2005) 10-18.
Baxevanis et al.; Evidence for distinct eptiopes on human IgG with T cell proliferative and suppressor function; Eur. J. Immunol. 1986.16: 1013-1016; copyright VCH Berlagsgeseelschaft mbH, D-6940 Weinheim, 1986.
Biogen IDEC Canada Inc., Product Monograph ; AMEVIVE (alefacept) Lyophilized power for reconstitution ; 15mg/0.5mL reconstituted solution for intramuscular injection ; Therapeutic Classification Selective immunomodulating antipsoriatic agent; Action and Clinical Pharmacology , Oct. 6, 2004, p. 1-40.
Bolhassani et al.; Improvement different vaccine delivery systems for cancer therapy; Bolhassani et al. Molecular Cancer 2011. 10:3.
Brief Communication—Opposition proceedings (2); Sep. 30, 2014.
Carson et al.; T Cell Receptor Recognition of MHC Class II-Bound Peptide Flanking Residues Enhances Immunogenicity and Results in Altered TCR V Region Usage; Immunity, vol. 7, 387-399, Sep. 1997, Copyright 1997 by Cell Press.
Cole et al.; Modification of the carboxy-terminal flanking region of a universal influenza epitope alters CD4+ T-cell repertoire selection;
Nature Communications | DO1: 10.1038/ncomms1665; Copyright 2012 Macmillan Publishers Limited.
Cottingham et al.; A method for the amidation of recombinant peptides expressed as intein fusioin proteins in *Escherichia coli;* nature biotechnology; vol. 19; Oct. 2001; http://biotech.nature.com; pp. 974-977.
Cousens et al.; In Vitro and In Vivo Studies of IgG-derviced Treg Epitopes (Tregitopes): A Promising New Tool for Tolerance Induction and Treatment of Autoimmunity; J Clin Immunol (2013) 33 (Suppl 1):S43-S49.
Cousens et al.; Tregitope update: Mechanism of action parallels IVIg; Autoimmunity Reviews 12 (2013) 436-443.
De Groot et al., Immunogenicity of protein therapeutics. TRENDS in Immunology, p. 482-490, vol. 28 No. 11, Elsevier.
De Groot et al.; Activation of natural regulatory T cells by IgG Fc-derived peptide "Tregitopes"; Blood, Oct. 15, 2008 vol. 112, No. 8; Copyright 2008 by The American Society of Hematology.
De Groot et al.; Tregitope Peptides: The Active Pharmaceutical Ingredient of IVIG; Hindaw Publishing Corporation, Clinical and Development Immunology; vol. 2013; Article ID 493138, 6 pages.
Dengler et al.; Structural and functional epitopes of the human adhesion receptor CD58 (LFA-3); Eur. J. Immunol. 1992. 22: 2809-2817; Copyright VCH Verlagsgesellschaft mbH, D-6940 Weinheim, 1992.
DrugBank: Etanercept (DB00005); DrugBank OPen Data Drug & Drug Target Database; www.drugbank.ca/drugs/DB00005.
Drugbank: Rituximab, DrugBank Open Data Drug & Drug Target Database, Feb. 16, 2011, p. 1-12.
Eisenberg, Update on rituximab, ard.bmj.com, Jun. 11, 2012, iv55-iv58, group.bmj.com.
EP 2125883B1; Nov. 25, 2014.
Ephrem et al.; Expansion of CD4+-CD25+ regulatory T cells by intravenous immunoglobulon: a critical factor in controlling experimenal automimmune encephalomyelitis; Blood, Jan. 15, 2008; vol. 111; No. 2.
EPO; Acknowledgement of receipt—Application No. EP08713321.1; Submission No. 3265539; Jan. 23, 2015.
EPO; Acknowledgement of receipt; Application No. EP08713321.1; Submission No. 4073004; Jan. 25, 2016.
EPO; Annex to the communication—opposition; Nov. 25, 2014.
EPO; Boards of Appeal: Appeal No. T0151/15-3.3.04; Change of the composition of the Board; Feb. 13, 2018.
EPO; Boards of Appeal: Appeal No. T0151/15-3.3.04; Forwarding of submissions to parties; Apr. 26, 2017.
EPO; Boards of Appeal: Appeal No. T0151/15-3.3.04; Communication of amended entries in the Register of European Patents; Jan. 28, 2016.
EPO; Boards of Appeal; Appeal No. T0151/15-3.3.04; Forwarding of submission to parties; Dec. 22, 2015.
EPO; Boards of Appeal; Appeal No. T0151/15-3.3.04; Statement setting out the grounds of Appeal; Apr. 9, 2015.
EPO; Commencement of proceedings before the Board of Appeal; Jan. 29, 2015.
EPO; Interlocutory decision in opposition proceedings (Art 101(3)(a) and 106(2) EPC)(2); Nov. 25, 2014.
EPO; Brief Communication—Opposition proceedings; Application No. 08713321.1; Apr. 25, 2013.
EPO; Brief Communication; Extension of time limit pursuant to Rule 132 EPC; Nov. 23, 2012.
EPO; Client Database System (CDS)—clean up; Application No. 08713321.1; Mar. 14, 2014.
EPO; Communication about missing advice of delivery (2); Jan. 12, 2015.
EPO; Communication about missing advice of delivery (3); Jan. 20, 2015.
EPO; Communication about Missing Advice of Delivery; Jan. 12, 2015.
EPO; Communication concerning request for correction of printing errors in European patent specification; Application No. 08713321.1; Feb. 4, 2014.
EPO; Communication of a notice of opposition; Application No. 08713321.1; Patent No. 2115 / 2125883; Epivax, Inc.; Jun. 28, 2012.

(56) References Cited

OTHER PUBLICATIONS

EPO; Communication of amended entries concerning the representative; Application No. 08713321.1; Jul. 5, 2016.
EPO; Communication of amended entries concerning the representative; Application No. 08713321.1; Jan. 22, 2014.
EPO; Communication of amended entries concerning the representative; Application No. 08713321.1; May 23, 2016.
EPO; Communication of amended entries in the Register of European Patents; Appeal No. T0151/15-3.3.04; May 24, 2016.
EPO; Communication of further notices of opposition pursuant to Rule 79(2) EPC; Application No. 08713321.1-2115 / 2125883; Epivax, Inc.; Jul. 26, 2012.
EPO; Communication of notices of opposition (R. 79(1) EPC); Application No. 08713321.1; Patent No. 2115 / 2125883; Jul. 26, 2012.
EPO; Extension of time limit pursuant Rule 132 EPC; Nov. 23, 2012.
EPO; Extension of time limit pursuant to Rule 132 EPC; Application No. 08713321.1; Feb. 7, 2013.
EPO; Facts and Submissions: Application No. EP08713321.1; Nov. 25, 2014.
EPO; Information about the result of oral proceedings; Oct. 1, 2014.
EPO; Information about the result of oral proceedings; Application No. 08713321.1.
EPO; Information concerning oral proceedings; Mar. 3, 2014.
EPO; Letter accompanying subsequently filed items; Mar. 31, 2015.
EPO; Letter accompanying subsequently filed items; Application No. 08713321.1.
EPO; Letter accompanying subsequently filed items; Application No. 08713321.1; Aug. 18, 2015.
EPO; Letter accompanying subsequently filed items; Application No. 08713321.1; Dec. 17, 2015.
EPO; Letter accompanying subsequently filed items; Application No. 08713321.1; Jan. 25, 2016.
EPO; Letter accompanying subsequently filed items; Application No. 08713321.1; Apr. 21, 2017.
EPO; Missing advice of delivery; Apr. 8, 2014.
EPO; Notice of Opposition; Application No. 08713321.1; Jun. 20, 2012.
EPO; Preparation for oral proceedings; Application No. 08713321.1; Feb. 17, 2014.
EPO; Submission in opposition proceedings made following summons to attend oral proceedings; Application No. 08713321.1.
EPO; Submission in opposition proceedings made following summons to attend oral proceedings; Application No. 08713321.1; Aug. 1, 2014.
EPO; Submission in opposition proceedings made following summons to attend oral proceedings; Application No. 08713321.1; Aug. 22, 2014.
EPO; Submission in opposition proceedings made following summons to attend oral proceedings; Application No. 08713321.1; Sep. 17, 2014.
EPO; Submission in opposition proceedings made following summons to attend oral proceedings; Application No. EP08713321.1; Sep. 24, 2014.
EPO; Submission in opposition proceedings; Application No. 08713321.1; Aug. 28, 2014.
EPO; Submission in opposition proceedings; Application No. 08713321.1; Feb. 5, 2013.
EPO; Submission in opposition proceedings; Application No. 08713321.1; Aug. 28, 2013.
EPO; Submission in Opposition proceedings; Application No. 08713321.1; Sep 29, 2014.
EPO; Submission in opposition proceedings; Application No. EP08713321.1; Apr. 5, 2013.
EPO; Summons to attend oral proceedings (2); Mar. 3, 2014.
EPO; Summons to attend oral proceedings pursuant to Rule 115(1) EPC; Mar. 3, 2014.
EPO; Submission in opposition proceedings made following summons to attend oral proceedings; Application No. EP08713321.1; Sep. 29, 2014.
Fanslow et al; Soluble Forms of CD40 Inhibit Biologic Responses of Human B Cells; The Journal of Immunology, vol. 149, 655-660, No. 2, Jul. 15, 1992.
Fricker; Peptide Biosynthesis and Processing; Copyright 1991 by CRC Press, Inc.
Further Submissions; In re: Opposition to EP-B-2125883 Eniitied: "Regulatory T-Cell Epitopes, Compositions and Uses Thereof;" Jul. 30, 2014.
Guillonneau et al.; CD8+ regulatory T Cells in solid organ transplantation; Curr Opin Organ Transplant 15:751-756; Copyright 2010 Wolters Kluwer Health | Lippincott Williams & Wilkins 1087-2418.
Hansson et al.; T-cell epitopes within the complementarity-determining and framework regions of the tumor-derived immunoglobulin heavy chain in multiple myeloma; BLOOD; Jun. 15, 2002; vol. 101, No. 12.

Example EpiBar
Accession: Influenza — Sequence: HA306-318

| Frame Start | Frame Stop | AA Sequence | DRB1*0101 Z score | DRB1*0301 Z score | DRB1*0401 Z score | DRB1*0701 Z score | DRB1*0801 Z score | DRB1*1101 Z score | DRB1*1301 Z score | DRB1*1501 Z score | HITS |
|---|---|---|---|---|---|---|---|---|---|---|---|
| 306 | 314 | PKYVKQNTL | 1.34 | 1.40 | | 2.06 | | | | 1.28 | 1 |
| 307 | 315 | KYVKQNTLK | | | | | | | | | |
| 308 | 316 | YVKQNTLKL | 3.33 | 1.97 | 3.15 | 3.27 | 1.96 | 1.99 | 2.37 | 2.36 | 8 |
| 309 | 317 | VKQNTLKLA | | | | | | 1.59 | 1.67 | | 1 |
| 310 | 318 | KQNTLKLAT | | | | | | | | | |

Z score indicates the potential of a 9-mer frame to bind to a given HLA allele; the strength of the score is indicated by the blue shading as shown below.

| Cluster Regions Outlined | Z scores in top 1% | Z scores in top 5% | Z scores in top 10%* | remaining scores masked* |

Assessments performed: 40       Deviation from Expectation: 17.62

FIG. 17

| Cluster Source Protein | Cluster Location in protein | Cluster Sequence | SEQ ID NO | Peptide ID crosswalk | EpiMatrix Cluster Score | Number of HLA binding |
|---|---|---|---|---|---|---|
| IgG_HC | 289-309 | EEQYNSTYRVVSVLTVLHQDW | 4 | Tregitope-289 | 23.85 | 14 |
| IgG_HC | 167-194 | PAVLQSSGLYSLSSVVTVPSSSLGTQ | 5 | Tregitope-167 | 16.74 | 14 |
| IgG_HV | 9-23 | PGIVRPSQTLSLTCT | 6 | Tregitope-009 | 12.98 | 6 |
| IgG_HV | 9-29 | GGLVQPGGSLRLSCAASGFTF | 7 | | 8.68 | 7 |
| IgG_HV | 9-29 | GGLVQPGRSLRLSCAASGFTF | 8 | | 8.68 | 7 |
| IgG_HV | 16-30 | GASVKVSCKASGYTF | 9 | | 7.36 | 4 |
| IgG_HV | 29-43 | WSWVRQPPGRGLEWI | 10 | Tregitope-029 | 22.25 | 12 |
| IgG_HV | 29-43 | WSWVRQPPGKGLEWI | 11 | | 12.74 | 7 |
| IgG_HV | 29-43 | MHWVRQAPGKGLEWV | 12 | | 22.81 | 11 |
| IgG_HV | 29-43 | MHWVRQAPGQGLEWM | 13 | | 24.92 | 12 |
| IgG_HV | 74-94 | VDTSKNQFSLRLSSVTAADTA | 14 | Tregitope-074 | 12.93 | 10 |
| IgG_HV | 88-108 | NTLYLQMNSLRAEDTAVYYCA | 15 | | 23.7 | 13 |
| IgG_HV | 106-119 | FQHWGQGTLVTVSS | 16 | Tregitope-106 | -0.89 | 0 |
| IgG_HV | 106-119 | FDLWGRGTLVTVSS | 17 | | -0.89 | 0 |
| IgG_HV | 106-119 | FDIWGQGTMTVSS | 18 | | -0.89 | 0 |
| IgG_HV | 106-119 | FDYWGQGTLVTVSS | 19 | | -0.89 | 0 |
| IgG_HV | 106-119 | FDPWGQGTLVTVSS | 20 | | -0.89 | 0 |
| IgG_HV | 106-119 | MDVWGQGTLVTVSS | 21 | | -0.89 | 0 |
| IgG_HV | 106-119 | MDVWGQGTTVTVSS | 22 | | 8.76 | 5 |
| IgG_HV | 134-157 | LNNFYPREAKVQWKVDNALQSGNS | 23 | Tregitope-134 | 13.02 | 10 |
| IgGLCk | 294-307 | KVYACEVTHQGLSS | 24 | Tregitope-294 | 1.69 | 1 |
| IgGLVk | 1-13 | DIQMTQSPSSLSA | 25 | | 9.49 | 5 |
| IgGLVk | 1-13 | EIVLTQSPGTLSL | 26 | | 7.39 | 4 |
| IgGLVk | 16-30 | GDRVTITCRASQGIS | 27 | | 5.61 | 3 |
| IgGLVk | 41-54 | LAWYQQKPGKAPKL | 28 | | 6.99 | 4 |
| IgGLVk | 41-54 | LAWYQQKPGQAPRL | 29 | | 6.99 | 4 |

FROM FIG. 18A

| Protein | Range | Sequence | # | Note | Score | Val |
|---|---|---|---|---|---|---|
| IgGLVκ | 52-66 | LLIYGASSRATGIPD | 30 | | 8.11 | 4 |
| IgGLVκ | 84-98 | GTDFTLTISSLQPED | 31 | | 7.57 | 4 |
| IgGLVλ | 1-13 | SYELTQPPSVSVS | 32 | | 5.31 | 3 |
| IgGLVλ | 16-30 | GQSITISCTGTSSDV | 33 | | 6.29 | 4 |
| IgGLVλ | 39-52 | VSWYQQHPGKAPKL | 34 | | 6.99 | 4 |
| IgGLVλ | 39-52 | VHWYQKPGQAPVL | 35 | | 6.99 | 4 |
| IgGLVλ | 39-52 | VSWYQQLPGTAPKL | 36 | | 6.99 | 4 |
| IgGLVλ | 52-66 | LMIYEVSNRPSGVPD | 37 | | 5.71 | 3 |
| Albumin | 159-177 | LKKYLYEIARRHPYFYAPE | 38 | | 18.37 | 11 |
| Albumin | 175-196 | APELLFFAKRYKAAFTECCQAA | 39 | | 30.75 | 18 |
| Albumin | 362-382 | HPDYSVVLLLRLAKTYETTLE | 40 | | 29.69 | 17 |
| Albumin | 362-376 | HPDYSVVLLLRLAKT | 41 | Tregitope-362 | 10.7 | 7 |
| Albumin | 369-382 | LLRLAKTYETTLE | 42 | Tregitope-369 | 17.96 | 9 |
| Albumin | 422-466 | LGEYKFQNALLVRYTKKVPQVSTPT | 43 | Tregitope-422 | 39.71 | 22 |
| Collagen | 1345-1366 | PADVAIQLTFLRLMSTEASQNI | 44 | | 24.31 | 13 |
| Collagen | 1381-1399 | TGNLKKAILLQGSNEIEIR | 45 | | 16.06 | 10 |
| Collagen | 1113-1128 | DGDFYRADQPRSAPSL | 46 | | 19.74 | 10 |
| Collagen | 1247-1271 | SKEMATQLARMRLLANYASQNITVH | 47 | | 25.51 | 16 |
| Fibrinogen | 149-167 | VQHIQLLQKNVRAQLVDMK | 48 | | 23.95 | 13 |
| Fibrinogen | 705-727 | GEFWLGNDYLHLLTQRGSVLRVE | 49 | | 22 | 13 |
| Fibrinogen | 189-209 | QSGLYFIKPLKANQQFLVYCE | 50 | | 27.16 | 16 |
| Fibrinogen | 250-270 | TEFWLGNEKIHLLISTQSAIPY | 51 | | 19.08 | 12 |
| Haptoglobin | 287-310 | NANFKFTDHLKYVMLPVADQDQCIR | 52 | | 25 | 15 |
| Osteocalcin | 42-67 | GSEVKRPRRYLQWLGAPVPYPDPL | 53 | | 27.96 | 17 |
| Prostaglandin | 124-139 | PCQWNRPTTSTRCCT | 54 | | 15.32 | 9 |
| Prostaglandin | 139-160 | PGEDFRMATLYSRTQTPRAELK | 55 | | 22.14 | 14 |
| Superoxide_Dismu | 153-170 | DGSLWRYRAGLAASLAGP | 56 | | 26.13 | 13 |
| Superoxide_Dismu | 78-98 | VTGVILFRQLAPRAKLDAFFA | 57 | | 30.46 | 18 |
| Transferrin | 61-79 | KASYLDCIRAIAANEADAV | 58 | | 13.77 | 8 |

FIG. 18B

| # BLAST HITS | SEQUENCE EEQYNSTYRVVSVLTVLHQDW | ACCESSION | ORGANISM |
|---|---|---|---|
| 13 | -------------------- | AAG00448 | [synthetic construct] |
| 1 | -Q-----------------N- | 1FRT-C | |
| 1 | --------------T----- | AAM93487 | [Papio anubis anubis] |
| 1 | ----F--------------- | AAB37424 | [Mus sp.] |
| 1 | ----F--------V------ | XP_522970 | [Pan troglodytes] |
| 6 | ----F---------T----- | AAT11503 | [Cercocebus torquatus atys] |
| 1 | --F---F------------- | XP_001168435 | [Pan troglodytes] |
| 4 | ----F---------PI---- | BAA32230 | [Felis catus] |
| 1 | ----F---F----V------ | XP_001168196 | [Pan troglodytes] |
| 3 | ----F---------IQ---- | CAB64864 | [Camelus dromedarius] |
| 7 | -T------------T----- | AAT11502 | [Cercocebus torquatus atys] |
| 1 | ---S--------A-V----- | CAH89990 | [Pongo pygmaeus] |
| 19 | ----F---------PIQ---- | AAA51294 | |
| 11 | -F------------T----- | AAT11504 | [Cercocebus torquatus atys] |
| 2 | ----F---------RIQ---- | CAC44624 | [Equus caballus] |
| 1 | ----F--------IT----- | AAM93489 | [Papio anubis anubis] |
| 2 | ---N---------RIQ---- | AAP82181 | [Equus caballus] |
| 3 | ----F--------A-PIQ---- | AAT65197 | [Tursiops truncatus] |
| 5 | --------F----A-PIQ---- | AAA60738 | |
| 1 | -A-F----------PIQ---- | CAC44761 | [Equus caballus] |
| 6 | ----F--------A-RIQ---- | AAC48761 | [Bos taurus] |
| 1 | -Q-F----------PIE---- | AAL35304 | [Canis familiaris] |
| 1 | -------------PIK---- | AAA82733 | |
| 1 | ---F---F----A-PIM---- | 1IGY-B | |
| 1 | ---F-G--------PIG---- | AAL35302 | [Canis familiaris] |
| 2 | -Q-F---F------PIQ---- | AAA51281 | [Mustela vison] |
| 1 | -Q-F--------A-PIQ---- | AAT65196 | [Tursiops truncatus] |
| 2 | ---F---F----A-PIQ---- | S31459 | |

FIG. 19

| PEPTIDE | DRB*0101 | DRB*0401 | DRB*0701 | DRB*1501 |
|---|---|---|---|---|
| Tregitope-009 | None | medium | high | high |
| Tregitope-029 | medium | medium | medium | medium |
| Tregitope-074 | medium | high | medium | medium |
| Tregitope-167 | high | high | high | high |
| Tregitope-289 | medium | high | high | low |
| Tregitope-134 | None | high | low | low |

FIG. 20

| After initial incubation, restimulation with: | BoNT-L1 | BoNT-L2 | BoNT-L3 | BoNT-L4 | BoNT-L5 | BoNT-Pool | PHA control |
|---|---|---|---|---|---|---|---|
| Incubation with BoNT/A | 522 | 209 | 214 | 434 | 247 | 1,119 | 2,102 |
| Standard Deviation | 98 | 7 | 33 | 39 | 76 | 64 | 546 |
| Incubation with BoNT/A and Tregitopes | 332 | 105 | 57 | 228 | 183 | 460 | 1,750 |
| Standard Deviation | 22 | 42 | 42 | 18 | 57 | 17 | 103 |
| P value of pair wise comparison | 0.007 | 0.003 | 0.003 | 0.001 | 0.124 | 0.008 | 0.000 |
| Percent suppression | 36% | 50% | 73% | 47% | 26% | 59% | 17% |

FIG. 21 mvpctlllllaaalaptqtraenkggdqgpplmtdggggpgpgplssslglalllllllallfwlyivmsd
wtggallvlysfalmliiiiliifififrrdllcplgalcillllmitllllialwnlhggalflgivlfifgc
llvlgiwiyllemlwrlgatiwqllafflaffldlilliialylqqnwwtllvdllwlllflailiwmyy
hggrhsdehhhddslphgpgpggprhrdgvrrpqkrpscigckgpgpgiaeglrallarshvertgpgpg
agvfvyggsktslynlrrgtalaigpgpgtslynlrrgtalaipqcrltplsrlgpgpgresivcyfmvf
lqthifaevlgpgpgaikdlvmtkpaptcnirvgpgpggpqrrggdnhgrgr*dkthtcppcpapellggp*
*svflfppkpkdtlmisrtpevtcvvvdvshedpevkfnwyvdgvevhnaktkpr*eeqnnstnravsvltv
*lhqdw**lngkeykckvsnkalpapiektiskakgqprepqvytlppsrdeltknqvsltclvkgfypsdia*
*vewesnggpennykttppvldsdgsfflyskltvdksrwqqgnvfscsvmhealhnhytqkslslspg*
SEQ ID NO:3

FIG. 22

SEQUENCE LISTING

```
<160> NUMBER OF SEQ ID NOS: 95

<210> SEQ ID NO 1
<211> LENGTH: 2372
<212> TYPE: PRT
<213> ORGANISM: Artificial Sequence
<220> FEATURE:
<223> OTHER INFORMATION: Synthetic construct

<400> SEQUENCE: 1

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
            35                  40                  45

Phe Pro Pro Arg Val Pro Lys Ser Phe Pro Phe Asn Thr Ser Val Val
        50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
```

```
              210                 215                 220
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
                260                 265                 270

Tyr Trp His Val Ile Gly Met Gly Thr Thr Pro Glu Val His Ser Ile
            275                 280                 285

Phe Leu Glu Gly His Thr Phe Leu Val Arg Asn His Arg Gln Ala Ser
        290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
                340                 345                 350

Gln Leu Arg Met Lys Asn Asn Glu Glu Ala Glu Asp Tyr Asp Asp Asp
            355                 360                 365

Leu Thr Asp Ser Glu Met Asp Val Val Arg Phe Asp Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
        450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
        530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
            595                 600                 605

Asn Ile Gln Arg Phe Leu Pro Asn Pro Ala Gly Val Gln Leu Glu Asp
        610                 615                 620

Pro Glu Phe Gln Ala Ser Asn Ile Met His Ser Ile Asn Gly Tyr Val
625                 630                 635                 640
```

```
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
        755                 760                 765
Ser Thr Arg Gln Lys Gln Phe Asn Ala Thr Thr Ile Pro Glu Asn Asp
    770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
                805                 810                 815
Pro Thr Pro His Gly Leu Ser Leu Ser Asp Leu Gln Glu Ala Lys Tyr
            820                 825                 830
Glu Thr Phe Ser Asp Asp Pro Ser Pro Gly Ala Ile Asp Ser Asn Asn
        835                 840                 845
Ser Leu Ser Glu Met Thr His Phe Arg Pro Gln Leu His His Ser Gly
    850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
            900                 905                 910
Leu Ala Ala Gly Thr Asp Asn Thr Ser Ser Leu Gly Pro Pro Ser Met
        915                 920                 925
Pro Val His Tyr Asp Ser Gln Leu Asp Thr Thr Leu Phe Gly Lys Lys
    930                 935                 940
Ser Ser Pro Leu Thr Glu Ser Gly Gly Pro Leu Ser Leu Ser Glu Glu
945                 950                 955                 960
Asn Asn Asp Ser Lys Leu Leu Glu Ser Gly Leu Met Asn Ser Gln Glu
                965                 970                 975
Ser Ser Trp Gly Lys Asn Val Ser Ser Thr Glu Ser Gly Arg Leu Phe
            980                 985                 990
Lys Gly Lys Arg Ala His Gly Pro Ala Leu Leu Thr Lys Asp Asn Ala
        995                 1000                1005
Leu Phe Lys Val Ser Ile Ser Leu Leu Lys Thr Asn Lys Thr Ser
    1010                1015                1020
Asn Asn Ser Ala Thr Asn Arg Lys Thr His Ile Asp Gly Pro Ser
    1025                1030                1035
Leu Leu Ile Glu Asn Ser Pro Ser Val Trp Gln Asn Ile Leu Glu
    1040                1045                1050
```

-continued

Ser Asp Thr Glu Phe Lys Lys Val Thr Pro Leu Ile His Asp Arg
1055                1060                1065

Met Leu Met Asp Lys Asn Ala Thr Ala Leu Arg Leu Asn His Met
1070                1075                1080

Ser Asn Lys Thr Thr Ser Ser Lys Asn Met Glu Met Val Gln Gln
1085                1090                1095

Lys Lys Glu Gly Pro Ile Pro Pro Asp Ala Gln Asn Pro Asp Met
1100                1105                1110

Ser Phe Phe Lys Met Leu Phe Leu Pro Glu Ser Ala Arg Trp Ile
1115                1120                1125

Gln Arg Thr His Gly Lys Asn Ser Leu Asn Ser Gly Gln Gly Pro
1130                1135                1140

Ser Pro Lys Gln Leu Val Ser Leu Gly Pro Glu Lys Ser Val Glu
1145                1150                1155

Gly Gln Asn Phe Leu Ser Glu Lys Asn Lys Val Val Val Gly Lys
1160                1165                1170

Gly Glu Phe Thr Lys Asp Val Gly Leu Lys Glu Met Val Phe Pro
1175                1180                1185

Ser Ser Arg Asn Leu Phe Leu Thr Asn Leu Asp Asn Leu His Glu
1190                1195                1200

Asn Asn Thr His Asn Gln Glu Lys Lys Ile Gln Glu Glu Ile Glu
1205                1210                1215

Lys Lys Glu Thr Leu Ile Gln Glu Asn Val Val Leu Pro Gln Ile
1220                1225                1230

His Thr Val Thr Gly Thr Lys Asn Phe Met Lys Asn Leu Phe Leu
1235                1240                1245

Leu Ser Thr Arg Gln Asn Val Glu Gly Ser Tyr Asp Gly Ala Tyr
1250                1255                1260

Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser His Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser His Leu Pro Ala Ala Ser Tyr Arg Lys Lys
1430                1435                1440

Asp Ser Gly Val Gln Glu Ser Ser His Phe Leu Gln Gly Ala Lys

```
            1445                1450                1455
Lys Asn Asn Leu Ser Leu Ala Ile Leu Thr Leu Glu Met Thr Gly
    1460                1465                1470

Asp Gln Arg Glu Val Gly Ser Leu Gly Thr Ser Ala Thr Asn Ser
    1475                1480                1485

Val Thr Tyr Lys Lys Val Glu Asn Thr Val Leu Pro Lys Pro Asp
    1490                1495                1500

Leu Pro Lys Thr Ser Gly Lys Val Glu Leu Leu Pro Lys Val His
    1505                1510                1515

Ile Tyr Gln Lys Asp Leu Phe Pro Thr Glu Thr Ser Asn Gly Ser
    1520                1525                1530

Pro Gly His Leu Asp Leu Val Glu Gly Ser Leu Leu Gln Gly Thr
    1535                1540                1545

Glu Gly Ala Ile Lys Trp Asn Glu Ala Asn Arg Pro Gly Lys Val
    1550                1555                1560

Pro Phe Leu Arg Val Ala Thr Glu Ser Ser Ala Lys Thr Pro Ser
    1565                1570                1575

Lys Leu Leu Asp Pro Leu Ala Trp Asp Asn His Tyr Gly Thr Gln
    1580                1585                1590

Ile Pro Lys Glu Glu Trp Lys Ser Gln Glu Lys Ser Pro Glu Lys
    1595                1600                1605

Thr Ala Phe Lys Lys Lys Asp Thr Ile Leu Ser Leu Asn Ala Cys
    1610                1615                1620

Glu Ser Asn His Ala Ile Ala Ile Asn Glu Gly Gln Asn Lys
    1625                1630                1635

Pro Glu Ile Glu Val Thr Trp Ala Lys Gln Gly Arg Thr Glu Arg
    1640                1645                1650

Leu Cys Ser Gln Asn Pro Pro Val Leu Lys Arg His Gln Arg Glu
    1655                1660                1665

Ile Thr Arg Thr Thr Leu Gln Ser Asp Gln Glu Glu Ile Asp Tyr
    1670                1675                1680

Asp Asp Thr Ile Ser Val Glu Met Lys Lys Glu Asp Phe Asp Ile
    1685                1690                1695

Tyr Asp Glu Asp Glu Asn Gln Ser Pro Arg Ser Phe Gln Lys Lys
    1700                1705                1710

Thr Arg His Tyr Phe Ile Ala Ala Val Glu Arg Leu Trp Asp Tyr
    1715                1720                1725

Gly Met Ser Ser Ser Pro His Val Leu Arg Asn Arg Ala Gln Ser
    1730                1735                1740

Gly Ser Val Pro Gln Phe Lys Lys Val Val Phe Gln Glu Phe Thr
    1745                1750                1755

Asp Gly Ser Phe Thr Gln Pro Leu Tyr Arg Gly Glu Leu Asn Glu
    1760                1765                1770

His Leu Gly Leu Leu Gly Pro Tyr Ile Arg Ala Glu Val Glu Asp
    1775                1780                1785

Asn Ile Met Val Thr Phe Arg Asn Gln Ala Ser Arg Pro Tyr Ser
    1790                1795                1800

Phe Tyr Ser Ser Leu Ile Ser Tyr Glu Glu Asp Gln Arg Gln Gly
    1805                1810                1815

Ala Glu Pro Arg Lys Asn Phe Val Lys Pro Asn Glu Thr Lys Thr
    1820                1825                1830

Tyr Phe Trp Lys Val Gln His Met Ala Pro Thr Lys Asp Glu
    1835                1840                1845
```

-continued

```
Phe Asp Cys Lys Ala Trp Ala Tyr Phe Ser Asp Val Asp Leu Glu
    1850            1855                1860
Lys Asp Val His Ser Gly Leu Ile Gly Pro Leu Leu Val Cys His
    1865            1870                1875
Thr Asn Thr Leu Asn Pro Ala His Gly Arg Gln Val Thr Val Gln
    1880            1885                1890
Glu Phe Ala Leu Phe Phe Thr Ile Phe Asp Glu Thr Lys Ser Trp
    1895            1900                1905
Tyr Phe Thr Glu Asn Met Glu Arg Asn Cys Arg Ala Pro Ser Asn
    1910            1915                1920
Ile Gln Met Glu Asp Pro Thr Phe Lys Glu Asn Tyr Arg Phe His
    1925            1930                1935
Ala Ile Asn Gly Tyr Ile Met Asp Thr Leu Pro Gly Leu Val Met
    1940            1945                1950
Ala Gln Asp Gln Arg Ile Arg Trp Tyr Leu Leu Ser Met Gly Ser
    1955            1960                1965
Asn Glu Asn Ile His Ser Ile His Phe Ser Gly His Val Phe Thr
    1970            1975                1980
Val Arg Lys Lys Glu Glu Tyr Lys Met Ala Leu Tyr Asn Leu Tyr
    1985            1990                1995
Pro Gly Val Phe Glu Thr Val Glu Met Leu Pro Ser Lys Ala Gly
    2000            2005                2010
Ile Trp Arg Val Glu Cys Leu Ile Gly Glu His Leu His Ala Gly
    2015            2020                2025
Met Ser Thr Leu Phe Leu Val Tyr Ser Asn Lys Cys Gln Thr Pro
    2030            2035                2040
Leu Gly Met Ala Ser Gly His Ile Arg Asp Phe Gln Ile Thr Ala
    2045            2050                2055
Ser Gly Gln Tyr Gly Gln Trp Ala Pro Lys Leu Ala Arg Leu His
    2060            2065                2070
Tyr Ser Gly Ser Ile Asn Ala Trp Ser Thr Lys Glu Pro Phe Ser
    2075            2080                2085
Trp Ile Lys Val Asp Leu Leu Ala Pro Met Ile Ile His Gly Ile
    2090            2095                2100
Lys Thr Gln Gly Ala Arg Gln Lys Phe Ser Ser Leu Tyr Ile Ser
    2105            2110                2115
Gln Phe Ile Ile Met Tyr Ser Leu Asp Gly Lys Lys Trp Gln Thr
    2120            2125                2130
Tyr Arg Gly Asn Ser Thr Gly Thr Leu Met Val Phe Phe Gly Asn
    2135            2140                2145
Val Asp Ser Ser Gly Ile Lys His Asn Ile Phe Asn Pro Pro Ile
    2150            2155                2160
Ile Ala Arg Tyr Ile Arg Leu His Pro Thr His Tyr Ser Ile Arg
    2165            2170                2175
Ser Thr Leu Arg Met Glu Leu Met Gly Cys Asp Leu Asn Ser Cys
    2180            2185                2190
Ser Met Pro Leu Gly Met Glu Ser Lys Ala Ile Ser Asp Ala Gln
    2195            2200                2205
Ile Thr Ala Ser Ser Tyr Phe Thr Asn Met Phe Ala Thr Trp Ser
    2210            2215                2220
Pro Ser Lys Ala Arg Leu His Leu Gln Gly Arg Ser Asn Ala Trp
    2225            2230                2235
```

```
Arg Pro Gln Val Asn Asn Pro Lys Glu Trp Leu Gln Val Asp Phe
2240                2245                2250

Gln Lys Thr Met Lys Val Thr Gly Val Thr Thr Gln Gly Val Lys
2255                2260                2265

Ser Leu Leu Thr Ser Met Tyr Val Lys Glu Phe Leu Ile Ser Ser
2270                2275                2280

Ser Gln Asp Gly His Gln Trp Thr Leu Phe Phe Gln Asn Gly Lys
2285                2290                2295

Val Lys Val Phe Gln Gly Asn Gln Asp Ser Phe Thr Pro Val Val
2300                2305                2310

Asn Ser Leu Asp Pro Pro Leu Leu Thr Arg Tyr Leu Arg Ile His
2315                2320                2325

Pro Gln Ser Trp Val His Gln Ile Ala Leu Arg Met Glu Val Leu
2330                2335                2340

Gly Cys Glu Ala Gln Asp Leu Tyr Glu Gln Tyr Asn Ser Thr
2345                2350                2355

Tyr Arg Val Val Ser Val Leu Thr Val Leu His Gln Asp Trp
2360                2365                2370

<210> SEQ ID NO 2
<211> LENGTH: 2435
<212> TYPE: PRT
<213> ORGANISM: Artificial Sequence
<220> FEATURE:
<223> OTHER INFORMATION: Synthetic construct

<400> SEQUENCE: 2

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
                20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
                100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
                180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220
```

-continued

```
Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
            245                 250                 255

Val Asn Arg Ser Leu Pro Gly Leu Ile Gly Cys His Arg Lys Ser Val
        260                 265                 270

Tyr Trp His Val Ile Gly Met Gly Thr Thr Pro Glu Val His Ser Ile
    275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
    530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
```

-continued

```
                645                 650                 655
Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
                740                 745                 750

Asn Asn Ala Ile Glu Pro Arg Ser Phe Ser Gln Asn Ser Arg His Pro
                755                 760                 765

Ser Thr Arg Gln Lys Gln Phe Asn Ala Thr Thr Ile Pro Glu Asn Asp
770                 775                 780

Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
                835                 840                 845

Ser Leu Ser Glu Met Thr His Phe Arg Pro Gln Leu His His Ser Gly
850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
                915                 920                 925

Pro Val His Tyr Asp Ser Gln Leu Asp Thr Thr Leu Phe Gly Lys Lys
                930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
                980                 985                 990

Lys Gly Lys Arg Ala His Gly Pro Ala Leu Leu Thr Lys Asp Asn Ala
                995                 1000                1005

Leu Phe Lys Val Ser Ile Ser Leu Leu Lys Thr Asn Lys Thr Ser
                1010                1015                1020

Asn Asn Ser Ala Thr Asn Arg Lys Thr His Ile Asp Gly Pro Ser
                1025                1030                1035

Leu Leu Ile Glu Asn Ser Pro Ser Val Trp Gln Asn Ile Leu Glu
                1040                1045                1050

Ser Asp Thr Glu Phe Lys Lys Val Thr Pro Leu Ile His Asp Arg
                1055                1060                1065
```

```
Met Leu Met Asp Lys Asn Ala Thr Ala Leu Arg Leu Asn His Met
    1070            1075            1080

Ser Asn Lys Thr Thr Ser Ser Lys Asn Met Glu Met Val Gln Gln
    1085            1090            1095

Lys Lys Glu Gly Pro Ile Pro Pro Asp Ala Gln Asn Pro Asp Met
    1100            1105            1110

Ser Phe Phe Lys Met Leu Phe Leu Pro Glu Ser Ala Arg Trp Ile
    1115            1120            1125

Gln Arg Thr His Gly Lys Asn Ser Leu Asn Ser Gly Gln Gly Pro
    1130            1135            1140

Ser Pro Lys Gln Leu Val Ser Leu Gly Pro Glu Lys Ser Val Glu
    1145            1150            1155

Gly Gln Asn Phe Leu Ser Glu Lys Asn Lys Val Val Val Gly Lys
    1160            1165            1170

Gly Glu Phe Thr Lys Asp Val Gly Leu Lys Glu Met Val Phe Pro
    1175            1180            1185

Ser Ser Arg Asn Leu Phe Leu Thr Asn Leu Asp Asn Leu His Glu
    1190            1195            1200

Asn Asn Thr His Asn Gln Glu Lys Lys Ile Gln Glu Glu Ile Glu
    1205            1210            1215

Lys Lys Glu Thr Leu Ile Gln Glu Asn Val Val Leu Pro Gln Ile
    1220            1225            1230

His Thr Val Thr Gly Thr Lys Asn Phe Met Lys Asn Leu Phe Leu
    1235            1240            1245

Leu Ser Thr Arg Gln Asn Val Glu Gly Ser Tyr Asp Gly Ala Tyr
    1250            1255            1260

Ala Pro Val Leu Gln Asp Phe Arg Ser Leu Asn Asp Ser Thr Asn
    1265            1270            1275

Arg Thr Lys Lys His Thr Ala His Phe Ser Lys Lys Gly Glu Glu
    1280            1285            1290

Glu Asn Leu Glu Gly Leu Gly Asn Gln Thr Lys Gln Ile Val Glu
    1295            1300            1305

Lys Tyr Ala Cys Thr Thr Arg Ile Ser Pro Asn Thr Ser Gln Gln
    1310            1315            1320

Asn Phe Val Thr Gln Arg Ser Lys Arg Ala Leu Lys Gln Phe Arg
    1325            1330            1335

Leu Pro Leu Glu Glu Thr Glu Leu Glu Lys Arg Ile Ile Val Asp
    1340            1345            1350

Asp Thr Ser Thr Gln Trp Ser Lys Asn Met Lys His Leu Thr Pro
    1355            1360            1365

Ser Thr Leu Thr Gln Ile Asp Tyr Asn Glu Lys Glu Lys Gly Ala
    1370            1375            1380

Ile Thr Gln Ser Pro Leu Ser Asp Cys Leu Thr Arg Ser His Ser
    1385            1390            1395

Ile Pro Gln Ala Asn Arg Ser Pro Leu Pro Ile Ala Lys Val Ser
    1400            1405            1410

Ser Phe Pro Ser Ile Arg Pro Ile Tyr Leu Thr Arg Val Leu Phe
    1415            1420            1425

Gln Asp Asn Ser Ser His Leu Pro Ala Ala Ser Tyr Arg Lys Lys
    1430            1435            1440

Asp Ser Gly Val Gln Glu Ser Ser His Phe Leu Gln Gly Ala Lys
    1445            1450            1455
```

-continued

```
Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser
1520                1525                1530

Pro Gly His Leu Asp Leu Val Glu Gly Ser Leu Leu Gln Gly Thr
1535                1540                1545

Glu Gly Ala Ile Lys Trp Asn Glu Ala Asn Arg Pro Gly Lys Val
1550                1555                1560

Pro Phe Leu Arg Val Ala Thr Glu Ser Ser Ala Lys Thr Pro Ser
1565                1570                1575

Lys Leu Leu Asp Pro Leu Ala Trp Asp Asn His Tyr Gly Thr Gln
1580                1585                1590

Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
```

-continued

```
            1850                1855                1860
Lys Asp Val His Ser Gly Leu Ile Gly Pro Leu Leu Val Cys His
    1865                1870                1875
Thr Asn Thr Leu Asn Pro Ala His Gly Arg Gln Val Thr Val Gln
    1880                1885                1890
Glu Phe Ala Leu Phe Phe Thr Ile Phe Asp Glu Thr Lys Ser Trp
    1895                1900                1905
Tyr Phe Thr Glu Asn Met Glu Arg Asn Cys Arg Ala Pro Ser Asn
    1910                1915                1920
Ile Gln Met Glu Asp Pro Thr Phe Lys Glu Asn Tyr Arg Phe His
    1925                1930                1935
Ala Ile Asn Gly Tyr Ile Met Asp Thr Leu Pro Gly Leu Val Met
    1940                1945                1950
Ala Gln Asp Gln Arg Ile Arg Trp Tyr Leu Leu Ser Met Gly Ser
    1955                1960                1965
Asn Glu Asn Ile His Ser Ile His Phe Ser Gly His Val Phe Thr
    1970                1975                1980
Val Arg Lys Lys Glu Glu Tyr Lys Met Ala Leu Tyr Asn Leu Tyr
    1985                1990                1995
Pro Gly Val Phe Glu Thr Val Glu Met Leu Pro Ser Lys Ala Gly
    2000                2005                2010
Ile Trp Arg Val Glu Cys Leu Ile Gly Glu His Leu His Ala Gly
    2015                2020                2025
Met Ser Thr Leu Phe Leu Val Tyr Ser Asn Lys Cys Gln Thr Pro
    2030                2035                2040
Leu Gly Met Ala Ser Gly His Ile Arg Asp Phe Gln Ile Thr Ala
    2045                2050                2055
Ser Gly Gln Tyr Gly Gln Trp Ala Pro Lys Leu Ala Arg Leu His
    2060                2065                2070
Tyr Ser Gly Ser Ile Asn Ala Trp Ser Thr Lys Glu Pro Phe Ser
    2075                2080                2085
Trp Ile Lys Val Asp Leu Leu Ala Pro Met Ile Ile His Gly Ile
    2090                2095                2100
Lys Thr Gln Gly Ala Arg Gln Lys Phe Ser Ser Leu Tyr Ile Ser
    2105                2110                2115
Gln Phe Ile Ile Met Tyr Ser Leu Asp Gly Lys Lys Trp Gln Thr
    2120                2125                2130
Tyr Arg Gly Asn Ser Thr Gly Thr Leu Met Val Phe Phe Gly Asn
    2135                2140                2145
Val Asp Ser Ser Gly Ile Lys His Asn Ile Phe Asn Pro Pro Ile
    2150                2155                2160
Ile Ala Arg Tyr Ile Arg Leu His Pro Thr His Tyr Ser Ile Arg
    2165                2170                2175
Ser Thr Leu Arg Met Glu Leu Met Gly Cys Asp Leu Asn Ser Cys
    2180                2185                2190
Ser Met Pro Leu Gly Met Glu Ser Lys Ala Ile Ser Asp Ala Gln
    2195                2200                2205
Ile Thr Ala Ser Ser Tyr Phe Thr Asn Met Phe Ala Thr Trp Ser
    2210                2215                2220
Pro Ser Lys Ala Arg Leu His Leu Gln Gly Arg Ser Asn Ala Trp
    2225                2230                2235
Arg Pro Gln Val Asn Asn Pro Lys Glu Trp Leu Gln Val Asp Phe
    2240                2245                2250
```

-continued

```
Gln Lys Thr Met Lys Val Thr Gly Val Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310

Asn Ser Leu Asp Pro Pro Leu Leu Thr Arg Tyr Leu Arg Ile His
    2315                2320                2325

Pro Gln Ser Trp Val His Gln Ile Ala Leu Arg Met Glu Val Leu
    2330                2335                2340

Gly Cys Glu Ala Gln Asp Leu Tyr Glu Glu Gln Tyr Asn Ser Thr
    2345                2350                2355

Tyr Arg Val Val Ser Val Leu Thr Val Leu His Gln Asp Trp Glu
    2360                2365                2370

Glu Gln Tyr Asn Ser Thr Tyr Arg Val Val Ser Val Leu Thr Val
    2375                2380                2385

Leu His Gln Asp Trp Glu Glu Gln Tyr Asn Ser Thr Tyr Arg Val
    2390                2395                2400

Val Ser Val Leu Thr Val Leu His Gln Asp Trp Glu Glu Gln Tyr
    2405                2410                2415

Asn Ser Thr Tyr Arg Val Val Ser Val Leu Thr Val Leu His Gln
    2420                2425                2430

Asp Trp
    2435

<210> SEQ ID NO 3
<211> LENGTH: 628
<212> TYPE: PRT
<213> ORGANISM: Artificial Sequence
<220> FEATURE:
<223> OTHER INFORMATION: Synthetic construct

<400> SEQUENCE: 3

Met Val Pro Cys Thr Leu Leu Leu Leu Ala Ala Leu Ala Pro
1               5                   10                  15

Thr Gln Thr Arg Ala Glu Asn Lys Gly Gly Asp Gln Gly Pro Pro Leu
                20                  25                  30

Met Thr Asp Gly Gly Gly Gly Pro Gly Pro Gly Pro Leu Ser Ser Ser
                35                  40                  45

Leu Gly Leu Ala Leu Leu Leu Leu Leu Ala Leu Leu Phe Trp Leu
    50                  55                  60

Tyr Ile Val Met Ser Asp Trp Thr Gly Gly Ala Leu Leu Val Leu Tyr
65                  70                  75                  80

Ser Phe Ala Leu Met Leu Ile Ile Ile Leu Ile Ile Phe Ile Phe
                85                  90                  95

Arg Arg Asp Leu Leu Cys Pro Leu Gly Ala Leu Cys Ile Leu Leu Leu
                100                 105                 110

Met Ile Thr Leu Leu Leu Ile Ala Leu Trp Asn Leu His Gly Gln Ala
                115                 120                 125

Leu Phe Leu Gly Ile Val Leu Phe Ile Phe Gly Cys Leu Leu Val Leu
                130                 135                 140

Gly Ile Trp Ile Tyr Leu Leu Glu Met Leu Trp Arg Leu Gly Ala Thr
145                 150                 155                 160
```

-continued

Ile Trp Gln Leu Leu Ala Phe Phe Leu Ala Phe Leu Asp Leu Ile
            165                 170                 175

Leu Leu Ile Ile Ala Leu Tyr Leu Gln Gln Asn Trp Trp Thr Leu Leu
            180                 185                 190

Val Asp Leu Leu Trp Leu Leu Leu Phe Leu Ala Ile Leu Ile Trp Met
            195                 200                 205

Tyr Tyr His Gly Gln Arg His Ser Asp Glu His His His Asp Asp Ser
            210                 215                 220

Leu Pro His Gly Pro Gly Pro Gly Gly Pro Arg His Arg Asp Gly Val
225                 230                 235                 240

Arg Arg Pro Gln Lys Arg Pro Ser Cys Ile Gly Cys Lys Gly Pro Gly
            245                 250                 255

Pro Gly Ile Ala Glu Gly Leu Arg Ala Leu Leu Ala Arg Ser His Val
            260                 265                 270

Glu Arg Thr Gly Pro Gly Pro Gly Ala Gly Val Phe Val Tyr Gly Gly
            275                 280                 285

Ser Lys Thr Ser Leu Tyr Asn Leu Arg Arg Gly Thr Ala Leu Ala Ile
            290                 295                 300

Gly Pro Gly Pro Gly Thr Ser Leu Tyr Asn Leu Arg Arg Gly Thr Ala
305                 310                 315                 320

Leu Ala Ile Pro Gln Cys Arg Leu Thr Pro Leu Ser Arg Leu Gly Pro
            325                 330                 335

Gly Pro Gly Arg Glu Ser Ile Val Cys Tyr Phe Met Val Phe Leu Gln
            340                 345                 350

Thr His Ile Phe Ala Glu Val Leu Gly Pro Gly Pro Gly Ala Ile Lys
            355                 360                 365

Asp Leu Val Met Thr Lys Pro Ala Pro Thr Cys Asn Ile Arg Val Gly
            370                 375                 380

Pro Gly Pro Gly Gly Pro Gln Arg Arg Gly Gly Asp Asn His Gly Arg
385                 390                 395                 400

Gly Arg Asp Lys Thr His Thr Cys Pro Pro Cys Pro Ala Pro Glu Leu
            405                 410                 415

Leu Gly Gly Pro Ser Val Phe Leu Phe Pro Pro Lys Pro Lys Asp Thr
            420                 425                 430

Leu Met Ile Ser Arg Thr Pro Glu Val Thr Cys Val Val Val Asp Val
            435                 440                 445

Ser His Glu Asp Pro Glu Val Lys Phe Asn Trp Tyr Val Asp Gly Val
450                 455                 460

Glu Val His Asn Ala Lys Thr Lys Pro Arg Glu Glu Gln Asn Asn Ser
465                 470                 475                 480

Thr Asn Arg Ala Val Ser Val Leu Thr Val Leu His Gln Asp Trp Leu
            485                 490                 495

Asn Gly Lys Glu Tyr Lys Cys Lys Val Ser Asn Lys Ala Leu Pro Ala
            500                 505                 510

Pro Ile Glu Lys Thr Ile Ser Lys Ala Lys Gly Gln Pro Arg Glu Pro
            515                 520                 525

Gln Val Tyr Thr Leu Pro Pro Ser Arg Asp Glu Leu Thr Lys Asn Gln
            530                 535                 540

Val Ser Leu Thr Cys Leu Val Lys Gly Phe Tyr Pro Ser Asp Ile Ala
545                 550                 555                 560

Val Glu Trp Glu Ser Asn Gly Gln Pro Glu Asn Asn Tyr Lys Thr Thr
            565                 570                 575

```
Pro Pro Val Leu Asp Ser Asp Gly Ser Phe Phe Leu Tyr Ser Lys Leu
            580                 585                 590

Thr Val Asp Lys Ser Arg Trp Gln Gln Gly Asn Val Phe Ser Cys Ser
        595                 600                 605

Val Met His Glu Ala Leu His Asn His Tyr Thr Gln Lys Ser Leu Ser
    610                 615                 620

Leu Ser Pro Gly
625

<210> SEQ ID NO 4
<211> LENGTH: 21
<212> TYPE: PRT
<213> ORGANISM: Homo sapiens

<400> SEQUENCE: 4

Glu Glu Gln Tyr Asn Ser Thr Tyr Arg Val Val Ser Val Leu Thr Val
1               5                   10                  15

Leu His Gln Asp Trp
            20

<210> SEQ ID NO 5
<211> LENGTH: 26
<212> TYPE: PRT
<213> ORGANISM: Homo sapiens

<400> SEQUENCE: 5

Pro Ala Val Leu Gln Ser Ser Gly Leu Tyr Ser Leu Ser Ser Val Val
1               5                   10                  15

Thr Val Pro Ser Ser Ser Leu Gly Thr Gln
            20                  25

<210> SEQ ID NO 6
<211> LENGTH: 15
<212> TYPE: PRT
<213> ORGANISM: Homo sapiens

<400> SEQUENCE: 6

Pro Gly Leu Val Arg Pro Ser Gln Thr Leu Ser Leu Thr Cys Thr
1               5                   10                  15

<210> SEQ ID NO 7
<211> LENGTH: 21
<212> TYPE: PRT
<213> ORGANISM: Homo sapiens

<400> SEQUENCE: 7

Gly Gly Leu Val Gln Pro Gly Gly Ser Leu Arg Leu Ser Cys Ala Ala
1               5                   10                  15

Ser Gly Phe Thr Phe
            20

<210> SEQ ID NO 8
<211> LENGTH: 21
<212> TYPE: PRT
<213> ORGANISM: Homo sapiens

<400> SEQUENCE: 8

Gly Gly Leu Val Gln Pro Gly Arg Ser Leu Arg Leu Ser Cys Ala Ala
1               5                   10                  15

Ser Gly Phe Thr Phe
            20
```

<210> SEQ ID NO 9
<211> LENGTH: 15
<212> TYPE: PRT
<213> ORGANISM: Homo sapiens

<400> SEQUENCE: 9

```
Gly Ala Ser Val Lys Val Ser Cys Lys Ala Ser Gly Tyr Thr Phe
1               5                   10                  15
```

<210> SEQ ID NO 10
<211> LENGTH: 15
<212> TYPE: PRT
<213> ORGANISM: Homo sapiens

<400> SEQUENCE: 10

```
Trp Ser Trp Val Arg Gln Pro Pro Gly Arg Gly Leu Glu Trp Ile
1               5                   10                  15
```

<210> SEQ ID NO 11
<211> LENGTH: 15
<212> TYPE: PRT
<213> ORGANISM: Homo sapiens

<400> SEQUENCE: 11

```
Trp Ser Trp Ile Arg Gln Pro Pro Gly Lys Gly Leu Glu Trp Ile
1               5                   10                  15
```

<210> SEQ ID NO 12
<211> LENGTH: 15
<212> TYPE: PRT
<213> ORGANISM: Homo sapiens

<400> SEQUENCE: 12

```
Met His Trp Val Arg Gln Ala Pro Gly Lys Gly Leu Glu Trp Val
1               5                   10                  15
```

<210> SEQ ID NO 13
<211> LENGTH: 15
<212> TYPE: PRT
<213> ORGANISM: Homo sapiens

<400> SEQUENCE: 13

```
Met His Trp Val Arg Gln Ala Pro Gly Gln Gly Leu Glu Trp Met
1               5                   10                  15
```

<210> SEQ ID NO 14
<211> LENGTH: 21
<212> TYPE: PRT
<213> ORGANISM: Homo sapiens

<400> SEQUENCE: 14

```
Val Asp Thr Ser Lys Asn Gln Phe Ser Leu Arg Leu Ser Ser Val Thr
1               5                   10                  15
Ala Ala Asp Thr Ala
                20
```

<210> SEQ ID NO 15
<211> LENGTH: 21
<212> TYPE: PRT
<213> ORGANISM: Homo sapiens

<400> SEQUENCE: 15

```
Asn Thr Leu Tyr Leu Gln Met Asn Ser Leu Arg Ala Glu Asp Thr Ala
1               5                   10                  15
```

Val Tyr Tyr Cys Ala
            20

<210> SEQ ID NO 16
<211> LENGTH: 14
<212> TYPE: PRT
<213> ORGANISM: Homo sapiens

<400> SEQUENCE: 16

Phe Gln His Trp Gly Gln Gly Thr Leu Val Thr Val Ser Ser
1               5                   10

<210> SEQ ID NO 17
<211> LENGTH: 14
<212> TYPE: PRT
<213> ORGANISM: Homo sapiens

<400> SEQUENCE: 17

Phe Asp Leu Trp Gly Arg Gly Thr Leu Val Thr Val Ser Ser
1               5                   10

<210> SEQ ID NO 18
<211> LENGTH: 14
<212> TYPE: PRT
<213> ORGANISM: Homo sapiens

<400> SEQUENCE: 18

Phe Asp Ile Trp Gly Gln Gly Thr Met Val Thr Val Ser Ser
1               5                   10

<210> SEQ ID NO 19
<211> LENGTH: 14
<212> TYPE: PRT
<213> ORGANISM: Homo sapiens

<400> SEQUENCE: 19

Phe Asp Tyr Trp Gly Gln Gly Thr Leu Val Thr Val Ser Ser
1               5                   10

<210> SEQ ID NO 20
<211> LENGTH: 14
<212> TYPE: PRT
<213> ORGANISM: Homo sapiens

<400> SEQUENCE: 20

Phe Asp Pro Trp Gly Gln Gly Thr Leu Val Thr Val Ser Ser
1               5                   10

<210> SEQ ID NO 21
<211> LENGTH: 14
<212> TYPE: PRT
<213> ORGANISM: Homo sapiens

<400> SEQUENCE: 21

Met Asp Val Trp Gly Gln Gly Thr Leu Val Thr Val Ser Ser
1               5                   10

<210> SEQ ID NO 22
<211> LENGTH: 14
<212> TYPE: PRT
<213> ORGANISM: Homo sapiens

<400> SEQUENCE: 22

Met Asp Val Trp Gly Gln Gly Thr Thr Val Thr Val Ser Ser

<210> SEQ ID NO 23
<211> LENGTH: 24
<212> TYPE: PRT
<213> ORGANISM: Homo sapiens

<400> SEQUENCE: 23

Leu Asn Asn Phe Tyr Pro Arg Glu Ala Lys Val Gln Trp Lys Val Asp
1               5                   10                  15

Asn Ala Leu Gln Ser Gly Asn Ser
            20

<210> SEQ ID NO 24
<211> LENGTH: 14
<212> TYPE: PRT
<213> ORGANISM: Homo sapiens

<400> SEQUENCE: 24

Lys Val Tyr Ala Cys Glu Val Thr His Gln Gly Leu Ser Ser
1               5                   10

<210> SEQ ID NO 25
<211> LENGTH: 13
<212> TYPE: PRT
<213> ORGANISM: Homo sapiens

<400> SEQUENCE: 25

Asp Ile Gln Met Thr Gln Ser Pro Ser Ser Leu Ser Ala
1               5                   10

<210> SEQ ID NO 26
<211> LENGTH: 13
<212> TYPE: PRT
<213> ORGANISM: Homo sapiens

<400> SEQUENCE: 26

Glu Ile Val Leu Thr Gln Ser Pro Gly Thr Leu Ser Leu
1               5                   10

<210> SEQ ID NO 27
<211> LENGTH: 15
<212> TYPE: PRT
<213> ORGANISM: Homo sapiens

<400> SEQUENCE: 27

Gly Asp Arg Val Thr Ile Thr Cys Arg Ala Ser Gln Gly Ile Ser
1               5                   10                  15

<210> SEQ ID NO 28
<211> LENGTH: 14
<212> TYPE: PRT
<213> ORGANISM: Homo sapiens

<400> SEQUENCE: 28

Leu Ala Trp Tyr Gln Gln Lys Pro Gly Lys Ala Pro Lys Leu
1               5                   10

<210> SEQ ID NO 29
<211> LENGTH: 14
<212> TYPE: PRT
<213> ORGANISM: Homo sapiens

<400> SEQUENCE: 29

Leu Ala Trp Tyr Gln Gln Lys Pro Gly Gln Ala Pro Arg Leu
1               5                   10

<210> SEQ ID NO 30
<211> LENGTH: 15
<212> TYPE: PRT
<213> ORGANISM: Homo sapiens

<400> SEQUENCE: 30

Leu Leu Ile Tyr Gly Ala Ser Ser Arg Ala Thr Gly Ile Pro Asp
1               5                   10                  15

<210> SEQ ID NO 31
<211> LENGTH: 15
<212> TYPE: PRT
<213> ORGANISM: Homo sapiens

<400> SEQUENCE: 31

Gly Thr Asp Phe Thr Leu Thr Ile Ser Ser Leu Gln Pro Glu Asp
1               5                   10                  15

<210> SEQ ID NO 32
<211> LENGTH: 13
<212> TYPE: PRT
<213> ORGANISM: Homo sapiens

<400> SEQUENCE: 32

Ser Tyr Glu Leu Thr Gln Pro Pro Ser Val Ser Val Ser
1               5                   10

<210> SEQ ID NO 33
<211> LENGTH: 15
<212> TYPE: PRT
<213> ORGANISM: Homo sapiens

<400> SEQUENCE: 33

Gly Gln Ser Ile Thr Ile Ser Cys Thr Gly Thr Ser Ser Asp Val
1               5                   10                  15

<210> SEQ ID NO 34
<211> LENGTH: 14
<212> TYPE: PRT
<213> ORGANISM: Homo sapiens

<400> SEQUENCE: 34

Val Ser Trp Tyr Gln Gln His Pro Gly Lys Ala Pro Lys Leu
1               5                   10

<210> SEQ ID NO 35
<211> LENGTH: 14
<212> TYPE: PRT
<213> ORGANISM: Homo sapiens

<400> SEQUENCE: 35

Val His Trp Tyr Gln Gln Lys Pro Gly Gln Ala Pro Val Leu
1               5                   10

<210> SEQ ID NO 36
<211> LENGTH: 14
<212> TYPE: PRT
<213> ORGANISM: Homo sapiens

<400> SEQUENCE: 36

Val Ser Trp Tyr Gln Gln Leu Pro Gly Thr Ala Pro Lys Leu
1               5                   10

<210> SEQ ID NO 37
<211> LENGTH: 15
<212> TYPE: PRT
<213> ORGANISM: Homo sapiens

<400> SEQUENCE: 37

Leu Met Ile Tyr Glu Val Ser Asn Arg Pro Ser Gly Val Pro Asp
1               5                   10                  15

<210> SEQ ID NO 38
<211> LENGTH: 19
<212> TYPE: PRT
<213> ORGANISM: Homo sapiens

<400> SEQUENCE: 38

Leu Lys Lys Tyr Leu Tyr Glu Ile Ala Arg Arg His Pro Tyr Phe Tyr
1               5                   10                  15

Ala Pro Glu

<210> SEQ ID NO 39
<211> LENGTH: 22
<212> TYPE: PRT
<213> ORGANISM: Homo sapiens

<400> SEQUENCE: 39

Ala Pro Glu Leu Leu Phe Phe Ala Lys Arg Tyr Lys Ala Ala Phe Thr
1               5                   10                  15

Glu Cys Cys Gln Ala Ala
            20

<210> SEQ ID NO 40
<211> LENGTH: 21
<212> TYPE: PRT
<213> ORGANISM: Homo sapiens

<400> SEQUENCE: 40

His Pro Asp Tyr Ser Val Val Leu Leu Leu Arg Leu Ala Lys Thr Tyr
1               5                   10                  15

Glu Thr Thr Leu Glu
            20

<210> SEQ ID NO 41
<211> LENGTH: 15
<212> TYPE: PRT
<213> ORGANISM: Homo sapiens

<400> SEQUENCE: 41

His Pro Asp Tyr Ser Val Val Leu Leu Leu Arg Leu Ala Lys Thr
1               5                   10                  15

<210> SEQ ID NO 42
<211> LENGTH: 14
<212> TYPE: PRT
<213> ORGANISM: Homo sapiens

<400> SEQUENCE: 42

Leu Leu Leu Arg Leu Ala Lys Thr Tyr Glu Thr Thr Leu Glu
1               5                   10

<210> SEQ ID NO 43
<211> LENGTH: 25
<212> TYPE: PRT

<213> ORGANISM: Homo sapiens

<400> SEQUENCE: 43

Leu Gly Glu Tyr Lys Phe Gln Asn Ala Leu Leu Val Arg Tyr Thr Lys
1               5                   10                  15

Lys Val Pro Gln Val Ser Thr Pro Thr
            20                  25

<210> SEQ ID NO 44
<211> LENGTH: 22
<212> TYPE: PRT
<213> ORGANISM: Homo sapiens

<400> SEQUENCE: 44

Pro Ala Asp Val Ala Ile Gln Leu Thr Phe Leu Arg Leu Met Ser Thr
1               5                   10                  15

Glu Ala Ser Gln Asn Ile
            20

<210> SEQ ID NO 45
<211> LENGTH: 19
<212> TYPE: PRT
<213> ORGANISM: Homo sapiens

<400> SEQUENCE: 45

Thr Gly Asn Leu Lys Lys Ala Leu Leu Leu Gln Gly Ser Asn Glu Ile
1               5                   10                  15

Glu Ile Arg

<210> SEQ ID NO 46
<211> LENGTH: 16
<212> TYPE: PRT
<213> ORGANISM: Homo sapiens

<400> SEQUENCE: 46

Asp Gly Asp Phe Tyr Arg Ala Asp Gln Pro Arg Ser Ala Pro Ser Leu
1               5                   10                  15

<210> SEQ ID NO 47
<211> LENGTH: 25
<212> TYPE: PRT
<213> ORGANISM: Homo sapiens

<400> SEQUENCE: 47

Ser Lys Glu Met Ala Thr Gln Leu Ala Phe Met Arg Leu Leu Ala Asn
1               5                   10                  15

Tyr Ala Ser Gln Asn Ile Thr Tyr His
            20                  25

<210> SEQ ID NO 48
<211> LENGTH: 19
<212> TYPE: PRT
<213> ORGANISM: Homo sapiens

<400> SEQUENCE: 48

Val Gln His Ile Gln Leu Leu Gln Lys Asn Val Arg Ala Gln Leu Val
1               5                   10                  15

Asp Met Lys

<210> SEQ ID NO 49
<211> LENGTH: 23
<212> TYPE: PRT

<213> ORGANISM: Homo sapiens

<400> SEQUENCE: 49

Gly Glu Phe Trp Leu Gly Asn Asp Tyr Leu His Leu Leu Thr Gln Arg
1               5                   10                  15

Gly Ser Val Leu Arg Val Glu
            20

<210> SEQ ID NO 50
<211> LENGTH: 21
<212> TYPE: PRT
<213> ORGANISM: Homo sapiens

<400> SEQUENCE: 50

Gln Ser Gly Leu Tyr Phe Ile Lys Pro Leu Lys Ala Asn Gln Gln Phe
1               5                   10                  15

Leu Val Tyr Cys Glu
            20

<210> SEQ ID NO 51
<211> LENGTH: 21
<212> TYPE: PRT
<213> ORGANISM: Homo sapiens

<400> SEQUENCE: 51

Thr Glu Phe Trp Leu Gly Asn Glu Lys Ile His Leu Ile Ser Thr Gln
1               5                   10                  15

Ser Ala Ile Pro Tyr
            20

<210> SEQ ID NO 52
<211> LENGTH: 25
<212> TYPE: PRT
<213> ORGANISM: Homo sapiens

<400> SEQUENCE: 52

Asn Ala Asn Phe Lys Phe Thr Asp His Leu Lys Tyr Val Met Leu Pro
1               5                   10                  15

Val Ala Asp Gln Asp Gln Cys Ile Arg
            20                  25

<210> SEQ ID NO 53
<211> LENGTH: 26
<212> TYPE: PRT
<213> ORGANISM: Homo sapiens

<400> SEQUENCE: 53

Gly Ser Glu Val Val Lys Arg Pro Arg Arg Tyr Leu Tyr Gln Trp Leu
1               5                   10                  15

Gly Ala Pro Val Pro Tyr Pro Asp Pro Leu
            20                  25

<210> SEQ ID NO 54
<211> LENGTH: 16
<212> TYPE: PRT
<213> ORGANISM: Homo sapiens

<400> SEQUENCE: 54

Pro Cys Gln Trp Trp Arg Pro Thr Thr Thr Ser Thr Arg Cys Cys Thr
1               5                   10                  15

<210> SEQ ID NO 55

```
<211> LENGTH: 22
<212> TYPE: PRT
<213> ORGANISM: Homo sapiens

<400> SEQUENCE: 55

Pro Gly Glu Asp Phe Arg Met Ala Thr Leu Tyr Ser Arg Thr Gln Thr
1               5                   10                  15

Pro Arg Ala Glu Leu Lys
            20

<210> SEQ ID NO 56
<211> LENGTH: 18
<212> TYPE: PRT
<213> ORGANISM: Homo sapiens

<400> SEQUENCE: 56

Asp Gly Ser Leu Trp Arg Tyr Arg Ala Gly Leu Ala Ala Ser Leu Ala
1               5                   10                  15

Gly Pro

<210> SEQ ID NO 57
<211> LENGTH: 21
<212> TYPE: PRT
<213> ORGANISM: Homo sapiens

<400> SEQUENCE: 57

Val Thr Gly Val Val Leu Phe Arg Gln Leu Ala Pro Arg Ala Lys Leu
1               5                   10                  15

Asp Ala Phe Phe Ala
            20

<210> SEQ ID NO 58
<211> LENGTH: 19
<212> TYPE: PRT
<213> ORGANISM: Homo sapiens

<400> SEQUENCE: 58

Lys Ala Ser Tyr Leu Asp Cys Ile Arg Ala Ile Ala Ala Asn Glu Ala
1               5                   10                  15

Asp Ala Val

<210> SEQ ID NO 59
<211> LENGTH: 9
<212> TYPE: PRT
<213> ORGANISM: Human influenza virus

<400> SEQUENCE: 59

Pro Arg Tyr Val Lys Gln Asn Thr Leu
1               5

<210> SEQ ID NO 60
<211> LENGTH: 9
<212> TYPE: PRT
<213> ORGANISM: Human influenza virus

<400> SEQUENCE: 60

Arg Tyr Val Lys Gln Asn Thr Leu Lys
1               5

<210> SEQ ID NO 61
<211> LENGTH: 9
<212> TYPE: PRT
<213> ORGANISM: Human influenza virus
```

<400> SEQUENCE: 61

Tyr Val Lys Gln Asn Thr Leu Lys Leu
1               5

<210> SEQ ID NO 62
<211> LENGTH: 9
<212> TYPE: PRT
<213> ORGANISM: Human influenza virus

<400> SEQUENCE: 62

Val Lys Gln Asn Thr Leu Lys Leu Ala
1               5

<210> SEQ ID NO 63
<211> LENGTH: 9
<212> TYPE: PRT
<213> ORGANISM: Human influenza virus

<400> SEQUENCE: 63

Lys Gln Asn Thr Leu Lys Leu Ala Thr
1               5

<210> SEQ ID NO 64
<211> LENGTH: 32
<212> TYPE: DNA
<213> ORGANISM: Artificial Sequence
<220> FEATURE:
<223> OTHER INFORMATION: Synthetic primer

<400> SEQUENCE: 64
gttaactagt tcagctggac cacagccgca gc                                   32

<210> SEQ ID NO 65
<211> LENGTH: 40
<212> TYPE: DNA
<213> ORGANISM: Artificial Sequence
<220> FEATURE:
<223> OTHER INFORMATION: Synthetic primer

<400> SEQUENCE: 65
cgggttaact agttcagaaa tcctttctct tgaccatggc                           40

<210> SEQ ID NO 66
<211> LENGTH: 25
<212> TYPE: DNA
<213> ORGANISM: Artificial Sequence
<220> FEATURE:
<223> OTHER INFORMATION: Synthetic primer

<400> SEQUENCE: 66
ctagcctctg gaatcctttc tcttg                                           25

<210> SEQ ID NO 67
<211> LENGTH: 21
<212> TYPE: PRT
<213> ORGANISM: Artificial Sequence
<220> FEATURE:
<223> OTHER INFORMATION: Synthetic peptide

<400> SEQUENCE: 67

Arg Ile His Met Val Tyr Ser Lys Arg Ser Gly Lys Pro Arg Gly Tyr
1               5                   10                  15

Ala Phe Ile Glu Tyr
            20

-continued

<210> SEQ ID NO 68
<211> LENGTH: 21
<212> TYPE: PRT
<213> ORGANISM: Artificial Sequence
<220> FEATURE:
<223> OTHER INFORMATION: Synthetic peptide

<400> SEQUENCE: 68

Glu Glu Gln Tyr Asn Ser Thr Tyr Arg Val Val Ser Val Leu Thr Val
1               5                   10                  15

Leu His Gln Asp Trp
            20

<210> SEQ ID NO 69
<211> LENGTH: 21
<212> TYPE: PRT
<213> ORGANISM: Rattus norvegicus

<400> SEQUENCE: 69

Glu Gln Gln Tyr Asn Ser Thr Tyr Arg Val Val Ser Val Leu Thr Val
1               5                   10                  15

Leu His Gln Asn Trp
            20

<210> SEQ ID NO 70
<211> LENGTH: 21
<212> TYPE: PRT
<213> ORGANISM: Papio anubis anubis

<400> SEQUENCE: 70

Glu Glu Gln Tyr Asn Ser Thr Tyr Arg Val Val Ser Val Leu Thr Val
1               5                   10                  15

Thr His Gln Asp Trp
            20

<210> SEQ ID NO 71
<211> LENGTH: 21
<212> TYPE: PRT
<213> ORGANISM: Mus sp.

<400> SEQUENCE: 71

Glu Glu Gln Tyr Asn Ser Thr Tyr Arg Val Phe Ser Val Leu Thr Val
1               5                   10                  15

Leu His Gln Asp Trp
            20

<210> SEQ ID NO 72
<211> LENGTH: 21
<212> TYPE: PRT
<213> ORGANISM: Pan troglodytes

<400> SEQUENCE: 72

Glu Glu Gln Tyr Asn Ser Thr Phe Arg Val Val Ser Val Leu Thr Val
1               5                   10                  15

Val His Gln Asp Trp
            20

<210> SEQ ID NO 73
<211> LENGTH: 21
<212> TYPE: PRT
<213> ORGANISM: Cercocebus torquatus atys

<400> SEQUENCE: 73

Glu Glu Gln Phe Asn Ser Thr Tyr Arg Val Val Ser Val Leu Thr Val
1               5                   10                  15

Thr His Gln Asp Trp
            20

<210> SEQ ID NO 74
<211> LENGTH: 21
<212> TYPE: PRT
<213> ORGANISM: Pan troglodytes

<400> SEQUENCE: 74

Glu Glu Gln Phe Asn Ser Thr Phe Arg Val Val Ser Val Leu Thr Val
1               5                   10                  15

Leu His Gln Asp Trp
            20

<210> SEQ ID NO 75
<211> LENGTH: 21
<212> TYPE: PRT
<213> ORGANISM: Felis catus

<400> SEQUENCE: 75

Glu Glu Gln Phe Asn Ser Thr Tyr Arg Val Val Ser Val Leu Pro Ile
1               5                   10                  15

Leu His Gln Asp Trp
            20

<210> SEQ ID NO 76
<211> LENGTH: 21
<212> TYPE: PRT
<213> ORGANISM: Pan troglodytes

<400> SEQUENCE: 76

Glu Glu Gln Phe Asn Ser Thr Phe Arg Val Val Ser Val Leu Thr Val
1               5                   10                  15

Val His Gln Asp Trp
            20

<210> SEQ ID NO 77
<211> LENGTH: 21
<212> TYPE: PRT
<213> ORGANISM: Camelus dromedarius

<400> SEQUENCE: 77

Glu Glu Gln Phe Asn Ser Thr Tyr Arg Val Val Ser Val Leu Thr Ile
1               5                   10                  15

Gln His Gln Asp Trp
            20

<210> SEQ ID NO 78
<211> LENGTH: 21
<212> TYPE: PRT
<213> ORGANISM: Cercocebus torquatus atys

<400> SEQUENCE: 78

Glu Thr Gln Tyr Asn Ser Thr Tyr Arg Val Val Ser Val Leu Thr Val
1               5                   10                  15

Thr His Gln Asp Trp
            20

```
<210> SEQ ID NO 79
<211> LENGTH: 21
<212> TYPE: PRT
<213> ORGANISM: Pongo pygmaeus

<400> SEQUENCE: 79

Glu Glu Gln Ser Asn Ser Thr Tyr Arg Val Val Ser Val Leu Ala Val
1               5                   10                  15

Val His Gln Asp Trp
            20

<210> SEQ ID NO 80
<211> LENGTH: 21
<212> TYPE: PRT
<213> ORGANISM: Sus scrofa

<400> SEQUENCE: 80

Glu Glu Gln Phe Asn Ser Thr Tyr Arg Val Val Ser Val Leu Pro Ile
1               5                   10                  15

Gln His Gln Asp Trp
            20

<210> SEQ ID NO 81
<211> LENGTH: 19
<212> TYPE: PRT
<213> ORGANISM: Cercocebus torquatus atys

<400> SEQUENCE: 81

Gln Phe Asn Ser Thr Tyr Arg Val Val Ser Val Leu Thr Val Thr His
1               5                   10                  15

Gln Asp Trp

<210> SEQ ID NO 82
<211> LENGTH: 21
<212> TYPE: PRT
<213> ORGANISM: Equus caballus

<400> SEQUENCE: 82

Glu Glu Gln Phe Asn Ser Thr Tyr Arg Val Val Ser Val Leu Arg Ile
1               5                   10                  15

Gln His Gln Asp Trp
            20

<210> SEQ ID NO 83
<211> LENGTH: 19
<212> TYPE: PRT
<213> ORGANISM: Papio anubis anubis

<400> SEQUENCE: 83

Gln Phe Asn Ser Thr Tyr Arg Val Val Ser Val Leu Thr Ile Thr His
1               5                   10                  15

Gln Asp Trp

<210> SEQ ID NO 84
<211> LENGTH: 21
<212> TYPE: PRT
<213> ORGANISM: Equus caballus

<400> SEQUENCE: 84

Glu Glu Gln Asn Asn Ser Thr Tyr Arg Val Val Ser Val Leu Arg Ile
1               5                   10                  15

Gln His Gln Asp Trp
```

<210> SEQ ID NO 85
<211> LENGTH: 21
<212> TYPE: PRT
<213> ORGANISM: Tursiops truncatus

<400> SEQUENCE: 85

Glu Glu Gln Phe Asn Ser Thr Tyr Arg Val Val Ser Ala Leu Pro Ile
1               5                   10                  15

Gln His Gln Asp Trp
            20

<210> SEQ ID NO 86
<211> LENGTH: 21
<212> TYPE: PRT
<213> ORGANISM: Rattus norvegicus

<400> SEQUENCE: 86

Glu Glu Gln Tyr Asn Ser Thr Phe Arg Val Val Ser Ala Leu Pro Ile
1               5                   10                  15

Gln His Gln Asp Trp
            20

<210> SEQ ID NO 87
<211> LENGTH: 21
<212> TYPE: PRT
<213> ORGANISM: Equus caballus

<400> SEQUENCE: 87

Glu Ala Gln Phe Asn Ser Thr Tyr Arg Val Val Ser Val Leu Pro Ile
1               5                   10                  15

Gln His Gln Asp Trp
            20

<210> SEQ ID NO 88
<211> LENGTH: 21
<212> TYPE: PRT
<213> ORGANISM: Bos taurus

<400> SEQUENCE: 88

Glu Glu Gln Phe Asn Ser Thr Tyr Arg Val Val Ser Ala Leu Arg Ile
1               5                   10                  15

Gln His Gln Asp Trp
            20

<210> SEQ ID NO 89
<211> LENGTH: 21
<212> TYPE: PRT
<213> ORGANISM: Canis familiaris

<400> SEQUENCE: 89

Glu Gln Gln Phe Asn Ser Thr Tyr Arg Val Val Ser Val Leu Pro Ile
1               5                   10                  15

Glu His Gln Asp Trp
            20

<210> SEQ ID NO 90
<211> LENGTH: 19
<212> TYPE: PRT
<213> ORGANISM: Cricetulus migratorius

<400> SEQUENCE: 90

Gln Tyr Asn Ser Thr Tyr Arg Val Val Ser Val Leu Pro Ile Lys His
1               5                   10                  15

Gln Asp Trp

<210> SEQ ID NO 91
<211> LENGTH: 21
<212> TYPE: PRT
<213> ORGANISM: Mus musculus

<400> SEQUENCE: 91

Glu Glu Gln Phe Asn Ser Thr Phe Arg Val Val Ser Ala Leu Pro Ile
1               5                   10                  15

Met His Gln Asp Trp
            20

<210> SEQ ID NO 92
<211> LENGTH: 21
<212> TYPE: PRT
<213> ORGANISM: Canis familiaris

<400> SEQUENCE: 92

Glu Glu Gln Phe Asn Gly Thr Tyr Arg Val Val Ser Val Leu Pro Ile
1               5                   10                  15

Gly His Gln Asp Trp
            20

<210> SEQ ID NO 93
<211> LENGTH: 21
<212> TYPE: PRT
<213> ORGANISM: Mustela vison

<400> SEQUENCE: 93

Glu Gln Gln Phe Asn Ser Thr Phe Arg Val Val Ser Val Leu Pro Ile
1               5                   10                  15

Gln His Gln Asp Trp
            20

<210> SEQ ID NO 94
<211> LENGTH: 21
<212> TYPE: PRT
<213> ORGANISM: Tursiops truncatus

<400> SEQUENCE: 94

Glu Gln Gln Phe Asn Ser Thr Tyr Arg Val Val Ser Ala Leu Pro Ile
1               5                   10                  15

Gln His Gln Asp Trp
            20

<210> SEQ ID NO 95
<211> LENGTH: 21
<212> TYPE: PRT
<213> ORGANISM: Ovis aries

<400> SEQUENCE: 95

Glu Glu Gln Phe Asn Ser Thr Phe Arg Val Val Ser Ala Leu Pro Ile
1               5                   10                  15

Gln His Gln Asp Trp
            20

REGULATORY T CELL EPITOPES, COMPOSITIONS AND USES THEREOF

RELATED APPLICATIONS

This application is a continuation application of U.S. patent application Ser. No. 14/857,693, filed on Sep. 17, 2015, which is a continuation application of U.S. patent application Ser. No. 12/981,098, filed Dec. 29, 2010, which is a divisional application of U.S. patent application Ser. No. 12/021,832, filed on Jan. 29, 2008, which claims priority to U.S. Provisional Patent Application Ser. No. 60/898,347, filed Jan. 30, 2007. The entire contents of all of the above-listed applications are incorporated by reference herein.

SEQUENCE LISTING

The instant application contains a Sequence Listing which has been submitted in ASCII format via EFS-Web and is hereby incorporated by reference in its entirety. Said ASCII copy, created on Jun. 20, 2018, is named SEQUENCE LISTING_ST25.txt and is 68 KB is size.

FIELD OF THE INVENTION

The invention relates generally to a novel class of T cell epitope compositions (termed "Tregitopes"). The invention provides Tregitope compositions, methods for their preparation and use.

BACKGROUND

Artificial induction of tolerance to self or to foreign antigens is the goal of therapy for autoimmunity, transplantation allergy and other diseases, and is also desirable in the context of therapy with autologous proteins and non-autologous proteins. Until recently, therapeutic tolerance induction relied on broad-based approaches that resulted in cellular depletion and cytokine profile alteration. These broad-based approaches weaken the immune system in general and leave many subjects vulnerable to opportunistic infections, autoimmune attack and cancer. There is a need in the art for less aggressive and more targeted approaches to the induction of immune tolerance.

Immune tolerance is regulated by a complex interplay between T cells, B cells, cytokines and surface receptors. Initial self/non-self discrimination occurs in the thymus during neonatal development where medullary epithelial cells express specific self protein epitopes to immature T cells. T cells recognizing self antigens with high affinity are deleted, but autoreactive T cells with moderate affinity sometimes avoid deletion and can be converted to so called 'natural' regulatory T cells ($T_{Reg}$) cells. These natural $T_{Reg}$ cells are exported to the periphery and provide for constant suppression of autoimmunity.

A second form of tolerance occurs in the periphery where mature T cells are converted to an 'adaptive' $T_{Reg}$ phenotype upon activation via their T cell receptor in the presence of IL-10 and TGF-β. The possible roles for these 'adaptive' $T_{Reg}$ cells include dampening immune response following the successful clearance of an invading pathogen as a means of controlling excessive inflammation as might be caused by an allergic reaction or low level chronic infection, or possibly to facilitate co-existence with beneficial symbiotic bacteria and viruses. 'Adaptive' $T_{Reg}$ may also play a role in managing the life cycle of human antibodies that have undergone somatic hypermutation.

Natural regulatory T cells are a critical component of immune regulation in the periphery. Upon activation through their TCR natural Tregs are capable of suppressing bystander effector T cell responses to unrelated antigens through contact dependent and independent mechanisms. In addition the cytokines released by these cells including IL-10 and TGF-β, are capable of inducing antigen-specific adaptive Tregs. Despite extensive efforts, with few exceptions, the antigen specificity of natural Tregs, and more importantly natural Tregs circulating in clinically significant volumes, is still unknown.

There is need in the art for the identification of regulatory T cell epitopes contained in common autologous proteins such as IgG ("Tregitopes") and for methods for related to their preparation and of use.

SUMMARY

The present invention harnesses the functions of regulatory T cells ($T_{Reg}$), particularly those cells that already regulate immune responses to foreign and self proteins in the periphery (pre-existing or natural $T_{Reg}$). In one aspect, the invention provides T-cell epitope polypeptide compositions.

The selective engagement and activation of pre-existing natural Treg through the use of Tregitopes and Tregitope-antigen fusions, is therapeutically valuable as a means of treatment for any disease or condition marked by the presence of an unwanted immune response. Examples include the following: Autoimmune disease such as type 1 diabetes, MS, Lupus, and RA; Transplant related disorders such as Graft vs. Host disease (GVHD); Allergic reactions; Immune rejection of biologic medicines such as monoclonal antibodies, replacement proteins such as FVIII or Insulin, the use of therapeutic toxins such as Botulinum toxin; and the management of immune response to infectious disease whether acute or chronic.

In one embodiment, the present invention is directed to a T-cell epitope polypeptide composition comprising at least one polypeptide selected from the group consisting of: SEQ ID NOS:4-58. In a particular embodiment, the invention is directed to a pharmaceutical composition comprising a polypeptide of the invention and a pharmaceutically acceptable carrier.

In one embodiment, the present invention is directed to a nucleic acid encoding at least one T-cell epitope polypeptide selected from the group consisting of: SEQ ID NOS:4-58. In a particular embodiment, the invention is directed to a vector comprising a nucleic acid of the invention. In another embodiment, the invention is directed to a cell comprising a vector of the invention.

In one embodiment, the invention is directed to a method of treating or preventing a medical condition in a subject in need thereof comprising administering a therapeutically effective amount of a T-cell epitope polypeptide selected from the group consisting of: SEQ ID NOS:4-58. In a particular embodiment, the medical condition is selected from the group consisting of: an allergy, an autoimmune disease, a transplant related disorder, graft versus host disease, an enzyme or protein deficiency disorder, a hemostatic disorder, cancer, infertility; and a viral, bacterial or parasitic infection.

In one embodiment, the invention is directed to a kit for preventing or treating a medical condition in a subject, wherein the kit comprises at least one T-cell epitope polypeptide selected from the group consisting of: SEQ ID NOS:4-58.

In one embodiment, the present invention is directed to a method for expanding a population of regulatory T cells, comprising: (a) providing a biological sample from a subject; and (b) isolating regulatory T-cells from the biological sample; and contacting the isolated regulatory T-cells with an effective amount of a Tregitope composition of the invention under conditions wherein the T-regulatory cells increase in number to yield an expanded regulatory T-cell composition, thereby expanding the regulatory T-cells in the biological sample.

In one embodiment, the present invention is directed to a method for stimulating regulatory T cells in a biological sample, comprising: (a) providing a biological sample from a subject; (b) isolating regulatory T-cells from the biological sample; and contacting the isolated regulatory T-cells with an effective amount of a Tregitope composition of the invention under conditions wherein the T-regulatory cells are stimulated to alter one or more biological function, thereby stimulating the regulatory T-cells in the biological sample.

In one embodiment, the present invention is directed to a method for repressing immune response in a subject, comprising administering a composition comprising a therapeutically effective amount of a peptide comprising a Tregitope to the subject, wherein the peptide represses the immune response. In a particular embodiment, the peptide suppresses effector T cell response. In a particular embodiment, the peptide suppresses helper T cell response. In another embodiment, the peptide suppresses B cell response.

In one embodiment, the present invention is directed to a method of suppressing antigen specific immune response in a subject through the administration of a therapeutically effective amount of a composition comprising one or more Tregitopes, wherein the one or more Tregitopes are either covalently bound, non-covalently bound or in admixture with a specific target antigen resulting in the diminution of immune response against the target antigen. In a particular embodiment, the suppressive effect is mediated by natural Treg. In another embodiment, the suppressive effect is mediated by adaptive Treg. In another embodiment, the peptide suppresses effector T cell response. In another embodiment, the peptide suppresses helper T cell response. In another embodiment, the peptide suppresses B cell response. In a particular embodiment, the peptide comprises a sequence selected from the group consisting of: SEQ ID NOS:4-58.

In one embodiment, the present invention is directed to a method for enhancing the immunogenicity of a vaccine delivery vector, comprising identification and removal of regulatory T cell epitopes. In a particular embodiment, the T cell epitopes are selected from the group consisting of: SEQ ID NOS:4-58.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 17 depicts an example of an immunogenic influenza HA peptide that contains an EpiBar and the EpiMartix analysis of the promiscuous influenza epitope. The influenza HA peptide scores extremely high for all eight alleles in EpiMatrix and has a cluster score of 18. Cluster scores of 10 are considered significant. The band-like EpiBar pattern is characteristic of promiscuous epitopes. Results are shown for PRYVKQNTL (SEQ ID NO:59), RYVKQNTLK (SEQ ID NO:60), YVKQNTLKL (SEQ ID NO:61), VKQNTLKLA (SEQ ID NO:62) and KQNTLKLAT (SEQ ID NO:63). Z score indicates the potential of a 9-mer frame to bind to a given HLA allele. All scores in the top 5% are considered "hits", while non hits (*) below 10% are masked in FIG. 17 for simplicity.

FIG. 18A and FIG. 18B depict the Tregitopes on the instant-disclosure and their EpiMatrix Scores.

FIG. 19 illustrates an exemplary BLAST report of Tregitope-289 (SEQ ID NO: 4) showing homology of Tregitope-289 to other organisms. Homology analysis of the IgG-derived Tregitopes to non-human species was performed by uploading the sequences into the Basic Local Alignment Search Tool (BLAST) via the NCBI website (ncbi.nlm.nih.gov/blast). The BLAST program compares protein sequences to sequence databases and calculates the statistical significance of matches in order to find regions of local similarity between sequences. The IgG-derived Tregitopes were found to be conserved across non-human species such as mouse, rat, cat, camel, cow and non-human primates.

FIG. 20 illustrates the binding of affinity of the Tregitopes of the instant disclosure to each of 4 common HLA, showing that the instant Tregitopes identified by in silico analysis bound to human MHC molecules. Soluble MHC binding assays were performed on the synthetic IgG Tregitopes of the instant disclosure according to the methods described below in the EXEMPLIFICATION section. $IC_{50}$ values (µM) were derived by a six point inhibition curve of a strong binding control peptide.

FIG. 21 depicts the results of interferon-γ ELISpot responses to Botulinum Toxin Antigen stimulus following incubation with or without Tregitopes (spot forming cells over no-restimulus background). The results demonstrate that a pool of Tregitopes downregulates in vitro effector responses to co-administered peptide epitopes derived from Botulinum neurotoxin, a protein used to treat dystonia. PBMCs from a subject with evidence of inhibitors (anti-BoNT antibodies) were cultured for 8 days with or without a pool of Tregitope peptides (Tregitope-167, Tregitope-134, Tregitope-289). Cells were harvested and washed with PBS. $2.5 \times 10^5$ cells were re-stimulated in an IFN-γ ELISpot plate with individual BoNT peptides, a pool of BoNT peptides, PHA positive control (not shown) or no-stimulus control. Peptides for which there was no significant baseline response are not shown. Response to positive control PHA was robust following both culture conditions.

FIG. 22 illustrates one embodiment of a chimeric protein where a pseudo-protein of interest is a string of immunogenic T cell epitopes derived from the Epstein Barr Virus (EBV) fused to a modified Fc protein in which the Tregitope has been modified to no longer bind MHC class II molecules and can not stimulate natural regulatory T cells. EBV-Tregitope modified Fc SEQUENCE (Kb SIGNAL SEQUENCE) is designated as underlined text. The Tregitope is designated as bold text. The Tregitope modified amino acids are designated as shaded text. The human Fc region is designated as italicized text.

DETAILED DESCRIPTION

General

Figure 1:
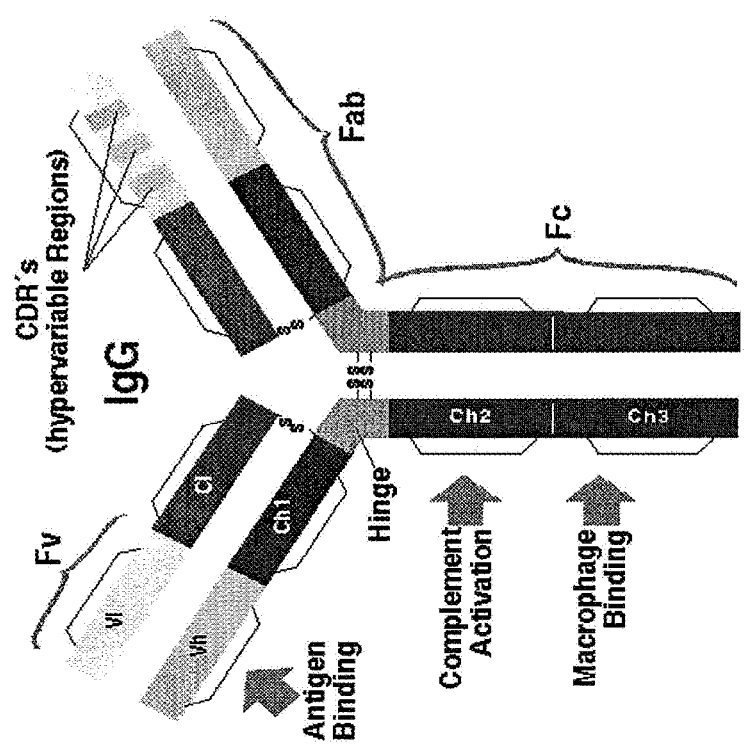
FIG. 1 is a schematic diagram of immunoglobulin G (IgG).

The adaptive immune cascade begins when soluble protein antigens are taken up by Antigen Presenting Cells (APCs) and processed through the Class II antigen presentation pathway. Protein antigens in the Class II presentation pathway are degraded by various proteases found in the Endoplasmic Reticulum. Some of the resulting protein fragments are bound to Class II MHC molecules. Peptide-loaded MHC molecules are trafficked to the cell surface where they are interrogated by CD4+ T cells. Peptide fragments that are capable of binding to an MHC molecule and mediating the cell to cell interaction between APC and circulating T cells are referred to as T cell epitopes. Recognition of these peptide-MHC complexes by CD4+ T cells can lead to either an immune activating or immune suppressive response based on the phenotype of the responding T cells and the local cytokine/chemokine milieu. In general, engagement between the MHC/peptide complex and the T cell receptor (TCR) of T effector cells leads to activation and the secretion of pro-inflammatory cytokines such as IL-4, and IFN-γ. On the other hand the activation of natural T regulatory cells (TReg) leads to the expression of the immune suppressive cytokines IL-10 and TGF-γ, among others (Shevach, E., *Nat. Rev. Immunol.*, 2:389-400, 2002). These cytokines act directly on nearby effector T cells leading in some cases to anergy or apoptosis. In other cases regulatory cytokines and chemokines convert effector T cells to T regulatory phenotypes; this process is referred here as "induced" or "adaptive" tolerance. T cell epitopes that are capable of binding to MHC molecules and engaging and activating circulating Treg are referred to as Tregitopes.

Initial self/non-self discrimination occurs in the thymus during neonatal development where medullary epithelial cells express specific self protein epitopes to immature T cells. T cells recognizing self antigens with high affinity are deleted, but autoreactive T cells with moderate affinity sometimes avoid deletion and can be converted to so called natural regulatory T cells (TReg) cells. These natural TReg cells are exported to the periphery and provide for constant suppression of autoimmunity. Natural regulatory T cells are a critical component of immune regulation and self tolerance.

Self tolerance is regulated by a complex interplay between T cells, B cells, cytokines and surface receptors. T regulatory immune responses counterbalance T effector immune response to protein antigens (whether self or foreign). A tilt of the balance toward the autoreactive side, either by increasing the number or function of autoreactive T effector cells or by diminishing the number or function of T regulatory cells, is manifested as autoimmunity.

A second form of tolerance occurs in the periphery where mature T cells are converted to an 'adaptive' TReg phenotype upon activation via their T cell receptor in the presence of IL-10 and TGF-γ, usually supplied by bystander T regulatory cells. The possible roles for these 'adaptive' TReg cells include dampening immune response following the successful clearance of an invading pathogen as a means of controlling excessive inflammation as might be caused by an allergic reaction or low level chronic infection, or possibly to facilitate co-existence with beneficial symbiotic bacteria and viruses. 'Adaptive' TReg may also play a role in managing the life cycle of human antibodies that have undergone somatic hypermutation.

It is thought the constant region of immunoglobulin contains several important Tregitopes whose primary function is to suppress immune response to hypermutated CDRs. Due to the high volumes of circulating IgG it is likely that there are also high volumes of T regulatory cells corresponding to the Tregitopes contained in IgG. As a partial proof of this assertion consider that chimeric proteins comprising an Fc portion of an immunoglobulin bestow several desirable properties on a chimeric protein including increased stability, increased serum half life, binding to Fc receptors, and reduced immunogenicity (Lei, T. et al., *Cell. Immunol.*, 235:12-20, 2005, Baxevanis, C. et al., *Eur. J. Immunol.*, 16:1013-1016, 1986).

TReg cells are also instrumental in B cell tolerance. B cells express a single low affinity Fc receptor, FcγRIIB on their cell surface (Ravetch, J. et al., *Science*, 234:718-725, 1986). This receptor contains the immunoreceptor tyrosine-based inhibition motif sequence (ITIM) in its cytoplasmic domain. Co-ligation of FCγRIIB and the BCR by immune complexes act to trigger the tyrosine phosphorylation of the ITIM leading to the recruitment of the inositol phosphatase, SHIP, which inhibits BCR-triggered proliferation by interfering with the activation of MAP kinases and blocks phagocytosis by the dissociation of Burton's tyrosine kinase (Btk) from the cell membrane, which inhibits calcium influx into the cell. FcγRIIB can also induce apoptosis independent of the ITIM. Upon homo-aggregation of FcRIIB by ICs, the association of Btk with the cell membrane is enhanced triggering an apoptotic response (Pearse, R. et al., *Immunity*, 10:753-760, 1999). Expression of FcγRIIB is highly variable and cytokine dependent. IL-4 and IL-10, which are expressed by activated Th2 and TReg cells, have been shown to act synergistically to enhance FcγRIIB expression (Joshi, T. et al., *Mol. Immunol.*, 43:839-850, 2006) thus aiding in the suppression of a humoral response.

It is possible to exploit Tregitope specific TReg cells to suppress unwanted immune responses and to induce adaptive TReg to co-delivered proteins. This discovery has implications for the design of therapeutic regimens and antigen-specific therapies for transplantation, protein therapeutics, allergy, chronic infection, autoimmunity and vaccine design. Administration of a drug, a protein, or an allergen in conjunction with Tregitope can suppress effector immune response. Tregitope can be used to deliberately manipulate the immune system toward tolerance.

The peptides of the current invention are useful in the selective engagement and activation of regulatory T cells. It is demonstrated herein that certain pre-existing populations of regulatory T cells can be engaged, activated and applied to the suppression of unwanted immune responses in both systemic and limited, disease specific, contexts.

Despite extensive efforts, with few exceptions, the antigen specificity of natural Tregs, and more importantly natural Tregs circulating in clinically significant volumes, is unknown. Presented herein is a demonstration that certain human proteins circulating in the blood steam, such as immunoglobulins or the serum protein Albumin, contain T cell epitopes that relate to naturally occurring populations of regulatory T cells. In the course of normal immune surveillance these proteins are taken up by professional APC such as dendritic cells or macrophages and degraded. During the degradation process some of the epitopes contained in these proteins are bound to MHC molecules, transported to the cell surface presented to regulatory T cells. Those cells, once activated by the APC, release cytokines and chemokines help to suppress autoimmune responses that would otherwise hinder the function of the extra cellular proteins.

By using the peptides of the invention to selectively activate these pre-existing regulatory T cells, it is herein shown that the peptides of the invention can be used to suppress a variety of unwanted immune responses. In its simplest form systemic application of the peptides of the invention can be used as a generalized immune suppressant useful for controlling severe autoimmune reactions such as, for example, MS flare-ups, allergic reactions, transplant reactions, or uncontrolled response to infection. In a more controlled application, topically applied to joints affected by rheumatoid arthritis (RA) for example, the peptide of the invention can be used to suppress localized autoimmune responses. In a targeted application, such as might be achieved through the fusion or bonding of the peptides to certain other T cell epitopes, the peptides can suppress highly specific immune reactions while leaving the balance of the immune system intact. For example, through the delivery of a regulatory peptide fused to an autoimmune antigen such as insulin, or an allergen such as Brazil nut antigen, the immune system can be trained to "tolerate" the co-delivered antigen by converting the phenotype of responding effector T cells to that of adaptive regulatory T cells.

As stated above the peptides of the current invention are derived from circulating extracellular proteins. To be useful these peptides must be true T cell epitopes (i.e., capable of binding to both MHC molecules and TCRs), and be related to a pre-existing population of regulatory T cells that is sufficiently large to have a therapeutic affect. T cell epitope clusters, epitopes capable of binding to multiple MHC alleles and multiple TCRs, are key to satisfying this latter qualification.

Definitions

To further facilitate an understanding of the present invention, a number of terms and phrases are defined below.

As used herein, the term "biological sample" as refers to any sample of tissue, cells or secretions from an organism.

As used herein, the term "transplantation" refers to the process of taking a cell, tissue, or organ, called a "transplant" or "graft" from one subject and placing it or them into a (usually) different subject. The subject who provides the transplant is called the "donor", and the subject who received the transplant is called the "recipient". An organ or graft transplanted between two genetically different subjects of the same species is called an "allograft". A graft transplanted between subjects of different species is called a "xenograft".

As used herein, the term "medical condition" includes, but is not limited to, any condition or disease manifested as one or more physical and/or psychological symptoms for which treatment and/or prevention is desirable, and includes previously and newly identified diseases and other disorders.

As used herein, the term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, malignant melanoma, invading pathogens, cells or tissues infected with pathogens, or, in cases of autoimmunity or pathological inflammation, normal human cells or tissues.

As used herein, the term "effective amount" of a composition, is a quantity sufficient to achieve a desired therapeutic and/or prophylactic effect, e.g., an amount that results in the prevention of, or a decrease in, the symptoms associated with a disease that is being treated. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with each other or with one or more additional therapeutic compounds.

As used herein, the term "T cell epitope" means a protein determinant, 7 to 30 amino acids in length, and capable of specific binding to HLA molecules and interacting with specific TCRs. Generally, T cell epitopes are linear and do not express specific three dimensional characteristics. T cell epitopes are not affected by the presence of denaturing solvents.

As used herein, the term "B cell epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the term MHC complex refers to a protein complex capable of binding with a specific repertoire of polypeptides known as HLA ligands and transporting said ligands to the cell surface.

As used herein, the term "MHC Ligand" means a polypeptide capable of binding to one or more specific MHC alleles. The term "HLA ligand" is interchangeable with the term MHC Ligand. Cells expressing MHC/Ligand complexes on their surface are referred to as "Antigen Presenting Cells" (APCs).

As used herein, the term T Cell Receptor or TCR refers to a protein complex expressed by T cells that is capable of engaging a specific repertoire of MHC/Ligand complexes as presented on the surface of APCs.

As used herein, the term "T cell epitope" means an MHC ligand capable of interacting with specific T cell receptors (TCRs). T cell epitopes can be predicted by in silico methods (De Groot, A. et al., *AIDS Res. Hum. Retroviruses*, 13:539-541, 1997; Schafer, J. et al., *Vaccine*, 16:1880-1884, 1998; De Groot, A. et al., *Vaccine*, 19:4385-95, 2001; De Groot, A. et al., *Vaccine*, 21:4486-504, 2003).

As used herein, the term "MHC Binding Motif" refers to a pattern of amino acids in a protein sequence that predicts binding to a particular MHC allele.

As used herein, the term "T-cell epitope cluster" refers to polypeptide that contains between about 4 to about 40 MHC binding motifs. In particular embodiments, the T-cell epitope cluster contains between about 5 to about 35 MHC binding motifs, between about 8 and about 30 MHC binding motifs; and between about 10 and 20 MHC binding motifs.

As used herein, the term "EpiBar" refers to a single 9-mer frame that is predicted to be reactive to at least four different HLA alleles. Sequences of known immunogens that contain EpiBars include Influenza Hemagglutinin 307-319, Tetanus Toxin 825-850, and GAD65 557-567. An example of an immunogenic peptide that contains an EpiBar is shown in FIG. 17. FIG. 17 depicts an example of an EpiBar and the EpiMatrix analysis of a promiscuous influenza epitope. Consider the influenza HA peptide, an epitope known to be promiscuously immunogenic. It scores extremely high for all eight alleles in EpiMatrix. Its cluster score is 18. Cluster scores higher than 10 are considered to be significant. The band-like EpiBar pattern is characteristic of promiscuous epitopes. Results are shown in FIG. 17 for PRYVKQNTL (SEQ ID NO:59), RYVKQNTLK (SEQ ID NO:60), YVKQNTLKL (SEQ ID NO:61), VKQNTLKLA (SEQ ID NO:62) and KQNTLKLAT (SEQ ID NO:63). Z score indicates the potential of a 9-mer frame to bind to a given HLA allele. All scores in the top 5% are considered "hits", while non hits (*) beow 10% are masked in FIG. 17 for simplicity.

As used herein, the term "Immune Synapse" means the protein complex formed by the simultaneous engagement of a given T cell Epitope to both a cell surface MHC complex and TCR.

As used herein, the term "regulatory T cell" means a subset of naturally occurring T cells characterized by the presence of certain cell surface markers including but not limited to CD4, CD25, and FoxP3. Upon activation regulatory T cells secrete immune suppressive cytokines and chemokines including but not limited to IL-10, TGF-β and TNF-α.

The term "polypeptide" refers to a polymer of amino acids, and not to a specific length; thus, peptides, oligopeptides and proteins are included within the definition of a polypeptide. As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be "isolated" or "purified." When a polypeptide is recombinantly produced, it can also be substantially free of culture medium, for example, culture medium represents less than about 20%, less than about 10%, or less than about 5% of the volume of the polypeptide preparation.

A variant polypeptide can differ in amino acid sequence by one or more substitutions, deletions, insertions, inversions, fusions, and truncations or a combination of any of these.

The invention also includes polypeptide fragments of the polypeptides of the invention. The invention also encompasses fragments of the variants of the polypeptides described herein. The invention also provides chimeric or fusion polypeptides. These comprise a polypeptide of the invention operatively linked to a heterologous protein or polypeptide having an amino acid sequence not substantially homologous to the polypeptide. "Operatively linked" indicates that the polypeptide and the heterologous protein are fused in-frame.

The isolated polypeptide can be purified from cells that naturally express it, purified from cells that have been altered to express it (recombinant), or synthesized using known protein synthesis methods. In one embodiment, the polypeptide is produced by recombinant DNA techniques. For example, a nucleic acid molecule encoding the polypeptide is cloned into an expression vector, the expression vector introduced into a host cell and the polypeptide expressed in the host cell. The polypeptide can then be isolated from the cells by an appropriate purification scheme using standard protein purification techniques.

For the purposes of the present invention, polypeptides can include, for example, modified forms of naturally occurring amino acids such as D-stereoisomers, non-naturally occurring amino acids; amino acid analogs; and mimetics.

Although any methods and materials similar or equivalent to those described herein can be used in the practice or testing of the present invention, the preferred methods and materials are described. Other features, objects, and advantages of the invention will be apparent from the description and the Claims. In the Specification and the appended Claims, the singular forms include plural referents unless the context clearly dictates otherwise. Unless defined otherwise, all technical and scientific terms used herein have the same meaning as commonly understood by one of ordinary skill in the art to which this invention belongs. All references cited herein are incorporated herein by reference in their entirety and for all purposes to the same extent as if each individual publication, patent, or patent application was specifically and individually indicated to be incorporated by reference in its entirety for all purposes.

Compositions

In one aspect, the invention provides a novel class of T cell epitopes compositions, termed 'Tregitopes', which comprise a peptide or polypeptide chain with one or more defined characteristics listed below. That is, the Tregitopes of the invention include, but are not limited to, possessing one or more of the following characteristics:

(1) Tregitopes of the invention are derived from common human proteins.

(2) Tregitopes of the invention are highly conserved among known variants of their source proteins (e.g., present in more than 50% of known variants).

(3) Tregitopes of the invention comprise at least one putative T cell epitope as identified by EpiMatrix analysis. EpiMatrix is a proprietary computer algorithm developed by EpiVax, which is used to screen protein sequences for the presence of putative T cell epitopes. Input sequences are parsed into overlapping 9-mer frames where each frame overlaps the last by 8 amino acids. Each of the resulting frames is then scored for predicted binding affinity with respect to a panel of eight common Class II HLA alleles (DRB1*0101, DRB1*0301, DRB1*0401, DRB1*0701, DRB1*0801, DRB1*1101, DRB1*1301, and DRB1*1501). Raw scores are normalized against the scores of a large sample of randomly generated peptides. The resulting "Z" score is reported. Any 9-mer peptide with an allele-specific EpiMatrix Z-score in excess of 1.64, theoretically the top 5% of any given sample, is considered a putative T cell epitope.

In a preferred embodiment the Tregitopes of the invention contain several putative T cell epitopes forming a pattern known as a T cell epitope cluster. Putative T-cell epitopes are not randomly distributed throughout protein sequences but instead tend to "cluster" in specific regions. In addition, peptides containing clusters of putative T cell epitopes are more likely to test positive in validating in vitro and in vivo assays. The results of the initial EpiMatrix analysis are further screened for the presence of putative T cell epitope "clusters" using a second proprietary algorithm known as Clustimer. The Clustimer algorithm identifies sub-regions contained within any given amino acid sequence that contains a statistically unusually high number of putative T cell epitopes. Typical T-cell epitope "clusters" range from about 9 to roughly 30 amino acids in length and, considering their affinity to multiple alleles and across multiple 9-mer frames, can contain anywhere from about 4 to about 40 putative T cell epitopes. For each epitope cluster identified an aggregate EpiMatrix score is calculated by summing the scores of the putative T cell epitopes and subtracting a correcting factor based on the length of the candidate epitope cluster and the expected score of a randomly generated cluster of the same length. EpiMatrix cluster scores in excess of +10 are considered significant.

Many of the most reactive T cell epitope clusters contain a feature referred to as an "EpiBar". An EpiBar is a single 9-mer frame that is predicted to be reactive to at least four different HLA alleles. Sequences that contain EpiBars include Influenza Hemagglutinin 307-319 (Cluster score of 18), Tetanus Toxin 825-850 (Cluster score of 16), and GAD65 557-567 (Cluster score of 19). In another embodiment, the peptides of the invention can comprise one or more EpiBars.

(4) Tregitopes of the invention bind to at least one and preferably two or more common HLA class II molecules with at least a moderate affinity (e.g., <200 µM $IC_{50}$ in HLA binding assays based on soluble HLA molecules).

(5) Tregitopes of the invention are capable of being presented at the cell surface by APCs in the context of at least one and, in a preferred embodiment, two or more alleles of the HLA.

(6) In this context, the Tregitope-HLA complex can be recognized by pre-existing populations of regulatory T cells having TCRs that are specific for the Tregitope-HLA complex and circulating in normal control subjects. The recognition of the Tregitope-HLA complex can cause the matching regulatory T cell to be activated and to secrete regulatory cytokines and chemokines.

(7) Stimulating regulatory T cells with Tregitope(s) of the invention results in increased secretion of one or more of the following cytokines and chemokines: IL-10, TGF-β, TNF-α and MCP1. This increased secretion of regulatory cytokines and chemokines is a hallmark of regulatory T cells.

(8) Regulatory T cells activated by the Tregitope(s) of the invention express a CD4+CD25+FOXP3 phenotype.

(9) Regulatory T cells activated by the Tregitope(s) directly suppress T-effector immune responses ex vivo as measured by decreased antigen-specific Th1- or Th2-associated cytokine levels, principally INF-γ, IL-4, and IL-5, and by decreased proliferation of antigen-specific T effector cells as measured by CFSE dilution.

(10) Regulatory T cells activated by the Tregitope(s) directly suppress T effector immune responses in vivo as measured by decreased antigen-specific Th1- or Th2-associated cytokine levels (as measured by Elisa assay), decreased antigen-specific T effector cell levels (as measured by EliSpot assay) and decreased antibody titers for protein antigens.

(11) Natural regulatory T cells activated by the Tregitopes of the invention stimulate the development of adaptive $T_{Reg}$ cells. Co-incubating peripheral T cells with the Tregitopes of the invention in the presence of antigen results in the expansion of antigen-specific CD4+/CD25+ T cells, upregulates the expression of FOXP3+ on those cells and suppresses the activation of antigen-specific T effector cells in vitro.

The Tregitopes of the invention are useful for regulating immune response to monoclonal antibodies, protein therapeutics, self antigens promoting autoimmune response, allergens, transplanted tissues and in other applications where tolerance is the desired outcome. Select embodiments of the Tregitopes of the invention are summarized in FIG. 18A and FIG. 18B in Example 1.

In one embodiment, the Tregitope of the invention is a T cell epitope isolated as described in FIG. 18A and FIG. 18B. The Tregitopes of FIG. 18A and FIG. 18B (SEQ ID NOs: 4 through 58) can bind MHC class II molecules, engage TCR in context of MHC class II molecules and activate natural regulatory T cells.

The polypeptides of the invention can be purified to homogeneity or partially purified. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (e.g., contaminating protein), less than about 20% other proteins, less than about 10% other proteins, or less than about 5% other proteins.

When a polypeptide is recombinantly produced, it can also be substantially free of culture medium, for example, culture medium represents less than about 20%, less than about 10%, or less than about 5% of the volume of the polypeptide preparation. The language "substantially free of chemical precursors or other chemicals" includes preparations of the polypeptide in which it is separated from chemical precursors or other chemicals that are involved in its synthesis. The language "substantially free of chemical precursors or other chemicals" can include, for example, preparations of the polypeptide having less than about 30% (by dry weight) chemical precursors or other chemicals, less than about 20% chemical precursors or other chemicals, less than about 10% chemical precursors or other chemicals, or less than about 5% chemical precursors or other chemicals.

As used herein, two polypeptides (or a region of the polypeptides) are substantially homologous or identical when the amino acid sequences are at least about 45-55%, typically at least about 70-75%, more typically at least about 80-85%, and more typically greater than about 90% or more homologous or identical. To determine the percent homology or identity of two amino acid sequences, or of two nucleic acid sequences, the sequences are aligned for optimal comparison purposes (e.g., gaps can be introduced in the sequence of one polypeptide or nucleic acid molecule for optimal alignment with the other polypeptide or nucleic acid molecule). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (e.g., percent homology equals the number of identical positions/total number of positions×100).

The invention also encompasses polypeptides having a lower degree of identity but having sufficient similarity so as to perform one or more of the same functions performed by a polypeptide encoded by a nucleic acid molecule of the invention. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent are found, for example, in Bowie, J. et al., *Science,* 247:1306-1310, 1990.

A variant polypeptide can differ in amino acid sequence by one or more substitutions, deletions, insertions, inversions, fusions, and truncations or a combination of any of these. Variant polypeptides can be fully functional or can lack function in one or more activities. Fully functional variants typically contain only conservative variation or variation in non-critical residues or in non-critical regions. Functional variants can also contain substitution of similar amino acids that result in no change or an insignificant change in function. Alternatively, such substitutions can positively or negatively affect function to some degree. Non-functional variants typically contain one or more non-conservative amino acid substitutions, deletions, insertions, inversions, or truncation or a substitution, insertion, inversion, or deletion in a critical residue or critical region. Several examples of variant polypeptides are included in FIG. 18A and FIG. 18B.

The invention also includes polypeptide fragments of the polypeptides of the invention. The invention also encompasses fragments of the variants of the polypeptides described herein. As used herein, a fragment comprises at least about five contiguous amino acids. Useful fragments include those that retain one or more of the biological activities of the polypeptide as well as fragments that can be used as an immunogen to generate polypeptide-specific antibodies. Biologically active fragments are, for example, about 6, 9, 12, 15, 16, 20 or 30 or more amino acids in length. Fragments can be discrete (not fused to other amino acids or polypeptides) or can be within a larger polypeptide. Several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The invention also provides chimeric or fusion polypeptides. These comprise a polypeptide of the invention operatively linked to a heterologous protein or polypeptide having an amino acid sequence not substantially homologous to the polypeptide. "Operatively linked" indicates that the polypeptide and the heterologous protein are fused in-frame. The heterologous protein can be fused to the N-terminus or C-terminus of the polypeptide. In one embodiment the fusion polypeptide does not affect function of the polypeptide per se. For example, the fusion polypeptide can be a GST-fusion polypeptide in which the polypeptide sequences are fused to the C-terminus of the GST sequences. Other types of fusion polypeptides include, but are not limited to, enzymatic fusion polypeptides, for example beta-galactosidase fusions, yeast two-hybrid GAL fusions, poly-His fusions and Ig fusions. Such fusion polypeptides, particularly poly-His fusions or affinity tag fusions, can facilitate the purification of recombinant polypeptide. In certain host cells (e.g., mammalian host cells), expression and/or secretion of a polypeptide can be increased by using a heterologous signal sequence. Therefore, in another embodiment, the fusion polypeptide contains a heterologous signal sequence at its N-terminus.

A chimeric or fusion polypeptide can be produced by standard recombinant DNA techniques. For example, DNA fragments coding for the different polypeptide sequences are ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers which give rise to complementary overhangs between two consecutive nucleic acid fragments which can subsequently be annealed and re-amplified to generate a chimeric nucleic acid sequence (Ausubel et al., Current Protocols in Molecular Biology, 1992). Moreover, many expression vectors are commercially available that already encode a fusion moiety (e.g., a GST protein). A nucleic acid molecule encoding a polypeptide of the invention can be cloned into such an expression vector such that the fusion moiety is linked in-frame to the polypeptide.

The isolated polypeptide can be purified from cells that naturally express it, purified from cells that have been altered to express it (recombinant), or synthesized using known protein synthesis methods. In one embodiment, the polypeptide is produced by recombinant DNA techniques. For example, a nucleic acid molecule encoding the polypeptide is cloned into an expression vector, the expression vector introduced into a host cell and the polypeptide expressed in the host cell. The polypeptide can then be isolated from the cells by an appropriate purification scheme using standard protein purification techniques.

The invention also provides for nucleic acids that encode in whole or in part the polypeptides of the invention. The nucleic acid molecules of the invention can be inserted into vectors and used, for example, as expression vectors or gene therapy vectors. Gene therapy vectors can be delivered to a subject by, e.g., intravenous injection, local administration (U.S. Pat. No. 5,328,470) or by stereotactic injection (Chen, et al., *Proc. Natl. Acad. Sci. USA*, 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

Tregitopes of the invention can include allelic or sequence variants ("mutants") or analogs thereof, or can include chemical modifications (e.g., pegylation, gycosylation). In one instance, a mutant can provide for enhanced binding to MHC molecules. In another instance, a mutant can lead to enhanced binding to TCRs. In an other instance, a mutant can lead to a decrease in binding to MHC molecules and/or TCRs. Also contemplated is a mutant that binds but does not allow signaling via the TCR.

The invention provides for Tregitope compositions that are chimeric protein compositions. In one embodiment, the Tregitope composition comprises a first and a second polypeptide chain linked together, wherein the first chain comprises sequence numbers 4 through 58 or any combination thereof, and said second chain comprises a biologically active molecule. In one embodiment, the biologically active molecule is selected from the group consisting of: an immunogenic molecule; a T cell epitope; viral protein; bacterial protein. In one embodiment, the Tregitope composition of the invention comprises a first and a second polypeptide chain linked together, wherein said first chain comprises a Fc region wherein the amino acids in region 289-309 has been altered so as not to bind to MHC class II molecules, and said second chain comprises a immunogenic molecule.

In one aspect, the invention provides methods to produce a regulatory T cell line recognizing at least a portion of SEQ ID NOS:4-58. In one embodiment, one or more peptides selected from the group consisting of SEQ ID NOS:4-58 are combined in admixture with an appropriate excipient. Such compositions are useful in methods of preventing or treating inflammation in a subject in need thereof, wherein local delivery of the admixture with an appropriate excipient results in decreased inflammation in the subject.

In one embodiment, one or more peptides selected from the group consisting of SEQ ID NOS:4-58 are combined in admixture with a antigen or allergen. Such compositions are useful in methods of inducing tolerance to the antigen or allergen in a subject in need thereof, wherein local delivery of the admixture with a antigen or allergen results in increased tolerance to the antigen or allergen in the subject, and delivered with an appropriate excipient resulting in induced tolerance to the antigen or allergen.

In one embodiment, the invention provides a nucleic acid encoding comprising one or more of the Tregitope polypeptides selected from the group consisting of SEQ ID NOS: 4-58. In one embodiment, the invention provides a vector comprising a nucleic acid encoding comprising one or more of the Tregitope polypeptides selected from the group consisting of SEQ ID NOS:4-58. In one embodiment, the invention provides a cell comprising a vector of the invention. The cell can be a mammalian cell, bacterial cell, insect cell, or yeast cell.

Cloning of Tregitope Specific T Cells

Cloning of Tregitope specific T cells can be conducted by techniques known to one of skill in the art. For example, isolated PBMCs are stimulated with Tregitopes at 10 µg/ml RPMI media containing 20% HSA. IL-2 is added (10 U/ml final concentration) every other day starting on day 5. T cells are stained with tetramer pools on day 11 or 12. For each pool, $2-3\times10^5$ cells are incubated with 0.5 mg of PE-labeled tetramer in 50 ml of culture medium (10 mg/ml) at 37° C. for 1 to 2 h, and then stained with anti-CD4-FITC (BD PharMingen, San Diego, Calif.) for 15 min at room temperature. Cells are washed and analyzed with a Becton Dickinson FACSCalibur flow cytometer (Becton Dickinson, San Jose, Calif.). Tetramers loaded with the corresponding single peptides are generated for those pools that give positive staining, and analysis is done on day 14 or 15. Cells that are positive for a particular tetramer are single-cell sorted into 96-well U-bottom plates by using a Becton Dickinson FACSVantage (San Jose, Calif.) on the same or following day. Sorted cells are expanded with $1.5-3\times10^5$ unmatched, irradiated (5000 rad) PBMC per well as feeders with 2.5 mg/ml PHA and 10 U/ml IL-2 added 24 h later. Specificity of cloned T cells is confirmed by staining with tetramers (loaded with cognate peptide or control peptide, HA307-319) and T cell proliferation assays with 10 mg/ml of specific peptide (Novak, E. et al., *J. Immunol.*, 166:6665-6670, 2001).

Methods of Use of Tregitope Compositions

In one aspect, the invention provides methods of using Tregitopes for the purpose of designing small molecules. In one method of the invention, Tregitope-specific T cells are stimulated three times with pools of small molecule mixtures at a concentration of 1 µg/ml and autologous dendritic cells (DC) at 2-week intervals, followed by stimulation with heterologous DC and antigens. T cells ($1.25\times10^5$) and DC ($0.25\times10^5$) are added per well in round-bottom, 96-well plates. T cell medium is made by supplementing 500 ml of RPMI medium 1640 with 50 ml of FCS (HyClone), penicillin, and streptomycin (GIBCO); 20 mM Hepes (GIBCO); and 4 ml 1 N NaOH solution. The IL-2 concentration is initially 0.1 nM and gradually is increased to 1 nM during subsequent rounds of stimulation. T cell clones are derived by limiting dilution by using $0.6\times10^5$ Epstein-Barr virus-transformed B cells (100 Gray) and $1.3\times10^5$ heterologous peripheral blood mononuclear cells (33 Gray) as feeder cells and 1 µg/ml phytohemagglutinin (Difco) in medium containing 2 nM IL-2. Small molecules pools that stimulate the Tregitope specific T cells are then tested as individual molecules.

In one aspect, the invention provides methods of using Tregitopes for the purpose of cloning T cell receptors. Total RNA is extracted with an RNeasy Mini Kit (Qiagene) from the Tregitope specific T cell lines generated as described above. One microgram of total RNA is used to clone the TCR cDNAs by a rapid amplification of cDNA end (RACE) method (GeneRacer Kit, Invitrogen). Before synthesizing the single-strand cDNA, the RNA is dephosphorylated, decapped, and ligated with an RNA oligonucleotide according to the instruction manual of 5' RACE GeneRacer Kit. SuperScript II RT and GeneRacer Oligo-dT are used for reverse transcription of the RNA Oligo-ligated mRNA to single-strand cDNAs. 5' RACE is performed by using GeneRacer 5' (GeneRacer Kit) as 5' primer and gene-specific primer TCRCAR (5'-GTT AAC TAG TTC AGC TGG ACC ACA GCC GCA GC-3'; SEQ ID NO:64) or TCRCB1R (5'-CGG GTT AAC TAG TTC AGA AAT CCT TTC TCT TGA CCA TGG C-3'; SEQ ID NO:65), or TCRCBR2 (5'-CTA GCC TCT GGA ATC CTT TCT CTT G-3'; SEQ ID NO:66) as 3' primers for TCR α, β1, or β2 chains, respectively. The polymerase chain reaction (PCR) products are cloned into pCR2.1 TOPO vector (Invitrogen) and then transformed into One Shot TOP10 Competent *Escherichia coli* (Invitrogen). Plasmid DNAs are prepared from 96 individual clones from each construct for TCRα, β1, and β2 chains. Full-length insert of all the plasmids is sequenced to determine the vα/vβ usage (Zhao, Y. et al., *J. Immunother.*, 29:398-406, 2006).

Pharmaceutical Formulations

The invention provides methods of treating a subject with a medical condition comprising administering a therapeutically effective amount of a Tregitope in a pharmaceutically acceptable carrier or excipient. The Tregitopes of the present invention can be incorporated into pharmaceutical compositions suitable for administration. The pharmaceutical compositions generally comprise at least one Tregitope and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the Tregitope compositions (see, e.g., Remington's Pharmaceutical Sciences, Mack Publishing Co., Easton, Pa. 18th ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. "Pharmaceutically-acceptable excipient" means, for example, an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. A person of ordinary skill in the art would be able to determine the appropriate timing, sequence and dosages of administration for particular drugs and compositions of the present invention.

Preferred examples of such carriers or diluents include, but are not limited to, water, saline, Ringer's solutions, dextrose solution, and 5% human serum albumin. Liposomes and non-aqueous vehicles such as fixed oils can also be used. The use of such media and compounds for pharmaceutically active substances is well known in the art. Except insofar as any conventional media or compound is incompatible with the Tregitope, use thereof in the compositions is contemplated. Supplementary active compounds can also be incorporated into the compositions.

A pharmaceutical composition of the invention is formulated to be compatible with its intended route of administration. The Tregitope compositions of the present invention can be administered by parenteral, topical, intravenous, oral, subcutaneous, intraarterial, intradermal, transdermal, rectal, intracranial, intraperitoneal, intranasal; vaginally; intramuscular route or as inhalants. In some embodiments of the invention, agents are injected directly into a particular tissue where deposits have accumulated, e.g., intracranial injection. Intramuscular injection or intravenous infusion are preferred for administration of the Tregitope. In some methods, particular Tregitopes of the invention are injected directly into the cranium. In some methods, the Tregitopes of the invention are administered as a sustained release composition or device, such as a Medipad™ device.

The Tregitope of the invention can optionally be administered in combination with other agents that are at least partly effective in treating various medical conditions as described herein. In the case of administration into the central nervous system of a subject, the Tregitope of the invention can also be administered in conjunction with other agents that increase passage of the agents of the invention across the blood-brain barrier.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. Examples of excipients can include starch, glucose, lactose, sucrose, gelatin, malt, rice, flour, chalk, silica gel, water, ethanol, DMSO, glycol, propylene, dried skim milk, and the like. The composition can also contain pH buffering reagents, and wetting or emulsifying agents.

The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition is sterile and should be fluid to the extent that easy syringeability exists. It is stable under the conditions of manufacture and storage and is preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, sodium chloride in the composition. Prolonged absorption of the injectable compositions can be brought about by including in the composition a compound that delays absorption, e.g., aluminum monostearate and gelatin.

Sterile injectable solutions can be prepared by incorporating the Tregitope in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation that can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel or corn starch; a lubricant such as magnesium stearate or Sterotes; a glidant such as colloidal silicon dioxide; a sweetening compound such as sucrose or saccharin; or a flavoring compound such as peppermint, methyl salicylate or orange flavoring.

For administration by inhalation, the Tregitope(s) are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the Tregitope is formulated into ointments, salves, gels, or creams and applied either topically or through transdermal patch technology as generally known in the art.

The Tregitope can also be prepared as pharmaceutical compositions in the form of suppositories (e.g., with conventional suppository bases such as cocoa butter and other glycerides) or retention enemas for rectal delivery.

In one embodiment, the Tregitope is prepared with carriers that protect the Tregitope against rapid elimination from the body, such as a controlled-release formulation, including implants and microencapsulated delivery systems. Biodegradable, biocompatible polymers can be used, such as, for example, ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art (U.S. Pat. No. 4,522,811). The Tregitopes or chimeric proteins can be implanted within or linked to a biopolymer solid support that allows for the slow release of the Tregitopes or chimeric proteins to the desired site.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of binding agent calculated to produce the desired therapeutic effect in association with the required pharmaceutical carrier. The specification for the dosage unit forms of the invention are dictated by and directly dependent on the unique characteristics of the binding agent and the particular therapeutic effect to be achieved, and the limitations inherent in the art of compounding such Tregitope for the treatment of a subject.

Methods of Preventing or Treating a Medical Condition

The present invention is directed to, for example methods of treating one or more medical conditions comprising administering a Tregitope or chimeric protein of the invention, thereby treating the medical condition. The medical condition can be, for example, primary immunodeficiencies; immune-mediated thrombocytopenia, Kawasaki disease, hematopoietic stem cell transplantation in patients older than 20 years, chronic B-cell lymphocytic leukemia and pediatric HIV type 1 infections. Specific examples include: (Hematology) aplastic anemia, pure red cell aplasia, Diamond-Blackfan anemia, autoimmune hemolytic anemia, hemolytic disease of the newborn, acquired factor VIII inhibitors, acquired von Willebrand disease, immune-mediated neutropenia, refractoriness to platelet transfusion, neonatal alloimmune/autoimmune thrombocytopenia, posttransfusion purpura, thrombotic thrombocytopenia purpura/hemolytic uremic syndrome; (Infectious diseases) conditions in which acquiring an infectious disease could be deleterious include low birth weight (e.g., <1500 g), solid organ transplantation, surgery, trauma, burns, and HIV infection; (Neurology) epilepsy and pediatric intractable Guillain-Barré syndrome, chronic inflammatory demyelinating polyneuropathy, myasthenia gravis, Lambert-Eaton myasthenic syndrome, multifocal motor neuropathy, multiple sclerosis; (Obstetrics) recurrent pregnancy loss; (Pulmonology) asthma, chronic chest symptoms, rheumatology, rheumatoid arthritis (adult and juvenile), systemic lupus erythematosus, systemic vasculitides, dermatomyositis, polymyositis, inclusion-body myositis, wegener granulomatosis; (Miscellaneous) adrenoleukodystrophy, amyotrophic lateral sclerosis, Behçet syndrome, acute cardiomyopathy, chronic fatigue syndrome, congential heart block, cystic fibrosis, autoimmune blistering dermatosis, diabetes mellitus, acute idiopathic dysautonomia, acute disseminated encephalomyelitis, endotoxemia, hemolytic transfusion reaction, hemophagocytic syndrome, acute lymphoblastic leukemia, lower motor neuron syndrome, multiple myeloma, human T-cell lymphotrophic virus-1-associated myelopathy, nephritic syndrome, membranous nephropathy, nephrotic syndrome, euthyroid ophthalmopathy, opsoclonus-myoclonus, recurrent otitis media, paraneoplastic cerebellar degeneration, paraproteinemic neuropathy, parvovirus infection (general), polyneuropathy, organomegaly, endocrinopathy, M-protein, and skin changes (POEMS) syndrome, progressive lumbosacral plexopathy, lyme radiculoneuritis, Rasmussen syndrome, Reiter syndrome, acute renal failure, thrombocytopenia (nonimmune), streptococcal toxic shock syndrome, uveitis and Vogt-Koyanagi-Harada syndrome.

In particular embodiment, the present invention is directed to, for example, methods of treating allergy, autoimmune disease, transplant-related disorders such as graft versus host disease, enzyme or protein deficiency disorders, hemostatic disorders, cancers, infertility, or infections (viral, bacterial, or parasitic). The Tregitopes or chimeric proteins of the invention can be used with in conjunction with other proteins or compounds used for treating a subject with a medical condition in order to reduce adverse events or enhance the efficacy of the co-administered compound.

Application to Allergy

Allergen-specific regulatory T cells play an important role in controlling the development of allergy and asthma. Both naturally occurring CD4/CD25 regulatory T cells and secondary $T_{Regs}$ (antigen-specific regulatory T cells), both expressing the transcription factor FOXp3, have been shown to inhibit the inappropriate immune responses involved in allergic diseases. A number of recent studies indicate that regulatory T cells play an important role in controlling the overdevelopment of T-helper type 2 biased immune responses in susceptible individuals, not only in animal models, but in humans as well. Recent studies indicate that T regulatory cells also suppress T cell costimulation by the secretion of TGF-β and IL-10, suggesting an important role of T regulatory cells in the regulation of allergic disorders. Impaired expansion of natural or adaptive regulatory T cells leads to the development of allergy, and treatment to induce allergen-specific regulatory T cells would provide curative therapies for allergy and asthma.

One strategy both for the prevention and therapy of asthma is the induction of regulatory T cells. Animals can be protected from developing asthma by immune stimulation leading to Th1 or Tr responses.

Application to Transplantation

The Tregitopes of the invention are useful to induce tolerance during the transplantation process, by promoting the development of cells that specifically down regulate immune responses against donor cells. Induction of Ag-specific $T_{Reg}$ cells for treating organ-specific autoimmunity is an important therapeutic development, avoiding generalized immune suppression. In murine models of bone marrow transplantation, $T_{Regs}$ promote donor bone marrow engraftment and decrease the incidence and severity of graft versus host disease without abrogating the beneficial graft versus tumor immunologic effect. These findings, in concert with observations that $T_{Regs}$ in mice and humans share phenotypic and functional characteristics, have led to active investigations into the use of these cells to decrease complications associated with human hematopoietic cell transplantation. An imbalance of $T_{Regs}$ and effector T cells contributes to the development of graft versus host disease. However, the mechanisms of immunoregulation, in particular the allorecognition properties of $T_{Regs}$, their effects on and interaction with other immune cells, and their sites of suppressive activity, are not well understood.

Accumulating evidence from both humans and experimental animal models has implicated the involvement of $T_{Regs}$ in the development of graft versus host disease (GVHD). The demonstration that $T_{Regs}$ can separate GVHD from graft versus tumor (GVT) activity suggests that their immunosuppressive potential could be manipulated to reduce GVHD without detrimental consequence on GVT effect. Although a variety of T lymphocytes with suppressive capabilities have been reported, the two best-characterized subsets are the naturally arising, intrathymic-generated $T_{Regs}$ (natural $T_{Regs}$) and the peripherally generated, inducible $T_{Regs}$ (inducible $T_{Regs}$).

Application to Autoimmunity

Tregitopes can be used as a tolerizing agents for immunogenic compounds (protein therapeutics). This discovery has implications for the design of protein therapeutics. Thus, administration of a monoclonal antibody, autologous cytokine, or foreign protein in conjunction with Tregitopes suppresses adverse T effector immune responses. In vivo, $T_{Regs}$ act through dendritic cells to limit autoreactive T-cell activation, thus preventing their differentiation and acquisition of effector functions. By limiting the supply of activated pathogenic cells, $T_{Regs}$ prevent or slow down the progression of autoimmune diseases. This protective mechanism appears, however, insufficient in autoimmune individuals, likely because of a shortage of $T_{Regs}$ cells and/or the development and accumulation of $T_{Reg}$-resistant pathogenic T cells over the long disease course. Thus, restoration of self-tolerance in these patients may require purging of pathogenic T cells along with infusion of $T_{Regs}$ with increased ability to control ongoing tissue injury. Organ-specific autoimmune conditions, such as thyroiditis and insulin-dependent diabetes mellitus have been attributed to a breakdown of this tolerance mechanism.

Application to Diabetes

Type 1 (juvenile) diabetes is an organ-specific autoimmune disease resulting from destruction of insulin-producing pancreatic beta-cells. In non-diabetics, islet cell antigen-specific T cells are either deleted in thymic development or are converted to T regulatory cells that actively suppress effector responses to islet cell antigens. In juvenile diabetics and in the NOD mouse model of juvenile diabetes, these tolerance mechanisms are missing. In their absence, islet cell antigens are presented by human leukocyte antigen (HLA) class I and II molecules and are recognized by CD8(+) and CD4(+) auto-reactive T cells. Destruction of islet cells by these auto-reactive cells eventually leads to glucose intolerance. Co-administration of Tregitopes and islet cell antigens leads to the activation of natural T regulatory cells and the conversion of existing antigen specific effector T cell to a regulatory phenotype. In this way deleterious autoimmune response is redirected leading to the induction of antigen-specific adaptive tolerance. Modulation of auto-immune responses to autologous epitopes by induction of antigen-specific tolerance can prevent ongoing beta-cell destruction. Accordingly, a Tregitope of the invention is useful in methods for the prevention or treatment of diabetes.

Application to Hepatitus B (HBV) Infection

Chronic HBV is usually either acquired (by maternal fetal transmission) or can be a rare outcome of acute HBV infection in adults. Acute exacerbations of chronic hepatitis B (CH-B) are accompanied by increased cytotoxic T cell responses to hepatitis B core and e antigens (HBcAg/HBeAg). In a recent study, the SYFPEITHI T cell epitope mapping system was used to predict MHC class II-restricted epitope peptides from the HBcAg and HbeAg. MHC class II tetramers using the high scoring peptides were constructed and used to measure $T_{Reg}$ and CTL frequencies. The results showed that $T_{Reg}$ cells specific for HBcAg declined during exacerbations accompanied by an increase in HBcAg peptide-specific cytotoxic T cells. During the tolerance phase, FOXp3-expressing $T_{Reg}$ cell clones were identified. These data suggest that the decline of HbcAg $T_{Reg}$ T cells accounts for the spontaneous exacerbations on the natural history of chronic hepatitis B virus infection. Accordingly, a Tregitope of the invention is useful in methods for the prevention or treatment of viral infection, e.g., HBV infection.

Application to SLE

A TReg epitope that plays a role in Systemic Lupus Erythematosis (SLE) or Sjögren's syndrome has been defined. This peptide encompasses residues 131-151 (RIHMVYSKRSGKPRGYAFIEY; SEQ ID NO:67) of the spliceosome protein. Binding assays with soluble HLA class II molecules and molecular modeling experiments indicated that the epitope behaves as promiscuous epitope and binds to a large panel of human DR molecules. In contrast to normal T cells and T cells from non-lupus autoimmune patients, PBMCs from 40% of randomly selected lupus patients contain T cells that proliferate in response to peptide 131-151. Alteration of the ligand modified the T cell response, suggesting that several populations of T cells responding to this peptide exist, among which may be TReg cells. T regulatory epitopes have also been defined in Sjögren's syndrome. Accordingly, a Tregitope of the invention co-administered in combination with the epitope from above is useful in methods for the prevention or treatment of SLE.

Application to Graves' Disease

Graves' disease is an autoimmune disorder that is characterized by antibodies to self-thyroid stimulating hormone receptor (TSHR) leading to leading to hyperthyroidism, or an abnormally strong release of hormones from the thyroid gland. Several genetic factors can influence susceptibility to Graves' disease. Females are much more likely to contract the disease than males; White and Asian populations are at higher risk than black populations and HLA DRB1-0301 is closely associated with the disease. Accordingly, co-administration of Tregitope(s) of the invention with TSHR or other Graves' disease antigens or portions thereof is useful in methods for the prevention or treatment of Graves' disease.

Application to Autoimmune Thyroiditis

Autoimmune Thyroiditis is a condition that occurs when antibodies arise to self thyroid peroxidase and/or thyroglobulin, which cause the gradual destruction of follicles in the thyroid gland. HLA DR5 is closely associated with the disease. Accordingly, co-administration of Tregitope of the invention with thyroid peroxidase and/or thyroglobulin TSHR or portions thereof are useful in methods for the prevention or treatment of autoimmune thyroiditis.

Application to the Design of Vaccine Vectors

A monoclonal antibody targeting the dendritic cell surface receptor DEC-205 has shown promise as a vaccine vector capable of targeting vaccine antigens to dendritic cells. The success of anti-DEC-205 as a stimulator of strong inflammatory immune responses, however, depends on co-administration of non-specific dendritic cell maturation factors. In their absence, anti-DEC-205 induces antigen-specific tolerance rather than immunity. Therefore, regulatory T-cell epitopes contained in anti-DEC-205 promote a tolerogenic reaction that is only overcome through the co-administration of non-specific immuno-stimulators. This point has been verified experimentally, namely, that the Tregitopes contained in the anti-DEC-205 vector cause antigen-specific expansion of regulatory T cells and suppress inflammatory immune responses. Modifying those Tregitopes such that they no longer bind to MHC molecules will significantly diminish tolerogenicity, enabling use of anti-DEC-205 as an effective stand alone antigen delivery system that obviates the dangers associated with non-specific activation of the immune system.

Kits

The methods described herein can be performed, e.g., by utilizing pre-packaged kits comprising at least one Tregitope composition of the invention, which can be conveniently used, e.g., in clinical settings to treat subjects exhibiting symptoms or family history of a medical condition described herein. In one embodiment, the kit further comprises instructions for use of the at least one Tregitope composition of the invention to treat subjects exhibiting symptoms or family history of a medical condition described herein.

Ex Vivo Expansion of T-Regulatory Cells Using Tregitopes

In another aspect, the invention provides ex vivo methods for the expansion of regulatory T-cells. In one embodiment, the invention provides a method of expanding regulatory T-cells in a biological sample, the method comprising: (a) providing a biological sample from a subject; (b) isolating regulatory T-cells from the biological sample; and contacting the isolated regulatory T-cells with an effective amount of a Tregitope composition of the invention under conditions wherein the T-regulatory cells increase in number to yield an expanded regulatory T-cell composition, thereby expanding the regulatory T-cells in the biological sample. In one embodiment, the method further comprises the step of administration of the expanded regulatory T-cell composition to a subject. In one embodiment, the subject administered the expanded regulatory T-cell composition is the same individual from which the original biological sample was obtained, e.g., by autologous transplantation of the expanded regulatory T-cell composition (Ruitenberg, J. et al., *BMC Immunol.*, 7:11, 2006).

In Vitro Uses of Tregitope Compositions

In another aspect, the invention provides the use of the Tregitope compositions of the invention as reagents in the study of regulatory T-cell function in in vitro experimental models. In one embodiment, the invention provides in vitro methods for stimulation of regulatory T-cells in a biological sample, the method comprising: (a) providing a biological sample from a subject; (b) isolating regulatory T-cells from the biological sample; and contacting the isolated regulatory T-cells with an effective amount of a Tregitope composition of the invention under conditions wherein the T-regulatory cells are stimulated to alter one or more biological function, thereby stimulating the regulatory T-cells in the biological sample. In one embodiment, the invention provides in vitro methods for the measurement of binding Tregitope to a regulatory T-cells or fragment thereof.

The examples that follow are not to be construed as limiting the scope of the invention in any manner. In light of the present disclosure, numerous embodiments within the scope of the claims will be apparent to those of ordinary skill in the art.

Exemplification

Tregitopes were (1) identified using the T cell epitope mapping algorithm EpiMatrix, (2) confirmed to bind to soluble HLA, (3) proven to engage natural regulatory T cells, (4) proven to suppress the immune response to co-delivered antigens ex vivo (in human PBMC) and (3) proven to suppress the immune response to co-delivered antigens in vivo (in mice). The methods for these discoveries are outlined below followed by the corresponding results.

(1) Methods for the Identification of T Cell Epitopes and T Cell Epitope Clusters T cells specifically recognize epitopes presented by antigen presenting cells (APCs) in the context of MHC (Major Histocompatibility Complex) Class II molecules. These T-helper epitopes can be represented as linear sequences comprising 7 to 30 contiguous amino acids that fit into the MHC Class II binding groove. A number of computer algorithms have been developed and used for detecting Class II epitopes within protein molecules of various origins (De Groot, A. et al., *AIDS Res. Hum. Retroviruses*, 13: 539-541, 1997; Schafer, J. et al., *Vaccine*, 16:1880-1884, 1998; De Groot, A. et al., *Vaccine*, 19:4385-95, 2001; De Groot, A. et al., *Vaccine*, 21:4486-504, 2003). These "in silico" predictions of T-helper epitopes have been successfully applied to the design of vaccines and the deimmunization of therapeutic proteins.

The EpiMatrix system is a tool for predicting class I and class II epitopes. The algorithm uses matrices for prediction of 9- and 10-mer peptides binding to HLA molecules. Each matrix is based on position-specific coefficients related to amino acid binding affinities that are elucidated by a method similar to, but not identical to, the pocket profile method (Sturniolo, T. et al., *Nat. Biotechnol.*, 17:555-561, 1999). The EpiMatrix system has been used to prospectively predict a large number of epitopes that have been confirmed in vitro and in vivo. The entire amino acid of any given sequence is first parsed into overlapping 9-mer frames where each frame overlaps the last by eight amino acids. Each frame is then scored for predicted affinity to each of eight common Class II HLA haplotypes (DRB1*0101, DRB1*0301, DRB1*0401, DRB1*0701, DRB1*0801, DRB1*1101, DRB1*1301, and DRB1*1501). Due to their prevalence and their difference from each other, these eight alleles cover around 97% of human populations worldwide. EpiMatrix raw scores are then normalized with respect to a score distribution derived from a very large set of randomly generated peptide sequences. The resulting "Z" scores are normally distributed and directly comparable across alleles.

EpiMatrix Peptide Scoring

It was determined that any peptide scoring above 1.64 on the EpiMatrix "Z" scale (approximately the top 5% of any given peptide set) has a significant chance of binding to the MHC molecule for which it was predicted. Peptides scoring above 2.32 on the scale (the top 1%) are extremely likely to bind; most published T cell epitopes fall within this range of scores. Previous studies have also demonstrated that EpiMatrix accurately predicts published MHC ligands and T cell epitopes.

Identification of Promiscuous T Cell Epitope Clusters

Following epitope mapping, the result set produced by the EpiMatrix algorithm is screened for the presence of T cell epitope clusters and EpiBars. Potential T cell epitopes are not randomly distributed throughout protein sequences but instead tend to "cluster." T cell epitope "clusters" range from 9 to roughly 30 amino acids in length and, considering their affinity to multiple alleles and across multiple frames, contain anywhere from 4 to 40 binding motifs. Using a proprietary algorithm know as ClustiMer, putative T cell epitope clusters are identified. Briefly, the EpiMatrix scores of each 9-mer peptide analyzed are aggregated and checked against a statistically derived threshold value. High scoring 9-mers are then extended one amino acid at a time. The scores of the extended sequences are then re-aggregated and compared to a revised threshold value. The process is repeated until the proposed extension no longer improves the overall score of the cluster. Tregitope(s) identified in the present studies were identified by the ClustiMer algorithm as T cell epitope clusters. They contain significant numbers of putative T cell epitopes and EpiBars indicating a high potential for MHC binding and T cell reactivity.

(2) Methods for the Assessment of Peptide Synthesis and Binding to Soluble MHC

Synthesis of Peptides

Tregitopes can be produced by direct chemical synthesis or by recombinant methods (Sambrook et al., Molecular Cloning: A Laboratory Manual, 2 ed., Cold Spring Harbor Laboratory Press, (1989)). Peptides corresponding to the Tregitopes of the invention were prepared by 9-fluoronyl-methoxycarbonyl (Fmoc) synthesis at New England peptide and on an automated Rainen Symphony/Protein Technologies synthesizer (Synpep, Dublin, Calif.). The peptides were delivered >80% pure as ascertained by HPLC, mass spectrometry and UV scan (ensuring purity, mass and spectrum, respectively).

Binding of Produced Peptides

Non-biotinylated test peptide is suspended in a 96-well polypropylene plate in final concentrations ranging from 0.1 µM-400 µM in triplicate wells. Purified recombinant HLA Class II molecules in a solution containing 1 mM PefaBloc, 0.75% n-octyl-B-D-glucopyranoside in 150 mM citrate-phosphate buffer (pH 5.4), were then added to these wells at a final concentration of 200 ng/well. The 96-well plates are incubated at 37° C. in 6% $CO_2$ for 45 minutes. Following the incubation, biotinylated Flu HA peptide 307-319 (or another suitable control peptide) is added to a final concentration of 0.1 µM per well and incubated at 37° C. for 20 hours. The contents of each well are then added to a 96-well high binding ELISA plate previously coated with the anti-human HLA-DR L243 capture antibody (Becton Dickenson) and incubated at 4° C. for 20 hours. The plate was then developed by the addition of 100 µl (10 µg/ml) of Europium-labeled Streptavidin (Perkin-Elmer) and 100 µl Enhancement Buffer (Perkin-Elmer) to each well. The reaction was incubated in the dark at room temperature for 15-30 minutes and then fluorescence was measured on a Wallac Victor 3-V time-resolved fluourometer. $IC_{50}$ values were then calculated by non-linear regression analysis using the SigmaPlot analysis program. Based on comparisons with known peptides, an $IC_{50}$ of 250 µM or more is indicative of weak binding and an $IC_{50}$ of 400 µM or more is indicative of a non-binding interaction.

(3) Methods for Assessing the Ability of Peptides to Engage Natural Regulatory T Cells T-Cell Isolation This research program involves donated blood obtained from the Rhode Island Blood Bank in Providence, blood from volunteers recruited at Clinical Partners, Johnston, R.I., blood obtained from volunteers recruited by Stallergenes, Paris, France, and samples obtained from a commercial supplier. Donor blood was obtained in accordance with all federal guidelines and in accordance with Stallergenes and EpiVax institutional policies. The protocol for obtaining donor blood was approved by the respective institutional review boards. Peripheral blood mononuclear cells (PBMC) were isolated according to the Accuspin protocol (Sigma-Aldrich, St. Louis, Mo.). Cryopreserved PBMC from dust-mite-allergic individuals were obtained from Cellular Technologies Ltd. (Cleveland, Ohio).

Natural T Reg Assay

Human PBMCS are stimulated directly ex vivo for 4 days in the presence of tetanus toxin peptide $TT_{830-844}$ alone, Tregitope alone, phytohemagglutinin alone (a mitogenic positive control) or no stimulus. $1 \times 10^6$ cells were stained with anti-CD4-FITC (clone RPA-T4; eBioscience) and anti-CD25-APC (clone BC96; eBioscience) antibodies for 30 minutes on ice in Flow Staining Buffer (eBioscience) and washed twice with buffer. Following cell surface staining, cells are fixed and permeabilized (eBioscience) and stained intracellulary for FOXp3 (clone PCH101; eBioscience) following manufacturer's protocol. The frequency of FOXp3 positive CD4+/CD25+ T cells under various culture conditions is enumerated by the Flowjo analysis software. T cell activation is indicated by increases in CD4+CD25+ expression, which, when accompanied by an increase in FOXp3 expression, is indicative that the activated cells are regulatory.

(4) Methods for Assessing the Ability of Peptides to Suppress the Response to Co-Administered Antigens Ex Vivo Bystander Suppression Assay Isolated PBMCs were cultured for 8 days at 37° C. 5% $CO_2$ in presence of either an immunogenic antigen alone or that antigen in the presence of Tregitope peptide. Test antigens were added at 10 µg/ml and include 1) classic antigens such as, for example, tetanus toxin peptide $TT_{830-844}$, influenza hemagglutinin peptide 307-319, vaccinia peptide epitopes and the CEF positive control peptide pool (NIH AIDS Research & Reference Reagent Program at the website aidsreagent.org; Currier, J. et al., *J. Immunol. Methods*, 260:157-72, 2002; Mwau, M. et al., *AIDS Res. Hum. Retroviruses*, 18:611-8, 2002), 2) protein therapeutics such as Botulinum Neurotoxin A, autologous autoantigens such as Thyroid Hormone Stimulating hormone and complement component C3d. Test antigens also included allergens: birch tree pollen antigen Betv1, House dust mite lysate and the purified house dust mite antigen, Der P2. Recombinant IL-2 (10 IU/ml) and IL-7 (20 ng/ml) were added to PBMC cultures on day 2. After 8 days of stimulation, cells were harvested and washed several times with PBS and assayed according to the human cytokine release assays described below.

Human IFN-γ ELISpot

IFN-γ ELISpot assays are performed using Human IFN-γ ELISpot kits purchased from Mabtech. Target peptides are added at 10 µg/ml to triplicate wells containing 250,000 human peripheral blood mononuclear cells in RPMI1640 with 10% human serum and incubated for eighteen to twenty-two hours at 37° C. under a 5% $CO_2$ atmosphere. Triplicate wells are plated with PHA at 10 µg/mL. Six wells with no peptide are used for background determination. A response is considered positive if the number of spots in the peptide test wells is statistically different (p<0.05) from that of the control wells by the Mann-Whitney U test. In general, responses are considered positive if the number of spots is at least four times background and greater than 50 spots per one million cells over background (1 response over background per 20,000 splenocytes). Results are recorded as the average number of spots over background and adjusted to spots per one million cells seeded. Suppression rates of 10% or greater, when determined to be statistically significant, are considered statistically significant.

Human IFN-γ ELISpot

IFN-γ ELISpot assays are performed using Human IL-4 ELISpot kits purchased from Mabtech. Target peptides are added at 10 µg/ml to triplicate wells containing 250,000 human peripheral blood mononuclear cells in RPMI1640 with 10% human serum and incubated for eighteen to twenty-two hours at 37° C. under a 5% $CO_2$ atmosphere. Triplicate wells are plated with PHA at 10 µg/mL. Six wells with no peptide are used for background determination. A response is considered positive if the number of spots in the peptide test wells is statistically different (p<0.05) from that of the control wells by the Mann-Whitney U test. In general, responses are considered positive if the number of spots is at least four times background and greater than 50 spots per one million cells over background (1 response over background per 20,000 splenocytes). Results are recorded as the average number of spots over background and adjusted to spots per one million cells seeded. Suppression rates of 10% or greater, when determined to be statistically significant, are considered statistically significant.

Human IL-4 ELISpot

IL-4 ELISpot assays are performed using Human IL-4 ELISpot kits purchased from Mabtech. Target peptides are added at 10 µg/ml to triplicate wells containing 250,000 human peripheral blood mononuclear cells in RPMI1640 with 10% human serum and incubated for eighteen to twenty-two hours at 37° C. under a 5% $CO_2$ atmosphere. Triplicate wells are plated with PHA at 2 µg/mL. Six wells with no peptide are used for background determination. Statistical tests were carried out using a variant permutation test (Hudgens, M. et al., *J. Immunol. Methods*, 288:19-34, 2004). A response is considered positive if the number of spots in the peptide test wells is statistically different (p<0.01) from that of the control wells. In general, responses are considered positive if the number of spots is at least four times background and greater than 50 spots per one million cells over background (1 response over background per 20,000 splenocytes). Results are recorded as the average number of spots over background and adjusted to spots per one million cells seeded. Suppression rates of 10% or greater, when determined to be statistically significant, are considered significant.

Human IFN-γ ELISA

Target peptides are added at 10 µg/ml to cultures containing human peripheral blood mononuclear cells in RPMI1640 with 10% human serum and incubated for eighteen to twenty-two hours at 37° C. under a 5% $CO_2$ atmosphere. Cultures stimulated with PHA at 10 µg/mL or with no peptide are used as controls. Human IFN-γ quantitative sandwich ELISAs were performed using R&D Systems Quantikine ELISA kits. A polyclonal antibody specific for IFN-γ is pre-coated onto a 96-well microtiter plate. Kit-provided standards and cell supernatant samples including PHA and no-peptide controls (100 µl) are pipetted into the wells and any IFN-γ present is bound by the immobilized antibody over 2 hours at room temperature. After washing away unbound substances, an enzyme-linked polyclonal antibody specific for IFN-γ is added to the wells for a two hour incubation at room temperature. Following a wash to remove any unbound antibody-enzyme reagent, a substrate solution is added to the wells for 30 minutes and color developed in proportion to the amount of bound IFN-γ. The color development is stopped and the intensity of the color at 450 nm measured on a Wallac Victor3. Correction for optical imperfections in the plate is made by subtraction of intensities at 540 nm from the 450 nm values. Differences in cytokine levels between experimental groups were evaluated by t-test. A response is considered positive if the observed difference in cytokine expression between the experimental and control wells is statistically different (p<0.01).

Multiplexed Human Cytokine/Chemokine ELISA

Supernatants from PBMC cultures are evaluated for cytokines and chemokine levels using the SearchLight multiplex ELISA technology. Human cytokines that are measured include IL-1β, IL-2, IL-4, IL-5, IL-6, IL-10, IL-12p70, IL-12p70, TNFα and TGFβ. Human chemokines that are measured include MCP-1, MIP-1α and MIP-1β. Search-Light☐ Proteomic Arrays are a quantitative multiplexed sandwich ELISA containing up to 16 different capture antibodies spotted on the bottom of a 96-well polystyrene microtiter plate. Each antibody captures specific protein detected with a biotinylated antibody, followed by the addition of streptavidin-HRP and lastly, SuperSignal ELISA Femto Chemiluminescent substrate detected with a charge-coupled device (CCD) camera. Differences in cytokine levels between experimental groups were evaluated by t-test. A response is considered positive if the observed difference in cytokine expression between the experimental and control wells is statistically different (p<0.01).

Cell Separations/Depletions Methods

Human Treg cell populations are depleted or positively isolated from PBMC using the invitrogen dynabeads system (for human CD4 and CD25) according to manufacturer's instructions (InVitrogen, Carlsbad, Calif.).

(5) Methods for the Suppression of Response to Co-Administered Antigens In Vivo To measure the immunosuppressive effects of Tregitopes on protein-induced effector responses in a living system, experiments are performed using a murine model. Groups of mice are immunized with an antigen alone, a cocktail of antigen and tregitope, or with an antigen fused to tregitope. A negative control group (solvent alone) is also assessed. One week following the final injection, the mice are sacrificed in accordance with all institutional and federal guidelines and spleens harvested. Freshly isolated mouse splenocytes are used to assay the cellular immune response in vivo. Single splenocyte suspensions are prepared and used in the assays below. Whole blood is also obtained by cardiac puncture and serum collected for use in quantifying antibody response to the co-administered antigen.

Murine IFN-γ ELISpot

IFN-γ ELISpot assays are performed using murine IFN-γ ELISpot kits purchased from Mabtech. Target peptides are added at 10 µg/ml to tripliocate wells containing 300,000 murine splenocytes (in RPMI1640 with 10% FCS) and incubated for eighteen to twenty-two hours at 37° C. under a 5% $CO_2$ atmosphere. Triplicate wells are plated with ConA at 10 µg/mL. Six wells with no peptide are used for background determination. A response is considered positive if the number of spots in the peptide test wells is statistically different (p<0.05) from that of the control wells by the Mann-Whitney U test. In general, responses are considered positive if the number of spots is at least four times background and greater than 50 spots per one million cells over background (1 response over background per 20,000 splenocytes). Results are recorded as the average number of spots over background and adjusted to spots per one million cells seeded.

Murine IL-4 ELISpot

IL-4 ELISpot assays are performed using murine IL-4 ELISpot kits purchased from Mabtech. Target peptides are added at 10 µg/ml to triplicate wells containing 300,000 murine splenocytes (in RPMI1640 with 10% FCS) and incubated for eighteen to twenty-two hours at 37° C. under a 5% $CO_2$ atmosphere. Triplicate wells are plated with ConA at 10 µg/mL. Six wells with no peptide are used for background determination. Statistical tests were carried out using a variant permutation test (Hudgens, M. et al., *J. Immunol. Methods*, 288:19-34, 2004). A response is considered positive if the number of spots in the peptide test wells is statistically different ($p<0.01$) from that of the control wells. In general, responses are considered positive if the number of spots is at least four times background and greater than 50 spots per one million cells over background (1 response over background per 20,000 splenocytes). Results are recorded as the average number of spots over background and adjusted to spots per one million cells seeded.

Murine IFN-γ ELISA

Target peptides are added at 10 µg/ml to cultures containing human peripheral blood mononuclear cells in RPMI1640 with 10% human serum and incubated for eighteen to twenty-two hours at 37° C. under a 5% $CO_2$ atmosphere. Cultures stimulated with PHA at 10 µg/mL or with no peptide are used as controls. Mouse IFN-γ quantitative sandwich ELISAs were performed using R&D Systems Quantikine ELISA kits. A polyclonal antibody specific for IFN-γ is pre-coated onto a 96-well microtiter plate. Kit-provided standards and cell supernatant samples including PHA and no-peptide controls (100 µl) are pipetted into the wells and any IFN-γ ☐present is bound by the immobilized antibody over two hours at room temperature. After washing away unbound substances, an enzyme-linked polyclonal antibody specific for IFN-γ is added to the wells for a two hour incubation at room temperature. Following a wash to remove any unbound antibody-enzyme reagent, a substrate solution is added to the wells for 30 minutes and color developed in proportion to the amount of bound IFN-γ. The color development is stopped and the intensity of the color at 450 nm measured on a Wallac Victor3. Correction for optical imperfections in the plate is made by subtraction of intensities at 540 nm from the 450 nm values. Differences in cytokine levels between experimental groups were evaluated by t-test. A response is considered positive if the observed difference in cytokine expression between the experimental and control wells is statistically different ($p<0.01$).

Flow Cytometry

Splenocytes are plated in 96-well tissue culture plates at $2\times10^6$ cells/well in RPMI 1640 supplemented with 10% FCS, 100 U/mL penicillin, 100 µg/mL streptomycin sulfate. An unstimulated and positive control (ConA) are included in each assay. Cells are incubated overnight at 37° C. at 5% $CO_2$. Following incubation, the cells are washed in PBS containing 1% bovine serum albumin and stained with surface antibodies (e.g., CD4, CD25). Cells are then washed and fixed using the Cytofix/Cytoperm kit (BD PharMingen) according to manufacturer's instructions. Following fixation, the cells are washed twice in Cytoperm buffer and stained with antibodies against intracellular markers (e.g., FOXp3, IL-10). Following staining, the cells are washed and fixed with PBS containing 1% paraformaldehyde in preparation for flow cytometry. Cells are analyzed on a BD Facscalibur machine. 20,000 events are collected per sample. Data analysis is performed using FloJo software. All data are background-subtracted. Comparisons between groups are based on a Wilcoxon rank sum test. A significance of $p<0.05$ is applied for pairwise comparisons and $p<0.01$ is used for multiple comparisons.

Cell Separations/Depletions Methods

Murine Treg cell populations are depleted or positively isolated from PBMC using the InVitrogen dynabeads system (for murine CD4 and CD25) according to manufacturer's instructions (InVitrogen, Carlsbad, Calif.).

Quantification of Antibodies Against Co Administered Antigen

Quantification of IgG antibody to antigens was determined by antibody-capture ELISA. Antigen (10 µg/mL) is dissolved in carbonate buffer and placed into a 96-well microtiter plate overnight at 4° C. The plates were then washed with phosphate-buffered saline containing 0.05% Tween 20 (PBST) and blocked for three hours at room temperature with 5% fetal bovine serum (FBS; Gibco) in PBS. Serial dilutions of sera in 0.5% FBS/PBS are added to the plates and incubated at room temperature for two hours. The microtiter plates are then washed with PBST and 100 µL goat anti-mouse IgG (gamma-chain specific) conjugated to horseradish peroxidase (Southern Biotechnology Associates) diluted 1:10000 in 0.5% FBS/PBS is added to each well. Microtiter plates are washed in PBST and then developed with 3,3',5,5'-tetramethylbenzidine (TMB; Moss). Absorbances were read at a wavelength of 450 nm measured on a Wallac Victor3. Correction for optical imperfections in the plate is made by subtraction of intensities at 540 nm from the 450 nm values.

Example 1

Identification of a Tregitope Composition

Identification of Epitopes in Human IgG Proteins as Regulatory

After evaluating a large number of antibodies for immunogenic potential, a recurring pattern was observed. Certain epitope clusters were occurring in multiple antibodies. Not wishing to be bound by theory, it was reasoned that highly conserved epitope clusters were unlikely to be promoting anti-antibody immune responses. It was further reasoned that these recurring patterns might be either passively tolerated by the immune system or actively engaging regulatory T cells responsible for suppressing anti-antibody immune response. Comparing the sequences of the recurring epitope clusters to the protein database at GenBank established 19 regions contained in the sequences of IgG antibodies that were both conserved and potentially capable of stimulating regulatory T cells (See FIG. 18A and FIG. 18B).

As shown in FIG. 18A and FIG. 18B, according to the EpiMatrix system, all 19 of these regions have significant immune stimulatory potential, each one containing at least one and at most 14 binding motifs and scoring between one and 25 on the EpiVax immunogenicity scale. In addition several of these sequences contained one or more "EpiBars". EpiBars are single 9 mer frames that are expected to bind to at least 4 different Class II HLA. EpiBars are a marker for increased immuno-stimulatory potential.

Conservation

All the IgG derived putative Tregitope sequences were compared to the germline sequences of IgG1, IgG2, IgG3, IgG4, IgA, IgE, IgD and IgM through visual inspection. The IgG-derived Tregitopes were found to be highly conserved in the germline sequences of IgG1, IgG2, IgG3 and IgG4. No homology was found in the germline sequences of IgA, IgE, IgD or IgM. The sequences of the additional Tregitopes are also highly conserved among (variants of human proteins) and are generally present in the circulation in large amounts.

Species

Homology analysis of the IgG-derived Tregitopes to non-human species was performed. The sequences were uploaded into the Basic Local Alignment Search Tool (BLAST) via the NCBI website (ncbi.nlm.nih.gov/blast). The BLAST program compares protein sequences to sequence databases and calculates the statistical significance of matches in order to find regions of local similarity between sequences. The IgG-derived Tregitopes were found to be conserved across non-human species such as mouse, rat, cat, camel, cow and non-human primates. FIG. 19 illustrates a BLAST report of Tregitope-289 (SEQ NO: 4).

Identification of Regulatory Epitopes in Common Circulating Human Proteins

In a subsequent analysis EpiVax identified a set of common and circulating proteins that might also contain Tregitopes. The analyzed protein set included isolates of human: Actin, Albumin, Collagen, Fibrinogen, Haptoglobin, Keratin, Myosin, Osteocalcin, Prostaglandin, Superoxide Dismutase, Titin and Transferrin. Common isolates of each protein were analyzed via EpiMatrix and ClustiMer as described above and a set of high scoring and highly conserved putative T cell epitope clusters was selected for further analysis. See FIG. 18A and FIG. 18B, SEQ ID NOS:38-58.

Example 2

Synthesis and Characterization of a Tregitope Composition by Binding to HLA Class II Molecules Soluble MHC binding assays were performed on the synthetic IgG Tregitopes according to the methods described above. $IC_{50}$ values (μM) were derived by a six point inhibition curve of a strong binding control peptide. As depicted in FIG. 20, the Tregitopes identified by in silico analysis bound to human MHC molecules.

Figure 2:
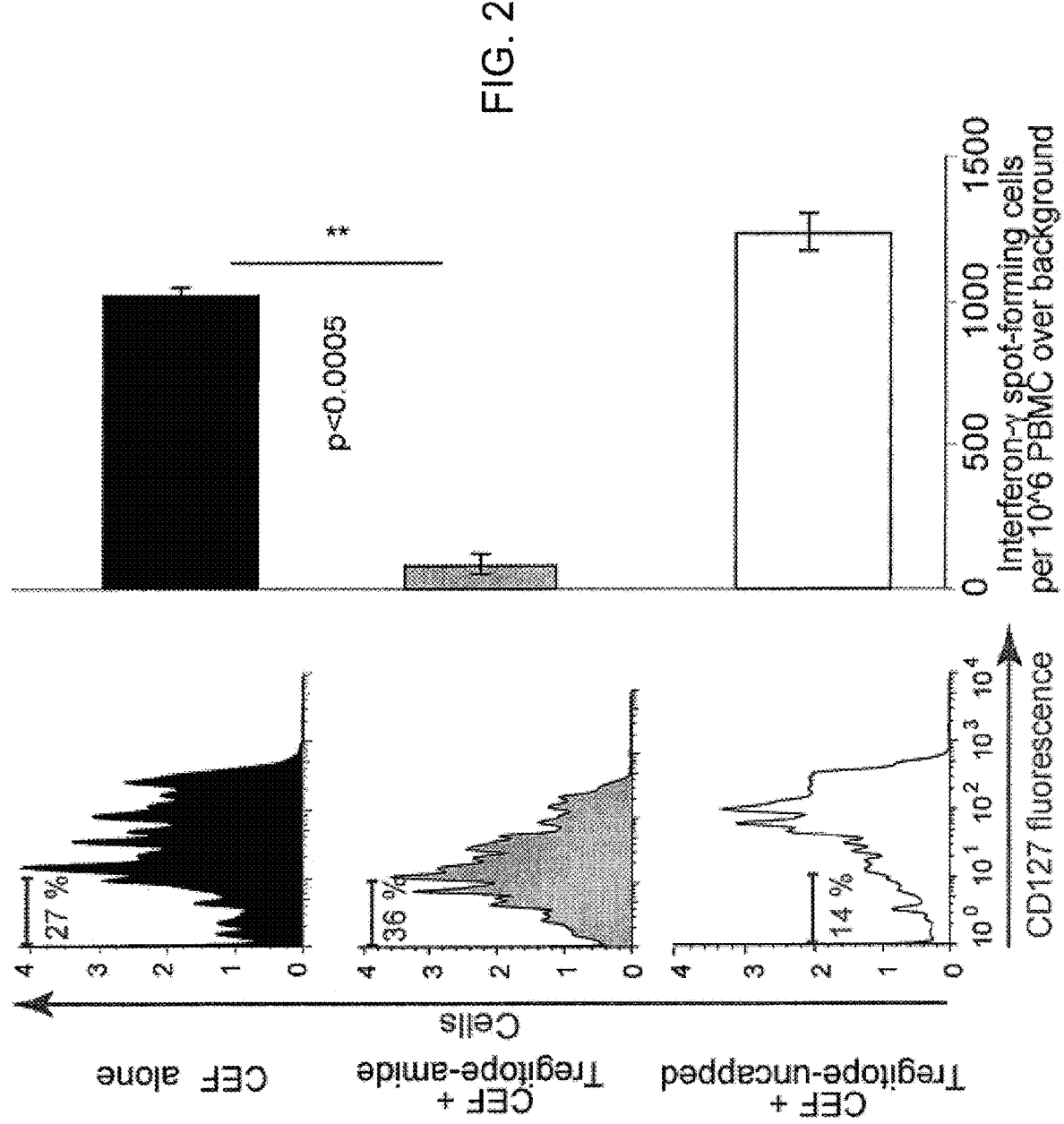
FIG. 2 is a series of graphical representations comparing capped and uncapped peptides. PBMC were stimulated in culture for 8 days with either CEF (positive control peptide pool) alone (top panels), CEF+Tregitope 289-amide (middle panels), or CEF+Tregitope-289-uncapped (bottom panels). As compared to incubation with CEF alone, co-incubation of CEF with Tregitope-289-amide 1) resulted in a higher percentage of cells that had a regulatory phenotype (left panel) and 2) resulted in an associated significant ($p<0.0005$) decrease in the interferon gamma secretion in response to CEF restimulation (right panel). By contrast, co-incubation with Tregitope 289-uncapped (bottom panels) resulted in no significant difference relative to incubation with CEF alone (top panels).

Additional Assays Related to Structural Modifications to Amino and Carboxy Termini Modifications to the amino and carboxy termini of peptides have been shown to alter MHC binding, proteolytic degradation and T cell activation (Maillère, B. et al., *Mol. Immunol.*, 32:1377-85, 1995; Allen, P. et al., *Int. Immunol.*, 1:141-50, 1989). If the observed activation of nTregs were indeed due to Tregitope-specific TCR recognition, then fine alterations at the carboxy terminus of the Tregitope peptide should lead to differential suppressive effects. The same Tregitope peptide sequence was synthesized with and without a C-terminal amide cap. The uncapped peptide was evaluated for affinity to DRB1*0101 and DRB1*1501 in HLA binding assays and shown to bind to both alleles with higher affinity than did the capped peptide. Using PBMC from a DRB1*0101 subject, the ability of Tregitope peptides (capped and uncapped) to suppress responses to co-incubated CEF, a MHC class I immunogenic peptide pool, was then investigated. The cells were stimulated on day 1 and cultured for 6 days. On day 7 the cells were collected and half were stained for CD4, CD25 and CD127 and analyzed by flow cytometry. The remaining cells were added to an IFN-γ ELISpot plate and re-stimulated with CEF. The co-cultures with the C-terminal amide-capped Tregitope led to an increase in CD4+CD25+CD127 low Tregs compared to the uncapped Tregitope-289 (FIG. 2, left panel). Consistent with previous studies that have shown that CD4+CD25+ CD127low Tregs are highly suppressive, the capped Tregitope-289, but not the uncapped Tregitope-289, was able to suppress CEF-specific IFN-γ secretion (FIG. 2, right panel).

Subsequent analysis showed a small 1 dalton change between the capped and uncapped versions of Tregitope-289 (SEQ NO: 4). Tregitope-289 amidated peptide is 1 dalton smaller by mass spectrometry analysis. Amidation of the C-terminus of Tregitope-289 is herein demonstrated to alter its binding and functional characteristics. Because the capped version of Tregitope-289 peptide demonstrated better functionality, the capped (amidated) peptide was used in all subsequent assays. In further support, results displayed here for Tregitope-289 refer to the capped version. Both capped and uncapped versions of the Tregitopes described herein are encompassed by the present invention.

Example 3

Figure 3:
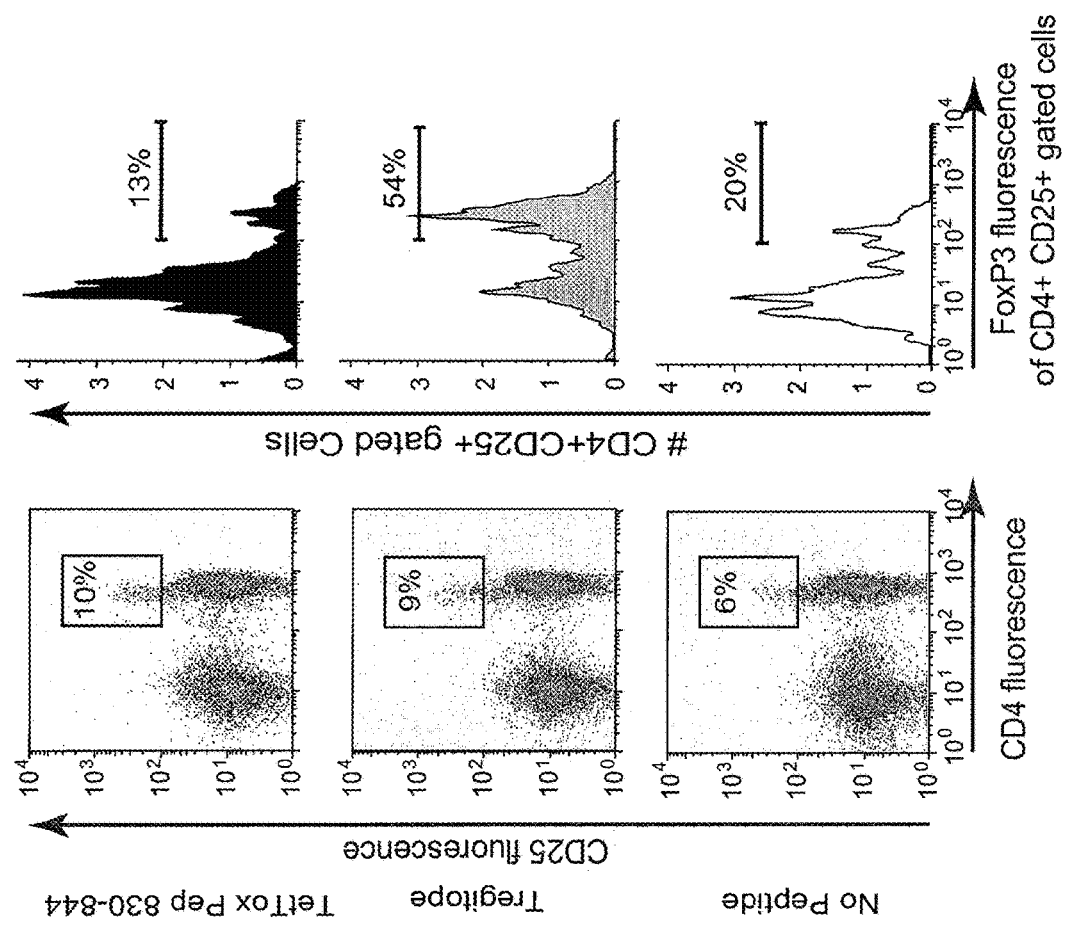
FIG. 3 shows activation of natural Tregs in the presence of Tregitope. Human PBMCs were stimulated directly in vitro for four days in the presence of tetanus toxin peptide ($TT_{830-844}$), Tregitope or no stimulus. Cells were stained extracellularly with anti-CD4 and anti-CD25 and then intracellularly with FoxP3, and analyzed by flow cytometry. Incubation with Tregitope increased the percentage of CD4+ CD25+Foxp3+ T cells (53.6% of 644 cells) as compared to $TT_{830-844}$ (12.5% of 745 cells) or no stimulus (19.5% of 497 cells).

Characterization of a Tregitope Composition by Stimulation of Natural Regulatory T Cells Human PBMCS were stimulated directly ex vivo for 4 days in the presence of tetanus toxin peptide $TT_{830-844}$ alone, Tregitope-289 alone, phytohemagglutinin (a mitogenic positive control) alone, or no stimulus. $1\times10^6$ cells were stained with anti-CD4-FITC (clone RPA-T4; eBioscience) and anti-CD25-APC (clone BC96; eBioscience) antibodies for 30 minutes on ice in Flow Staining Buffer (eBioscience) and washed twice with buffer. Following cell-surface staining, cells were fixed and permeabilized (eBioscience) and stained intracellularly for Foxp3 (clone PCH101; eBioscience) following manufacturer's protocol. The frequency of FoxP3 positive CD4+/CD25+ T cells under various culture conditions was enumerated by Flowjo analysis software. There were similar increases in CD25 expression in both the Tetanus- and Tregitope-stimulated samples indicating T cell activation by both peptides (FIG. 3; results shown for Tregitope-289). Expression of FoxP3 within the CD4+ CD25+ subset, however, differed significantly depending on the stimulus used. Tetanus stimulation led to a 7% decrease in expression of FoxP3, whereas Tregitope stimulation led to a more than two-fold increase in expression, indicating Th and nTreg activation, respectively.

Example 4

Figure 4:
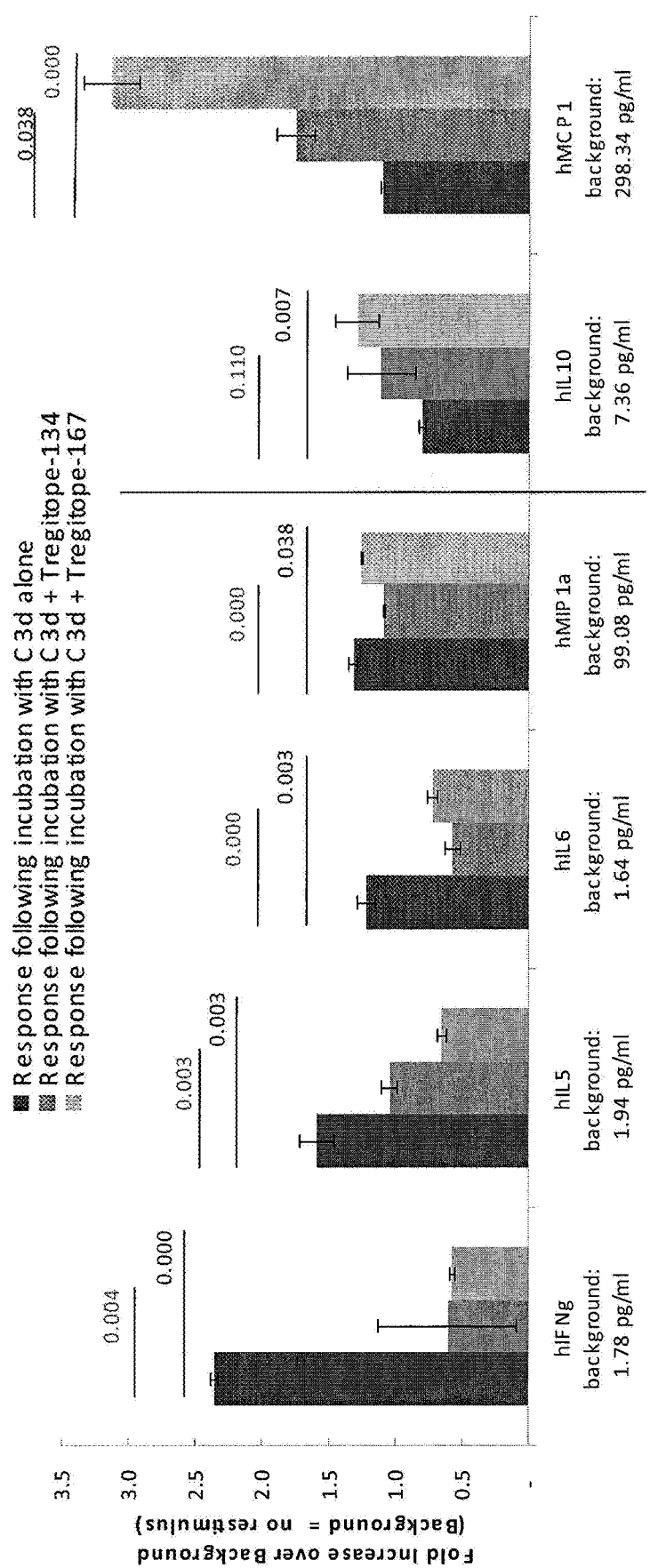
FIG. 4 is a series of bar graphs showing Tregitope induces an up-regulation of T-regulatory cytokines and chemokines and down-regulation of T-effector cytokines and chemokines. Responses to C3d restimulation following initial stimulation with a) a pool of immunogenic peptides derived from C3d protein (black bars); b) C3d peptides+Tregitope-167 (light grey bars) or c) C3d peptides+Tregitope 134 (medium grey bars). Responses are shown as fold increase over background, which was no stimulus (control) in the secondary incubation. The respective baseline (background) values in pg/ml are indicated within the x-axis labels. There was no significant difference in levels of IL-4, TNFα or TGFβ1

Characterization of a Tregitope Composition by Suppression of Co-Administered Antigen In Vitro 4A: Tregitope-167 and Tregitope-134 Down-Regulate Effector Responses and Upregulate Regulatory Responses to Coadministered Antigens In Vitro PBMCs were cultured for 8 days with either a) pool of immunogenic peptides alone, b) a pool of immunogenic peptides with hTregitope-167, or c) a pool of immunogenic peptides with hTregitope-134. Cells were harvested and washed with PBS Cells ($2\times10^5$ cells/well) were plated into 96-well plate and re-stimulated with the immunogenic peptide pool alone, the immunogenic peptide pool and Tregitope, or no peptide (negative control) for 65 hours. Supernatants were analyzed by multiplexed ELISA analysis as described above. The co-incubation of Tregitope during the initial stimulation led to an increase in secretion of the regulatory cytokines and chemokines, IL-10 and MCP-1 and a decrease in the secretion of helper T cell cytokines and chemokines, IL-5, IL-6, IFN-γ and MIP-1α demonstrating the ability of Tregitopes to engage and activate regulatory T cells (FIG. 4).

Figure 5:
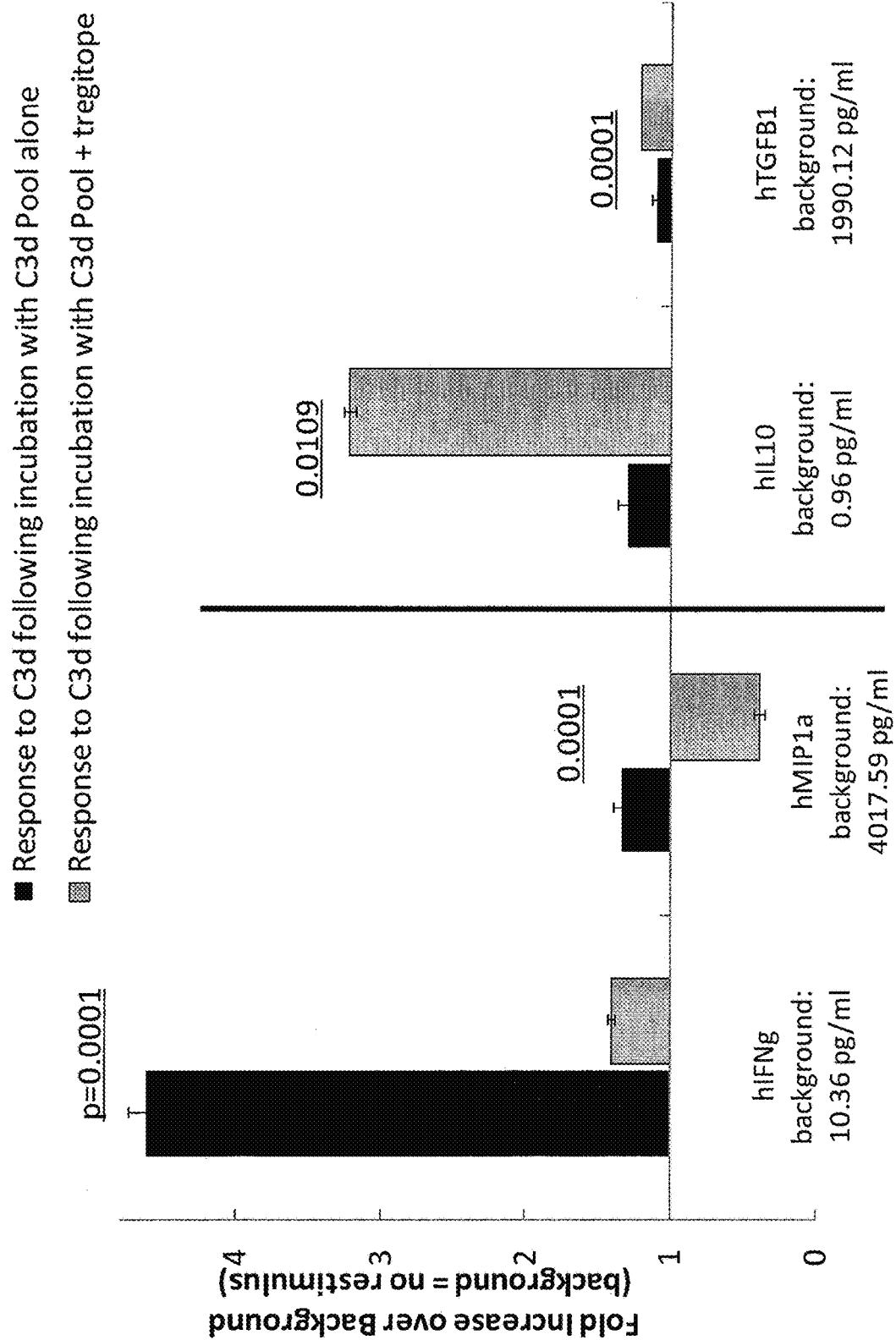
FIG. 5 is a series of bar graphs showing responses to C3d peptide restimulation following initial stimulation with a) a pool of immunogenic peptides derived from C3d protein (black bars) or b) C3d peptides+Tregitope-289 (light grey bars). Responses are shown as fold increase over background, which was no stimulus (control) in the secondary incubation. For each cytokine, baseline (no re-stimulus, background) values are shown within the x-axis labels.

4B: Tregitope-289 Downregulates Effector Responses and Upregulates Regulatory Responses to Co-Administered Antigen In Vitro PBMCs were cultured for 8 days with either a) pool of immunogenic peptides alone, b) a pool of immunogenic peptides with Tregitope-289, or b) a pool of immunogenic peptides with Tregitope-289. The peptides in the immunogenic peptide pool were derived from C3d, an immunogenic autologous protein (Knopf, P. et al., *Immunol. Cell Biol.*, 2008 Jan. 8; doi: 10.1038/sj.icb.7100147). Cells were harvested and washed with PBS. As described, Cells ($2\times10^5$ cells/well) were plated into 96-well plate and re-stimulated in triplicate wells with each condition: C3d pool alone, C3d pool+Tregitope, PHA control, or no peptide (negative control) for 65 hours. Supernatants were analyzed by multiplexed ELISA analysis. Response to positive control PHA was robust following both culture conditions. The co-incubation of Tregitope during the initial stimulation led to an increase in secretion of the regulatory cytokine IL-10, a slight increase in the regulatory chemokine TGFβ, and a decrease in the secretion of the helper T cell cytokines and chemokines IFNγ and MIP 1α further demonstrating the ability of Tregitopes to engage and activate regulatory T cells (FIG. 5).

4C: A Pool of Tregitopes Downregulates Effector Auto-Immune Responses to Co-Administered Antigen In Vitro Co-incubation with epitopes derived from TSHR, the target antigen of Graves' disease, suppresses immune response to the epitopes in PBMC from a patient with Graves' disease. PBMCs were cultured for 8 days with TSHR peptide pools (pool) with or without a pool of Tregitope peptides (Tregitope-134, Tregitope-167, Tregitope-289). Cells were harvested and washed with PBS. As described above, $2.5\times10^5$ cells were re-stimulated in an IL-4 ELISpot plate with either 1) individual TSHR epitopes+the pool of Tregitope-134, Tregitope-167, Tregitope-289), 2) a pool of TSHR epitopes+the pool of Tregitope-134, Tregitope-167, Tregitope-289 or 3) no stimulus control. Response to positive control PHA was robust following both culture conditions.

Figure 6:
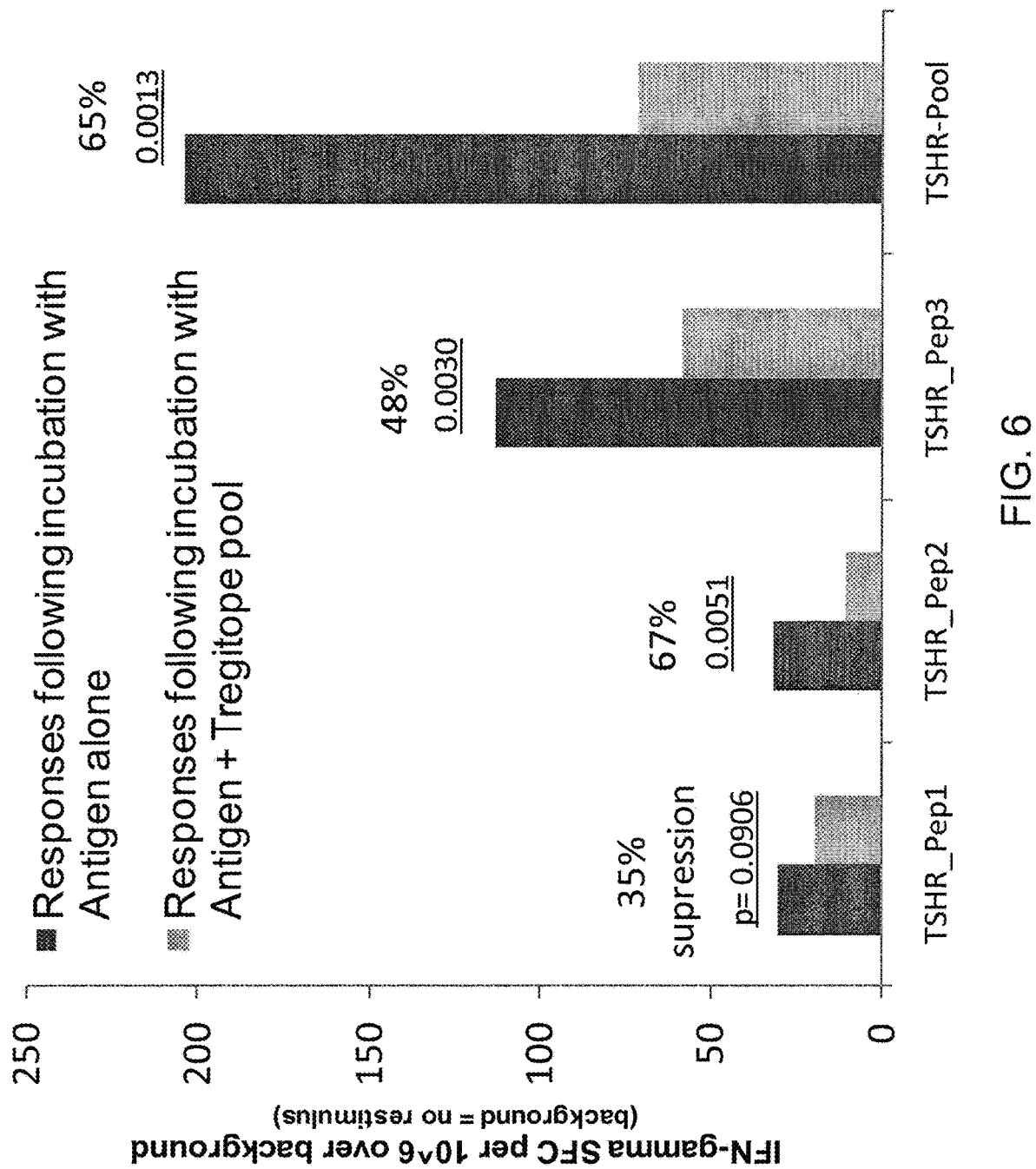
FIG. 6 is a bar graph showing co-stimulation with epitopes derived from TSHR, the target antigen of Graves' disease, suppresses immune response to the epitopes in PBMC from a patient with Graves' disease. PBMC from a patient with Graves' disease were first incubated for 8 days with either 1) a pool of TSHR peptides alone or 2) a pool of TSHR peptides and a pool of Tregitope-134, Tregitope-167, and Tregitope-289. Cells were then harvested, washed and incubated (in IL-4 ELISpot plates as described) with 1) individual TSHR peptides and the Tregitope pool or 2) the pool of TSHR peptides and the Tregitope pool. A "no restimulus" control was also plated. Responses are shown relative to restimulation with no antigen. Black bars correspond to incubations and restimulations done with antigen alone, grey bars correspond to incubations and restimulations with antigen+the Tregitope pool. In this experiment the Tregitope co-incubation suppressed response to individual TSHR peptides by 35% to 67% and suppressed the response to the pool of TSHR peptides by 65%. P values for pairwise comparisons are shown.

The co-incubation of antigen (TSHR peptides) with Tregitope during re-stimulation led to a significant decrease in IL-4 spot-forming cells. This data shows that Tregitopes suppress the cytokine secretion of effector T cells (FIG. 6).

4D: Individual Tregitopes Downregulate Effector Responses to CEF, a Pool of Immunodominant Co-Administered Peptide Antigens In Vitro Co-incubation with Tregitope suppresses immune response to CEF, a pool of Immunodominant peptide epitopes derived from common pathogens. PBMCs were cultured for 8 days with or without individual Tregitope peptides: Tregitope-289, Tregitope 294, Tregitope-029, Tregitope-074, Tregitope-009. Cells were harvested and washed with PBS. As described above, $2.5\times10^5$ cells were re-stimulated in an IFN-γ ELISpot plate with either CEF alone, PHA positive control (not shown) or no-stimulus control. Response to positive control PHA was robust following both culture conditions.

Figure 7:
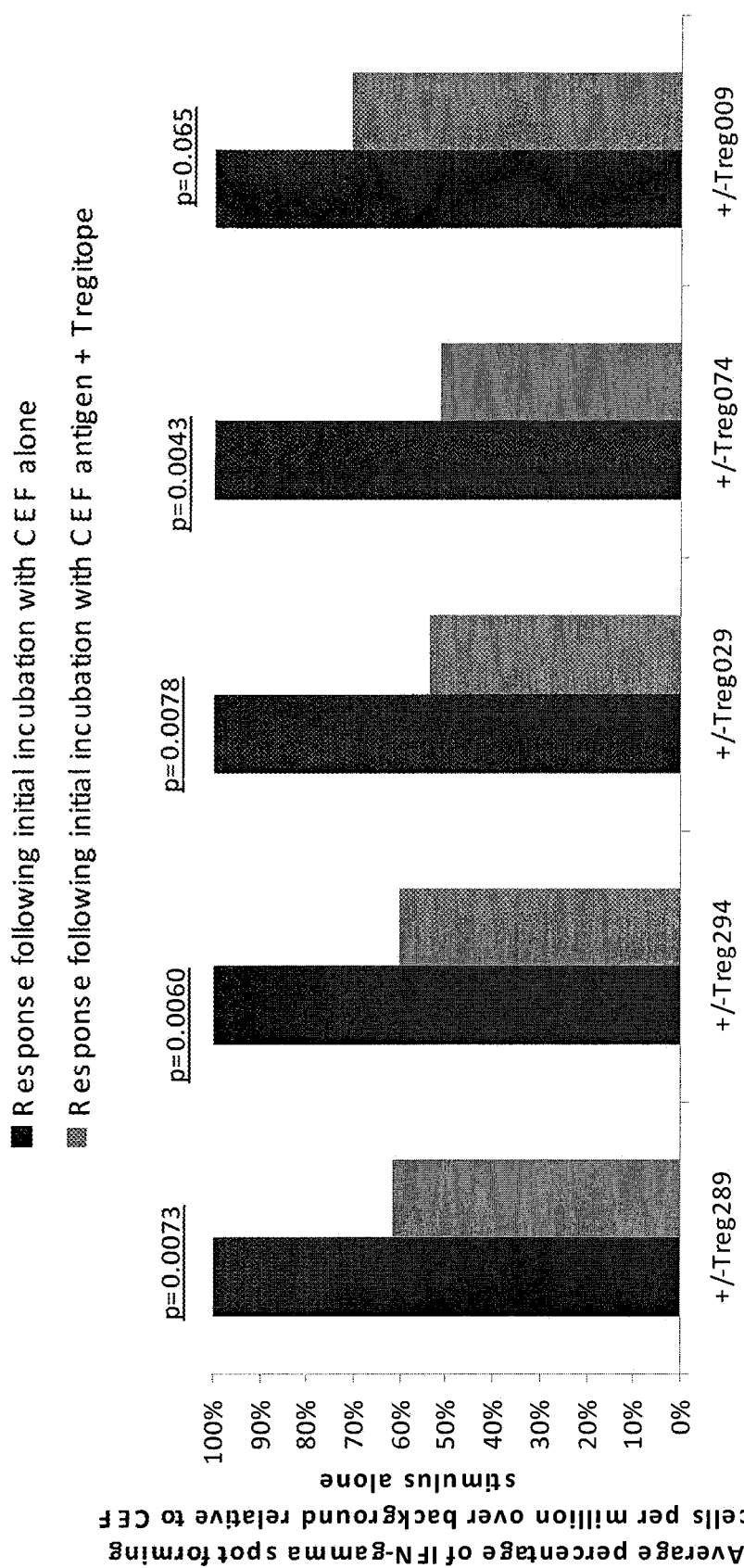
FIG. 7 is a bar graph showing average response of three subjects in response to a commercially available pool of positive control peptides (CEF) following an eight day incubation with one of the following: CEF alone, CEF+ Tregitope-289, CEF+Tregitope 294, CEF+Tregitope-029, CEF+Tregitope-074, or CEF+Tregitope-009. Responses to CEF are suppressed by 29 to 48% depending on the individual Tregitope used. Baseline responses to CEF (in the samples previously incubated to CEF alone) ranged from 1404 to 10139 IFN-γ SFC/million PBMC over background (background is no restimulus). P values for pairwise comparisons are shown.

The co-incubation of antigen (CEF) with Tregitope during incubation led to a significant decrease in IFN-γ spot-forming cells in response to restimulation with CEF. These data show that Tregitopes suppress the cytokine secretion of effector T cells (FIG. 7)

4E: A Pool of Tregitopes Downregulates In Vitro Effector Response to Co-Administered Therapeutic Protein Antigen Co-incubation with Tregitope suppresses immune response to peptide epitopes derived from Botulinum neurotoxin, a protein used to treat dystonia (movement disorders). PBMCs from a subject with evidence of inhibitors (anti-BoNT antibodies) were cultured for 8 days with or without a pool of Tregitope peptides (Tregitope-167, Tregitope-134, Tregitope-289). Cells were harvested and washed with PBS. As described above, $2.5\times10^5$ cells were re-stimulated in an IFN-γ ELISpot plate with individual BoNT peptides, a pool of BoNT peptides, PHA positive control (not shown) or no-stimulus control. Peptides for which there was no significant baseline response are not shown. Response to positive control PHA was robust following both culture conditions.

Figure 8:
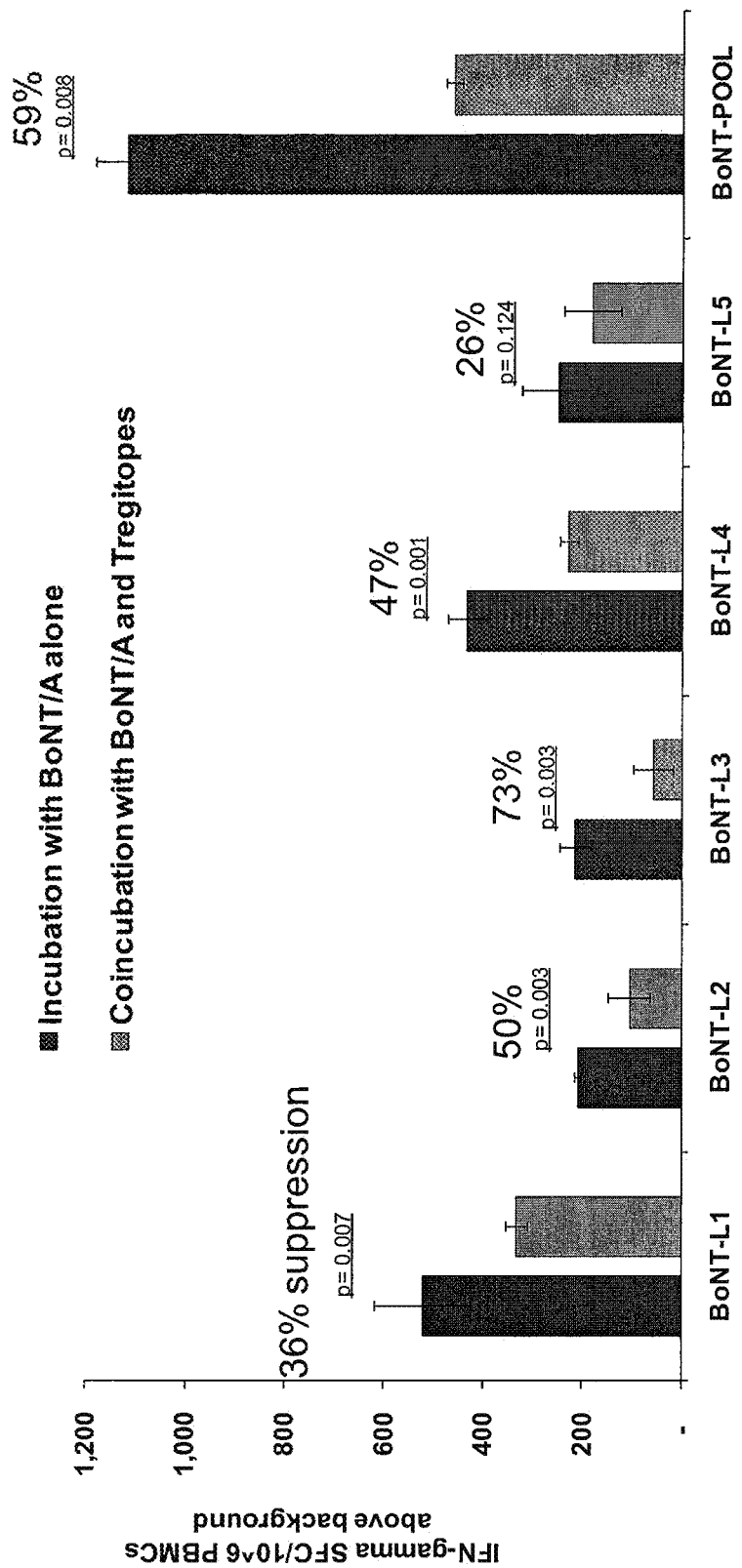
FIG. 8 is a bar graph showing co-incubation with Tregitope suppresses immune response to peptide epitopes derived from Botulinum neurotoxin. Peripheral blood was drawn from a subject with evidence of anti-BoNT/A antibodies. PBMC were first incubated for eight days with either a pool of BoNT/A peptides alone or pool of BoNT/A peptides+a pool of Tregitopes (Tregitope-134, Tregitope-167, and Tregitope-289). Cells were then harvested, washed and then incubated (in IFN-γ ELISpot plates) with BoNT/A peptides individually in triplicate and in a pool in triplicate. Responses are shown relative to re-stimulation with no antigen. Black bars correspond to incubations with antigen alone, grey bars correspond to incubations with antigen+the pool of Tregitopes. The response to BoNT/A was suppressed by 26% to 73%; the response to the pool of BoNT/A peptides was suppressed by 59%. P values for pairwise comparisons are shown.

The co-incubation of antigen (CEF) with Tregitope during incubation led to a significant decrease in IFN-γ spot-forming cells in response to restimulation with CEF. These data show that Tregitopes suppress the cytokine secretion of effector T cells in response to an immunogenic therapeutic protein (FIG. 8 and FIG. 21).

Figure 9:
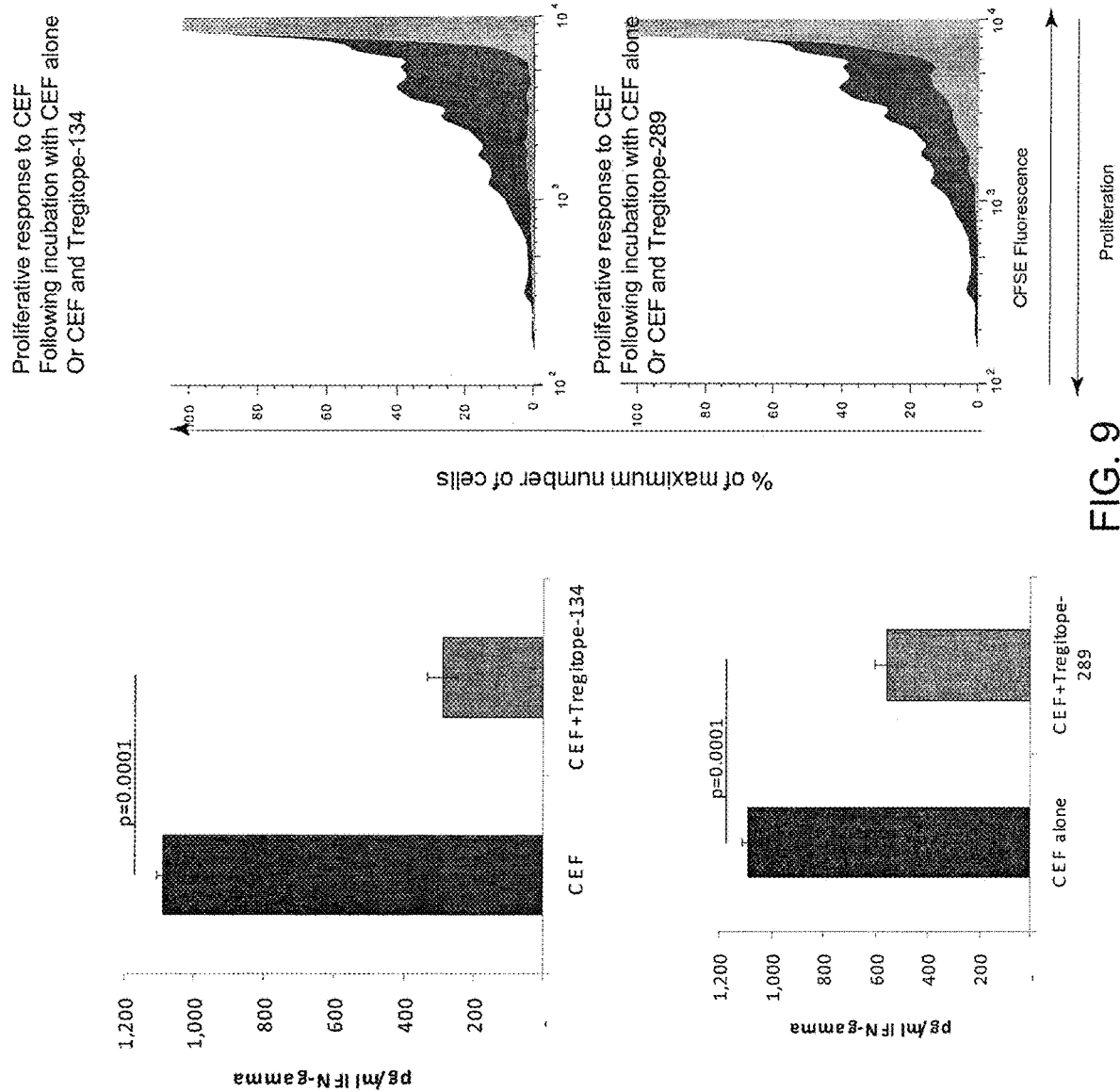
FIG. 9 is a series of graphs showing Tregitope-289 and Tregitope-134 down-regulate proliferation in response to co-administered immunodominant antigens in vitro. PBMCs were isolated from a blood bank donor and stimulated for eight days with CEF alone, CEF+Tregitope-134 or CEF+Tregitope-289. Co-incubation with either of the two Tregitopes lead to a decrease in response to CEF as measured by IFN-γ ELISA (left panel) and to a decrease in proliferation as measured by CFSE Fluorescence (right panel) (grey shaded refers to the suppressed responses with antigen-Tregitope co-incubation; the black refers to baseline responses following incubation with antigen alone).

4F: Tregitope-289 And Tregitope-134 Down-Regulate Proliferation in Response to Co-Administered Immunodominant Antigens In Vitro CEF is a commercially available pool of immunodominant peptide epitopes from common pathogens. PBMCs were cultured for 8 days with CEF alone, CEF+Tregitope-134, or CEF+Tregitope-289. Cells were harvested and washed with PBS. $2\times10^6$ cells were pre-labeled with CFSE dye (Invitrogen) by standard protocol and re-stimulated for 65 hours with CEF pool, or no peptide (negative control), or PHA mitogen control; supernatants were collected and hIFN-γ ELISAs were performed as described above. Response to positive control PHA was robust following both culture conditions. The co-incubation of Tregitope during re-stimulation led to a significant decrease in IFN-γ production (left panel), which correlated with the reduction in the proliferation of effector T cells (FIG. 9, right panel).

Figure 10:
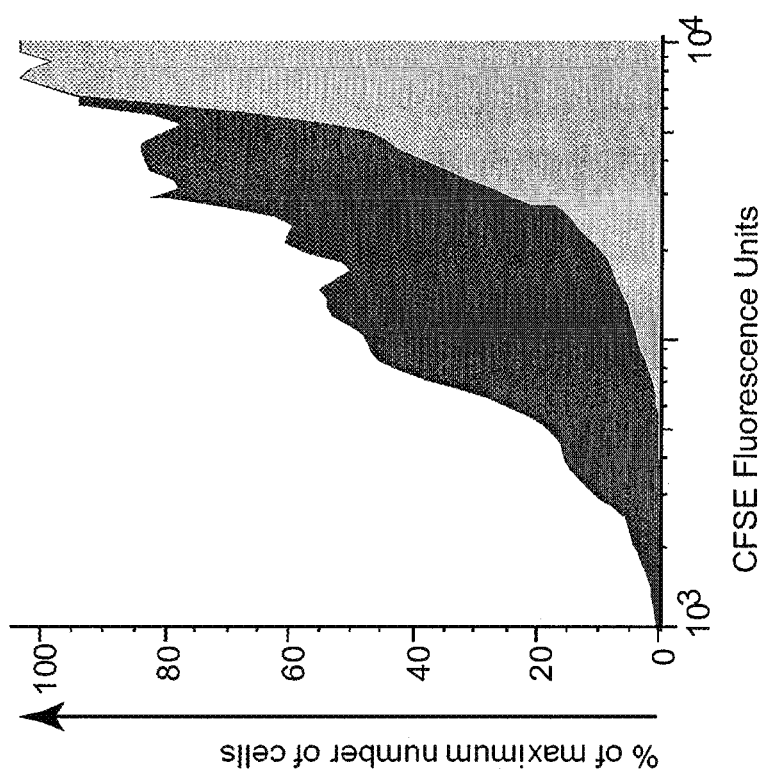
FIG. 10 is a plot showing response to vaccinia peptide. PBMCs were isolated from a blood bank donor and stimulated for eight days with CEF alone, CEF+Tregitope-134 or CEF+Tregitope-289. Co-incubation with either of the two Tregitopes led to a decrease in response to CEF as measured by IFN-γ ELISA (left panel) and to a decrease in proliferation as measured by CFSE Fluorescence (right panel). Grey shaded refers to the suppressed responses with antigen-Tregitope co-incubation; the black refers to baseline responses following incubation with antigen alone.

4G: Tregitope-289 Downregulates Proliferation in Response to Co-Administered Antigen In Vitro PBMCs from a subject previously immunized with vaccinia were cultured for 8 days with either an immunogenic vaccinia peptide alone or an immunogenic vaccinia peptide with Tregitope-289 as described above. Cells were harvested and washed with PBS. 2×10⁶ cells were pre-labeled with CFSE dye (Invitrogen) by standard protocol and re-stimulated with the vaccinia peptide, vaccinia peptide and Tregitope-289, or no peptide (negative control) for 65 hours. The co-incubation of Tregitope during incubation led to a significant decrease in proliferation of the effector T cells further demonstrating the ability of regulatory T cells activated by Tregitope to reduce the proliferation of effector T cells (FIG. 10).

4H: Tregitope Suppression is Mediated by Cells with a Regulatory Phenotype (CD4+CD25Hi T Cells) and Upregulation of IL-10

Two samples of PBMC from a single dust-mite-allergic individual were prepared. One sample was stained with anti-CD4 and anti-CD25 antibodies and analyzed by flow cytometry. In this sample the CD4+CD25Hi subset of cells were depleted from the remaining PBMC by the methods described above. The other sample was left intact. The two samples were then co-stimulated HDM lysate with or without Tregitope-289. CD4+CD25Hi-depleted PBMC were less able to suppress IFN-γ than were non-depleted PBMC, indicating that suppressive effects of Tregitopes are mediated by CD4+CD25Hi cells. In an ancillary analysis in (intact) PBMCs, CD4+ proliferative responses to HDM lysate were suppressed following co-incubation with HDM lysate and Tregitope-289 as compared with incubation with HDM lysate alone.

Figure 11:
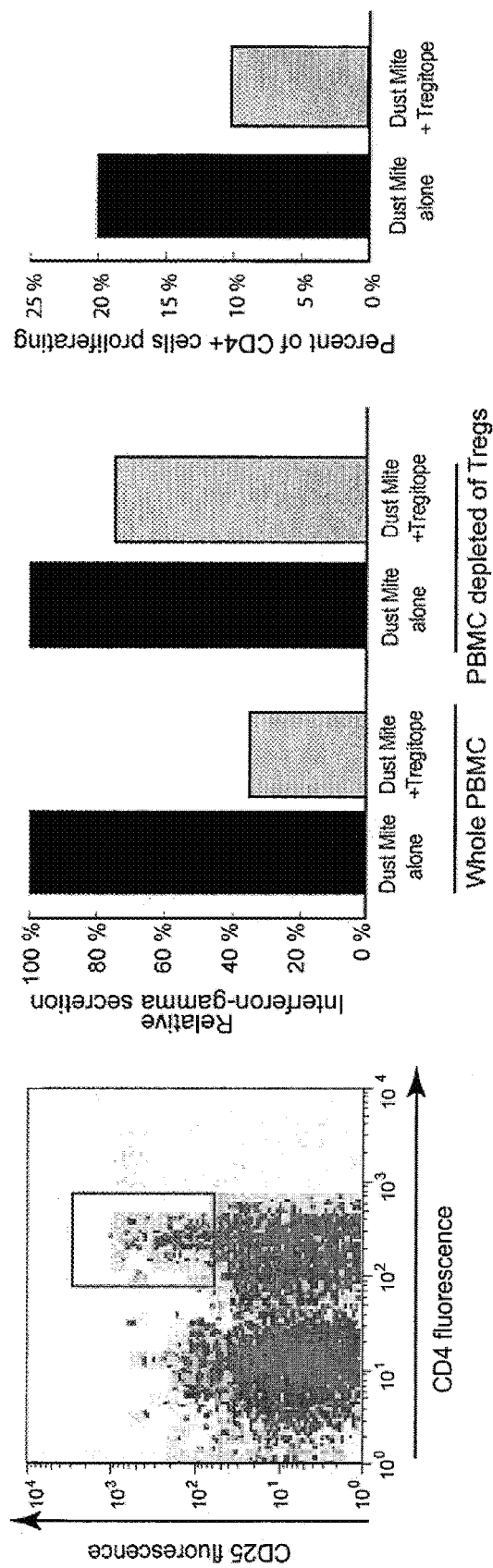
FIG. 11 is a series of graphs showing Tregitope suppression is mediated by cells with a regulatory phenotype. Tregitope suppression is dependent on CD4+ CD25Hi T cells. Left panel: PBMC from allergic individuals were stained with anti-CD4 and anti-CD25 antibodies and analyzed by flow cytometry. The CD4+CD25Hi subset (gate) was depleted from the remaining PBMC. Center panel: CD4+CD25Hi depleted and non-depleted PBMC were co-stimulated HDM lysate with or without Tregitope-289. CD4+CD25Hi depleted PBMC were less able to suppress IFN-γ than non-depleted PBMC. Right panel: co-incubation of HDM lysate and Tregitope-289 leads to decreased proliferation of CD4+ cells in response to HDM lysate stimulus.

FIG. 11 documents the requirement for CD4+/CD25hi T cells in the initial co-incubation. In the presence of CD4+CD25hi cells, co-stimulation with Tregitope-289 and HDM caused suppression of gamma interferon release following restimulation with HDM alone; in the absence of CD4+CD25hi cells (sorted prior to the incubation, co-stimulation with Tregitope-289 and HDM was associated with a lower amount of suppression (16%: 16.5 to 12.4 pg/ml) as compared with a higher amount of suppression (65%: 33.5 to 11.8 pg/ml) following restimulation with HDM alone. FIG. 11 show that the cellular subset containing Tregs is necessary for the induction of tolerance to an antigen.

Figure 12:
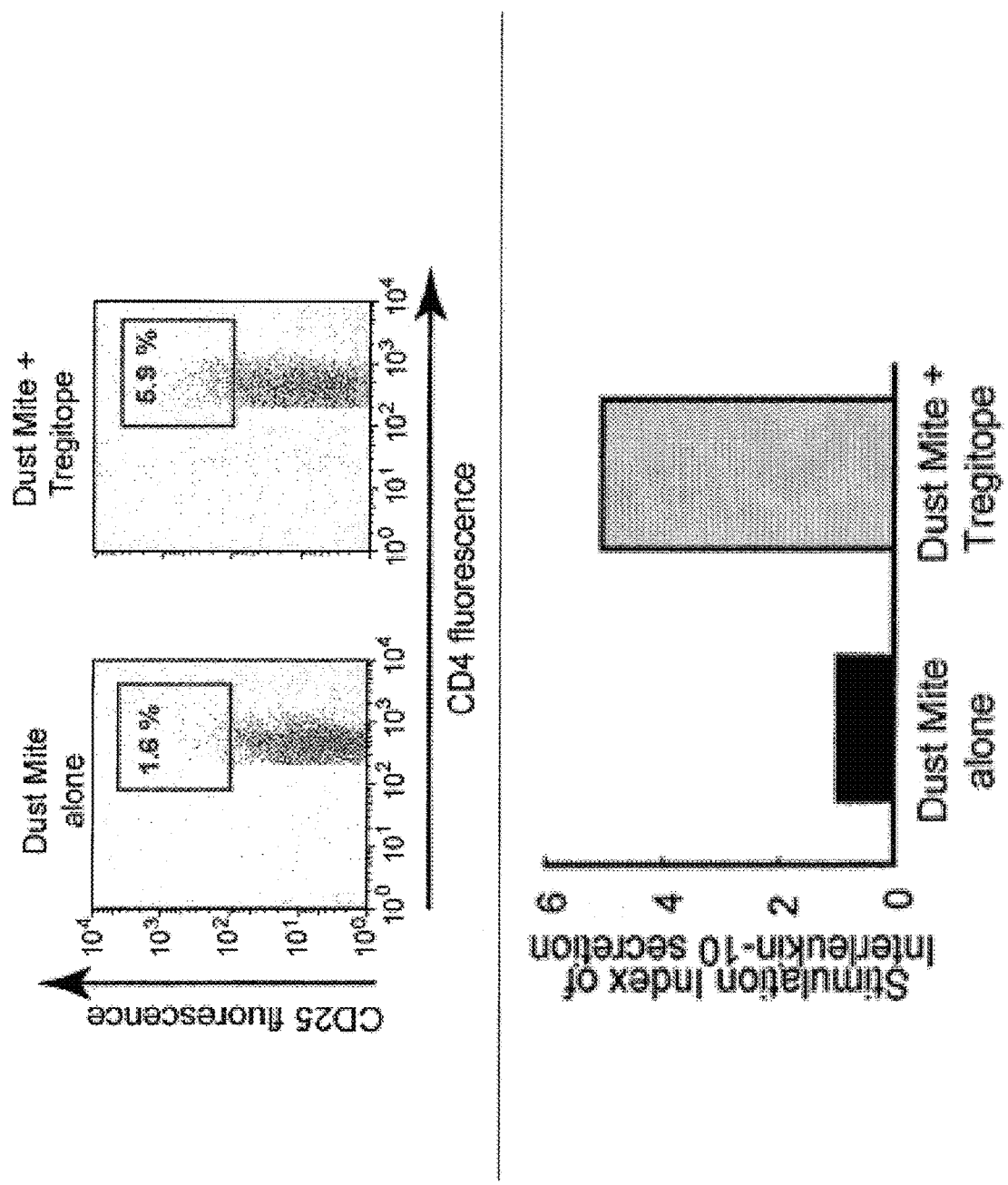
FIG. 12 is a plot and graph showing expansion of TReg (CD4/CD25 Hi) correlates with IL-10 secretion. The expansion of CD4 CD25hi T cells following co-incubation with Tregitope-289 and HDM; and the amount of IL-10 secreted by the co-incubated cells following restimulation with HDM alone. Results for co-incubation with Tregitope-167 are similar: increase from 1.67% to 7.5% CD4/CD25hi cells and a five-fold increase in IL-10 secretion.

4I: Tregitope Co-Incubation Causes Expansion of Cells With a Regulatory Phenotype (CD4+ CD25Hi T Cells) and Upregulation of Regulatory Cytokine IL-10 in Response to an Allergen Induction of adaptive tolerance: to determine if Tregitope nTreg activation could lead to generation of allergen-specific aTReg, PBMC (from dust mite allergic individuals) first incubated for 8 days with Dust Mite (DM) antigen alone, dust mite antigen+tregitope-289, or dust mite antigen+Tregitope-167 were analyzed. As shown in the top panel (FIG. 12), co-incubation of PBMC with DM antigen and Tregitope-289 led to a nearly four-fold expansion of CD4+ CD25Hi cells; the same was true of PBMC co-incubated with DM antigen and Tregitope-167 (1.6 to 7.5%). In both Tregitope co-incubations, IL-10 secretion was also found to be increased five-fold (FIG. 12, bottom panel); a finding consistent with the possibility that the increased CD4+ CD25Hi cells may be HDM-specific adaptive Treg. One of skill in the art can confirm that the expanded CD4+CD25hi population is secreting IL-10 in this in vitro assay. The IL-10 secretion in response to the co-incubated antigen, in the presence of an expanded population of CD4+CD25hi Tregulatory cells, indicates that adaptive Tregs were induced during the coincubation with antigen.

These data show, in the same patient and the same experiment, the expansion of CD4 CD25hi T cells following co-incubation with Tregitope-289 and DM antigen and following co-incubation with Tregitope-167 and DM antigen; and the amount of IL-10 secreted by the co-incubated cells following restimulation with HDM alone.

Figure 13:
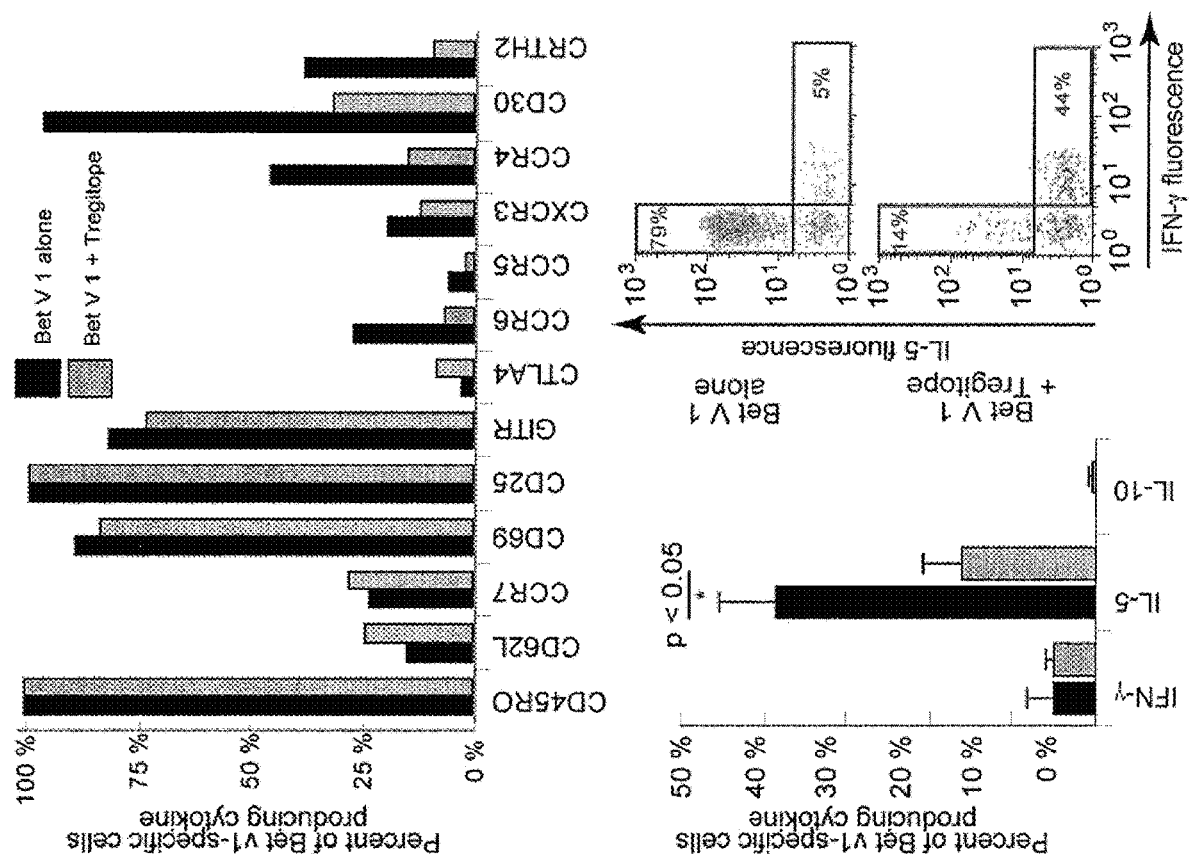
FIG. 13 is a series of graphs and plots showing Tregitope co-incubation causes suppression of antigen-specific allergic Th2 response. Co-culture with Tregitope and Bet v 1141-155 allergen causes a shift from Th2 effector to Th1/T$_{Reg}$. PBMC from three birch-tree—pollen-allergic subjects were co-stimulated with Bet v 1141-155 peptide with or without Tregitope-167. Ten day Tregitope co-stimulation led to a decrease in IL-5 secretion (lower left panel) and to a decrease in Th2-associated surface markers (top panel) by Bet v 1144-155 tetramer positive CD4+ cells. Prolonged culture (30 days, lower right panel) led to a significant shift from Th2 (IL-5) to Th1 (IFN-γ) in Bet v 1144-155-specific cells.

4J: Tregitope Co-Incubation Causes Suppression of Antigen-Specific Allergic Th2 Responses Tregitope co-incubation also led to a significant decrease in expression of CCR4, CD30, CRTH2, and CCR6, which have been shown to be associated with Th2 responses. Modulation of cytokine responses by allergen-specific CD4+ T cells following extended Tregitope co-stimulation was subsequently evaluated. After 30 days in culture, Tregitope co-stimulation contributed to the development of a mixed population of Bet v 1 $_{1141-1155}$-specific CD4+ T cells. Following prolonged stimulation with antigen and Tregitope, 42% of these epitope-specific cells were neither IL5 nor IFN-γ positive, and 44% demonstrated a shift to a Th-1-like increased interferon response in this prolonged incubation (FIG. 13).

Of note, the study subjects were selected for presence of HLA DR*1 1501 to improve the chances of tetramer binding; the effect of Tregitope-167 was more pronounced (five fold increase in Treg induction) than for Tregitope 289 (three fold increase). Tregitope-289 was not shown to bind to DR 1501 in HLB binding assays. In contrast Tregitope-167 binds avidly to HLA 1501 (87% inhibition of binding at 50 μM).

Example 5

Characterization of a Tregitope Composition by Suppression of Co-Administered Antigens In Vivo

Figure 14:
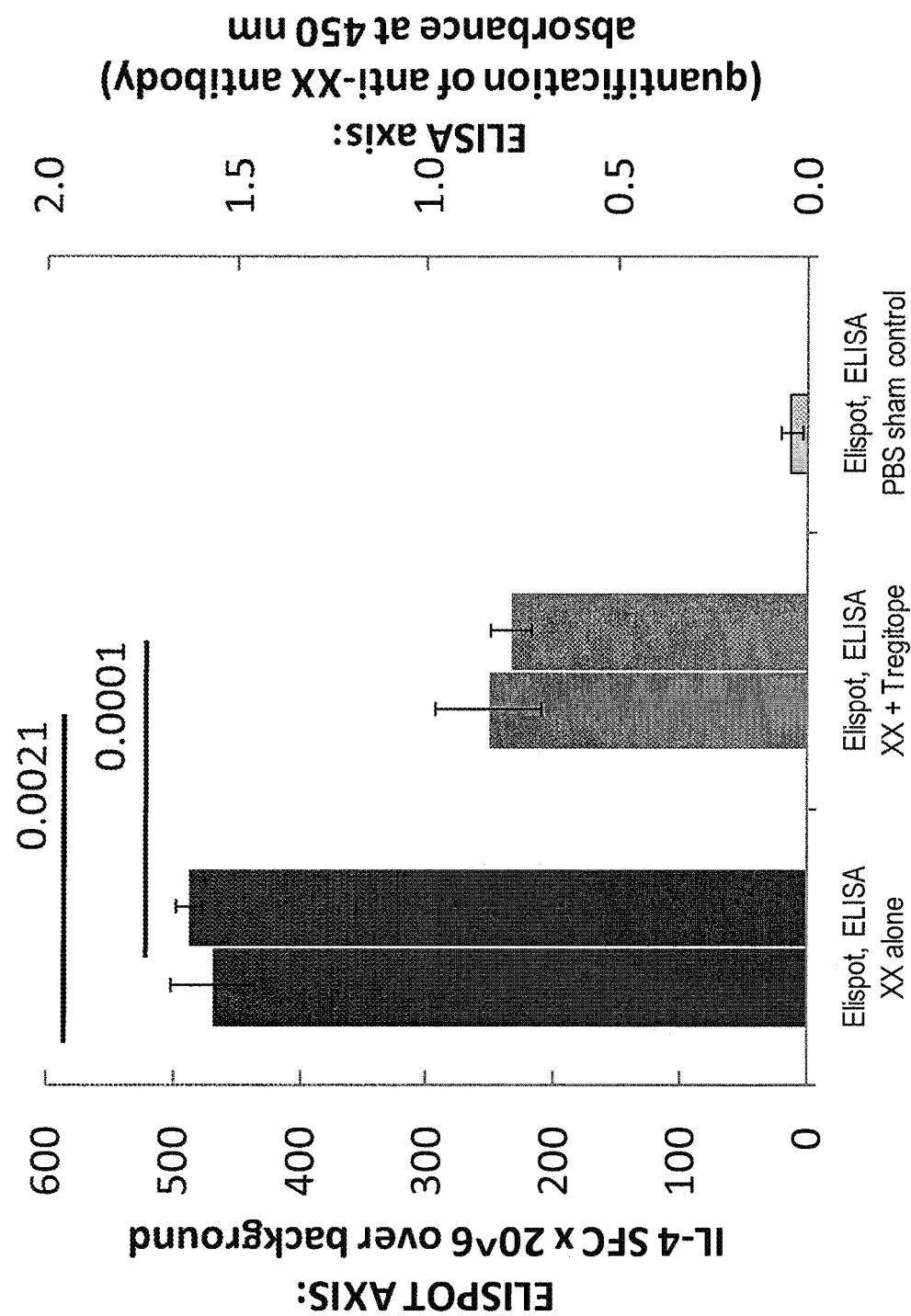
FIG. 14 is a graph showing Tregitope co-administration causes suppression of effector responses to co-administered protein therapeutic in vivo. ANTIGEN-XX (see Example 5A) immunization alone (black bars) provokes a robust response by both IL-4 (left bars in pair, left axis) and anti-ANTIGEN-XX antibody titers (right bars in pair, right axis). These responses are both halved (grey bars) when ANTIGEN-XX is co-administered with the murine homologues of Tregitope-167 and Tregitope-106. Responses to ANTIGEN-XX in sham-immunized animals are negative as expected. Responses by Antibody (right bars in pair) and IL-4 ELISpot (left bars in pair) are correlated.

5A: Tregitope Co-Administration Causes Suppression of Effector Responses to Co-Administered Protein Therapeutic In Vivo It is shown herein that Tregitopes suppress response to a therapeutic protein of bacterial origin, which is referred to as "ANTIGEN-XX" (FIG. 14). ANTIGEN-XX has caused significant immunogenicity in humans in unpublished studies. Whether the Tregitopes of the invention could suppress the effector immune response protein in vivo was investigated. HLA DR4 Transgenic mice (4-6 wk female) were injected weekly 3× subcutaneously (scruff of the neck) with either 1) 50 μg ANTIGEN-XX alone, 2) 50 μg ANTIGEN-XX+25 μg murine Tregitope-167 and 25 μg murine Tregitope 106 or 3) PBS sham control. Splenocytes were harvested and plated in murine IL-4 elispot plates as described above.

Quantification of IgG antibody to ANTIGEN-XX was determined by antibody-capture ELISA as described above. ANTIGEN-XX (10 μg/mL) was dissolved in carbonate buffer (10 mM $Na_2CO_3$ and 35 mM $NaHCO_3$ [pH 9]) and placed into a 96-well microtiter plate overnight at 4° C. The plates were then washed with phosphate-buffered saline containing 0.05% Tween 20 (PBST) and blocked for 3 hours at room temperature with 5% fetal bovine serum (FBS; Gibco) in PBS. Serial dilutions of sera in 0.5% FBS/PBS were added to the plates and incubated at room temperature for 2 hours. The microtiter plates were then washed with PBST and 100 μL goat anti-mouse IgG (gamma-chain specific) conjugated to horseradish peroxidase (Southern Biotechnology Associates) diluted 1:10000 in 0.5% FBS/PBS is added to each well. Microtiter plates are washed in PBST and then developed with 3,3',5,5'-tetramethylbenzidine (TMB; Moss). Absorbances were read at a wavelength of 450 nm measured on a Wallac Victor3. Correction for optical imperfections in the plate is made by subtraction of intensities at 540 nm from the 450 nm values. Response to positive control PHA was robust following both immunization conditions and both assay readouts.

This study confirms the suppressive effects of the murine homologues of human Tregitopes co-administered with antigen in vivo.

5B: Tregitope Co-Administration Causes Suppression of Effector Responses to Co-Administered Allergen In Vivo Dust mites cause significant allergic responses in humans, and the mouse model using house dust mite lysate (HDML) is accepted as a model that is similar to humans. Whether the Tregitopes of the invention could suppress the effector immune response to HDML in vivo was investigated. HLA DR4 Transgenic mice (4-6 wk female) were injected weekly 3× subcutaneously (scruff of the neck) with either 1) 50 μg HDML alone, 2) 50 μg HDML+50 μg murine homologue of Tregitope-289 or 3) PBS sham control. In a fourth arm, mice were first presensitized to HDML through 3 weekly injections of 50 μg and then treated with coinjections of HDML (50 μg) and Tregitope-289). One week following the final injections, mice were sacrificed.

Splenocytes were harvested and plated in murine IL-4 ELISpot plates as described above; to the plated cells were added (in triplicate): PBS (no stimulus control), HDM Lysate, purified HDM antigen DerP2, and PHA. HDM DerP2 is a component of HDM Lysate.

Figure 15:
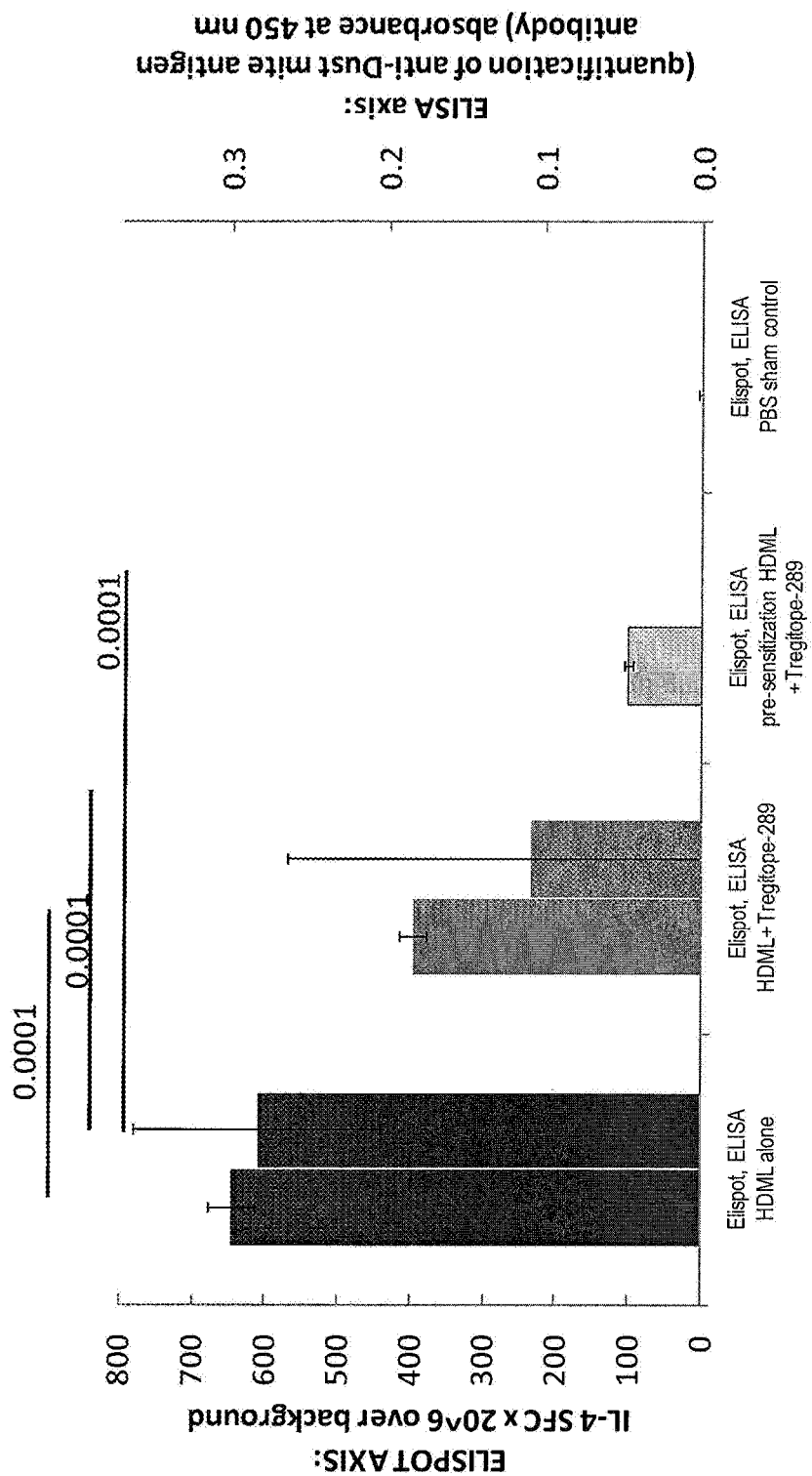
FIG. 15 is a graph showing IL-4 and antibody responses to house mite lysate (HDML) and dust mite antigen. HDML immunization (black bars) provokes a robust response by both IL-4 (Left bars in pair, left axis) and anti HDM Antigen antibody titers (Right bars in each pair, right axis). These responses are both halved (grey bars) when HDML is co-administered with the murine homologue of Tregitope-289. Responses to HDML in sham-immunized animals are negative as expected. Responses by Antibody (right bars in pair) and IL-4 ELISpot (left bars in pair) are correlated. These graphs show 38% suppression in vivo in DM naïve mice and 84% percent in the case of presensitized mice. See Example 5B.

Serum was obtained by cardiac puncture. Quantification of IgG antibody to HDM antigen was determined by antibody-capture ELISA as described above. HDM antigen DerP2 (10 μg/mL) was placed into a 96-well microtiter plate overnight at 4° C. The plates were then washed with phosphate-buffered saline containing 0.05% Tween 20 (PBST) and blocked for three hours at room temperature with 5% fetal bovine serum (FBS; Gibco) in PBS. Serial dilutions of sera in 0.5% FBS/PBS were added to the plates and incubated at room temperature for four hours. The microtiter plates were then washed with PBST and 100 μL goat anti-mouse IgG (gamma-chain specific) conjugated to horseradish peroxidase (Southern Biotechnology Associates) diluted 1:10000 in 0.5% FBS/PBS is added to each well. Microtiter plates are washed in PBST and then developed with 3,3',5,5'-tetramethylbenzidine (TMB; Moss). Absorbances were read at a wavelength of 450 nm measured on a Wallac Victor3. Correction for optical imperfections in the plate is made by subtraction of intensities at 540 nm from the 450 nm values. Response to positive control PHA was robust following both immunization conditions and both assay readouts (FIG. 15).

This study confirms the suppressive effects of the murine equivalents of human Tregitopes co-administered with DM antigen in vivo.

Figure 16:
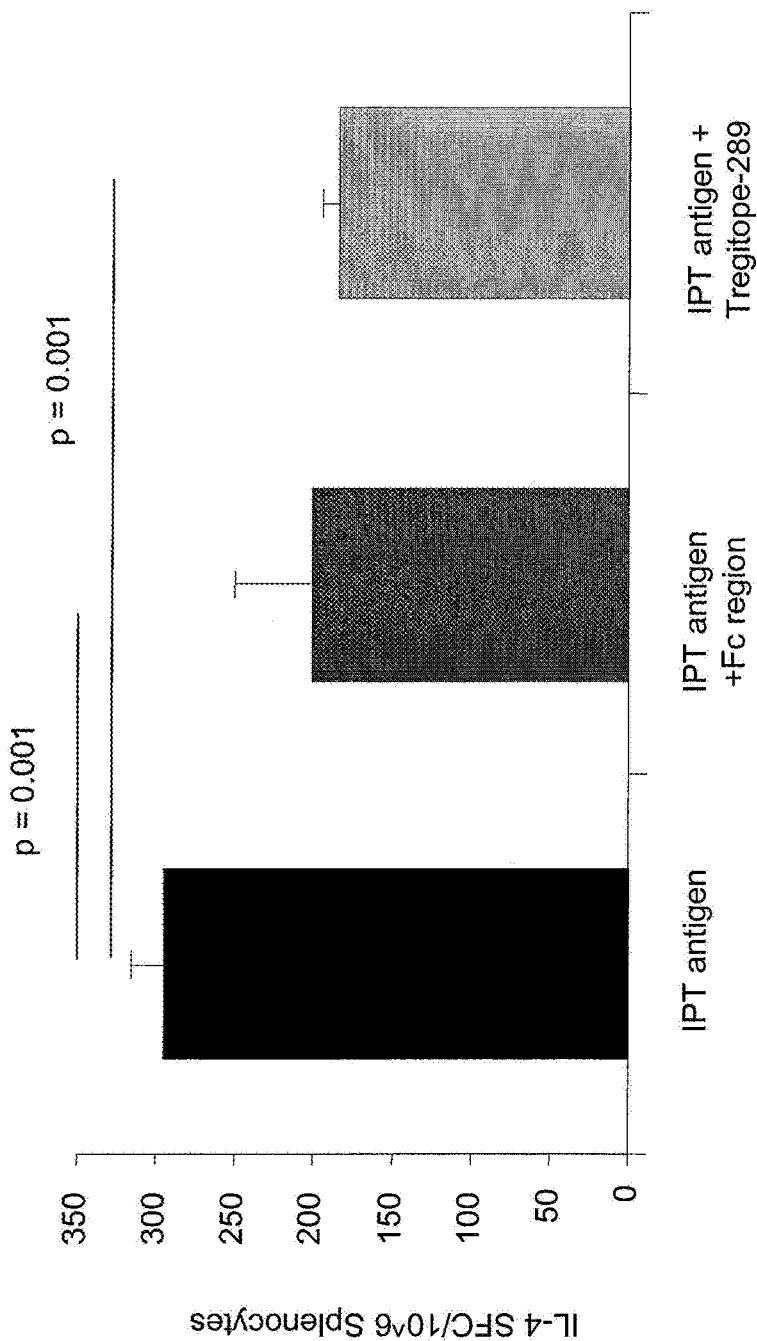
FIG. 16 is a bar graph showing in vivo suppression of T effector response to immunogenic peptide therapeutic ("IPT") by Tregitope co-administration. HLA DR4 Tg mice were dosed three times subcutaneously with IPT alone or IPT+murine FC, or IPT+Tregitope-289 (murine homologue). One week following the last dose, the mice were sacrificed and splenocytes were stimulated with the immunogenic peptide therapeutic in a 48 hr IL-4 ELISpot assy. Co-administration of immunogenic protein therapeutic with either Fc or Tregitope-289 lead to a significant reduction in IL-4 spot-forming cells. See Example 5C.

5C: Tregitope Co-Administration Causes Suppression of Effector Responses to Co-Administered Therapeutic In Vivo To test whether Tregitope co-administration in vivo would be able to suppress immune responses to an immunogenic therapeutic protein, HLA DRB1*0401 was injected into mice three times weekly with preparations of 50 μg immunogenic protein therapeutic ("IPT") alone or in combination with either 50 μg Tregitope-289 (murine homologue) or IPT in combination with the murine Fc. Co-administration of IPT with murine Fc region reduced the IL-4 response, however, in vivo co-administration of "IPT" with murine homologue Tregitope-289, led to an even greater decrease in IL-4 by ELISpot (FIG. 16).

Example 6

Generation of a FVIII-Tregitope Construct

Fusion of Tregitope with an immunogenic protein can lead to the induction of peripheral tolerance of the immunogenic protein. Clotting Factor VIII is immunogenic in people with severe hemophilia A. Chimeric constructs comprised of the coding sequence of Factor VIII and Tregitope are produced (Sambrook et al., *Molecular Cloning: A Laboratory Manual,* 2 ed., Cold Spring Harbor Laboratory Press, (1989)). Briefly, the Factor VIII coding region fused at the carboxyterminal to a Tregitope is generated by annealing overlapping oligos and sub-cloned into an expression plasmid. The plasmids are transfected into DG44 CHO cells and stable transfectants selected. The chimeric protein is purified over a immunoaffinity column and evaluated for tolergenicity. Table 1 illustrates one embodiment of such a chimeric protein.

TABLE 1

| Factor VIII-Tregitope (Tregitope bold) |
|---|
| SEQ ID NO: 1 |
| MQIELSTCFFLCLLRFCFSATRRYYLGAVELSWDYMQSDLGELPVDARFP |
| PRVPKSFPFNTSVVYKKTLFVEFTDHLFNIAKPRPPWMGLLGPTIQAEVY |
| DTVVITLKNMASHPVSLHAVGVSYWKASEGAEYDDQTSQREKEDDKVFPG |
| GSHTYVWQVLKENGPMASDPLCLTYSYLSHVDLVKDLNSGLIGALLVCRE |
| GSLAKEKTQTLHKFILLFAVFDEGKSWHSETKNSLMQDRDAASARAWPKM |
| HTVNGYVNRSLPGLIGCHRKSVYWHVIGMGTTPEVHSIFLEGHTFLVRNH |
| RQASLEISPITFLTAQTLLMDLGQFLLFCHISSHQHDGMEAYVKVDSCPE |
| EPQLRMKNNEEAEDYDDDLTDSEMDVVRFDDDNSPSFIQIRSVAKKHPKT |
| WVHYIAAEEEDWDYAPLVLAPDDRSYKSQYLNNGPQRIGRKYKKVRFMAY |
| TDETFKTREAIQHESGILGPLLYGEVGDTLLIIFKNQASRPYNTYPHGIT |
| DVRPLYSRRLPKGVKHLKDEPILPGEIFKYKWTVTVEDGPTKSDPRCLTR |
| YYSSFVNMERDLASGLIGPLLICYKESVDQRGNQIMSDKRNVILFSVFDE |
| NRSWYLTENIQRFLPNPAGVQLEDPEFQANIMHSINGYVFDSLQLSVCLH |
| EVAYWYILSIGAQTDFLSVFFSGYTFKHKMVYEDTLTLFPFSGETVFMSM |
| ENPGLWILGCHNSDFRNRGMTALLKVSSCDKNTGDYYEDSYEDISAYLLS |
| KNNAIEPRSFSQNSRHPSTRQKQFNATTIPENDIEKTDPWFAHRTPMPKI |
| QNVSSSDLLMLLRQSPTPHGLSLSDLQEAKYETFSDDPSPGAIDSNNSLS |
| EMTHFRPQLHHSGDMVFTPESGLQLRLNEKLGTTAATELKKLDFKVSSTS |
| NNLISTIPSDNLAAGTDNTSSLGPPSMPVHYDSQLDTTLFGKKSSPLTES |
| GGPLSLSEENNDSKLLESGLMNSQESSWGKNVSSTESGRLFKGKRAHGPA |
| LLTKDNALFKVSISLLKTNKTSNNSATNRKTHIDGPSLLIENSPSVWQNI |
| LESDTEFKKVTPLIHDRMLMDKNATALRLNHMSNKTTSSKNMEMVQQKKE |
| GPIPPDAQNPDMSFFKMLFLPESARWIQRTHGKNSLNSGQGPSPKQLVSL |
| GPEKSVEGQNFLSEKNKVVVGKGEFTKDVGLKEMVFPSSRNLFLTNLDNL |
| HENNTHNQEKKIQEEIEKKETLIQENVVLPQIHTVTGTKNFMKNLFLLST |
| RQNVEGSYDGAYAPVLQDFRSLNDSTNRTKKHTAHFSKKGEEENLEGLGN |
| QTKQIVEKYACTTRISPNTSQQNFVTQRSKRALKQFRLPLEETELEKRII |
| VDDTSTQWSKNMKHLTPSTLTQIDYNEKEKGAITQSPLSDCLTRSHSIPQ |
| ANRSPLPIAKVSSFPSIRPTYLTRVLFQDNSSHLPAASYRKKDSGVQESS |
| HFLQGAKKNNLSLAILTLEMTGDQREVGSLGTSATNSVTYKKVENTVLPK |
| PDLPKTSGKVELLPKVHIYQKDLFPTETSNGSPGHLDLVEGSLLQGTEGA |
| IKWNEANRPGKVPFLRVATESSAKTPSKLLDPLAWDNHYGTQIPKEEWKS |
| QEKSPEKTAFKKKDTILSLNACESNHAIAAINEGQNKPEIEVTWAKQGRT |
| ERLCSQNPPVLKRHQREITRTTLQSDQEEIDYDDTISVEMKKEDFDIYDE |
| DENQSPRSFQKKTRHYFIAAVERLWDYGMSSSPHVLRNRAQSGSVPQFKK |
| VVFQEFTDGSFTQPLYRGELNEHLGLLGPYIRAEVEDNIMVTFRNQASRP |
| YSFYSSLISYEEDQRQGAEPRKNFVKPNETKTYFWKVQHHMAPTKDEFDC |
| KAWAYFSDVDLEKDVHSGLIGPLLVCHTNTLNPAHGRQVTVQEFALFFTI |
| FDETKSWYFTENMERNCRAPSNIQMEDPTFKENYRFHAINGYIMDTLPGL |

TABLE 1-continued

Factor VIII-Tregitope (Tregitope bold)

VMAQDQRIRWYLLSMGSNENIHSIHFSGHVFTVRKKEEYKMALYNLYPGV
FETVEMLPSKAGIWRVECLIGEHLHAGMSTLFLVYSNKCQTPLGMASGHI
RDFQITASGQYGQWAPKLARLHYSGSINAWSTKEPFSWIKVDLLAPMIIH
GIKTQGARQKFSSLYISQFIIMYSLDGKKWQTYRGNSTGTLMVFFGNVDS
SGIKHNIFNPPIIARYIRLHPTHYSIRSTLRMELMGCDLNSCSMPLGMES
KAISDAQITASSYFTNMFATWSPSKARLHLQGRSNAWRPQVNNPKEWLQV
DFQKTMKVTGVTTQGVKSLLTSMYVKEFLISSSQDGHQWTLFFQNGKVKV
FQGNQDSFTPVVNSLDPPLLTRYLRIHPQSWVHQIALRMEVLGCEAQDLY
EEQYNSTYRVVSVLTVLHQDW

Example 7

Generation of a FVIII-Multi-Tregitope Construct

Multiple Tregitopes can be present in highly immunogenic proteins to promote adaptive tolerance. Chimeric constructs comprised of the coding sequence of clotting Factor VIII and multiple Tregitope(s) are produced (Sambrook et al., *Molecular Cloning: A Laboratory Manual*, 2 ed., Cold Spring Harbor Laboratory Press, (1989)). Briefly, the Factor VIII coding region fused at the carboxyterminal to a Tregitope is generated by annealing overlapping oligos and sub-cloned into an expression plasmid. The plasmids are transfected into DG44 CHO cells and stable transfectants selected. The chimeric protein is purified over a immuno-affinity column and evaluated for tolergenicity. Table 2 illustrates one embodiment of such a chimeric protein.

TABLE 2

Factor VIII-multi Tregitope (Tregitope(s) bold)

SEQ ID NO: 2
MQIELSTCFFLCLLRFCFSATRRYYLGAVELSWDYMQSDLGELPVDARFP
PRVPKSFPFNTSVVYKKTLFVEFTDHLFNIAKPRPPWMGLLGPTIQAEVY
DTVVITLKNMASHPVSLHAVGVSYWKASEGAEYDDQTSQREKEDDKVFPG
GSHTYVWQVLKENGPMASDPLCLTYSYLSHVDLVKDLNSGLIGALLVCRE
GSLAKEKTQTLHKFILLLFAVFDEGKSWHSETKNSLMQDRDAASARAWPKM
HTVNGYVNRSLPGLIGCHRKSVYWHVIGMGTTPEVHSIFLEGHTFLVRNH
RQASLEISPITFLTAQTLLMDLGQFLLFCHISSHQHDGMEAYVKVDSCPE
EPQLRMKNNEEAEDYDDDLTDSEMDVVRFDDDNSPSFIQIRSVAKKHPKT
WVHYIAAEEEDWDYAPLVLPDDRSYKSQYLNNGPQRIGRKYKKVRFMAYT
DETFKTREAIQHESGILGPLLYGEVGDTLLIIFKNQASRPYNTYPHGITD
VRPLYSRRLPKGVKHLKDEPILPGEIFKYKWTVTVEDGPTKSDPRCLTRY
YSSFVNMERDLASGLIGPLLICYKESVDQRGNQIMSDKRNVILFSVFDEN
RSWYLTENIQRFLPNPAGVQLEDPEFQASNIMHSINGYVFDSLQLSVCLH
EVAYWYILSIGAQTDFLSVFFSGYTFKHKMVYEDTLTLFPFSGETVFMSM
ENPGLWILGCHNSDFRNRGMTALLKVSSCDKNTGDYYEDSYEDISAYLLS
KNNAIEPRSFSQNSRHPSTRQKQFNATTIPENDIEKTDPWFAHRTPMPKI
QNVSSSDLLMLLRQSPTPHGLSLSDLQEAKYETFSDDPSPGAIDSNNSLS
EMTHFRPQLHHSGDMVFTPESGLQLRLNEKLGTTAATELKKLDFKVSSTS
NNLISTIPSDNLAAGTDNTSSLGPPSMPVHYDSQLDTTLFGKKSSPLTES
GGPLSLSEENNDSKLLESGLMNSQESSWGKNVSSTESGRLFKGKRAHGPA
LLTKDNALFKVSISLLKTNKTSNNSATNRKTHIDGPSLLIENSPSVWQNI
LESDTEFKKVTPLIHDRMLMDKNATALRLNHMSNKTTSSKNMEMVQQKKE
GPIPPDAQNPDMSFFKMLFLPESARWIQRTHGKNSLNSGQGPSPKQLVSL
GPEKSVEGQNFLSEKNKVVVGKGEFTKDVGLKEMVFPSSRNLFLTNLDNL
HENNTHNQEKKIQEEIEKKETLIQENVVLPQIHTVTGTKNFMKNLFLLST
RQNVEGSYDGAYAPVLQDFRSLNDSTNRTKKHTAHFSKKGEEENLEGLGN
QTKQIVEKYACTTRISPNTSQQNFVTQRSKRALKQFRLPLEETELEKRII
VDDTSTQWSKNMKHLTPSTLTQIDYNEKEKGAITQSPLSDCLTRSHSIPQ
ANRSPLPIAKVSSFPSIRPTYLTRVLFQDNSSHLPAASYRKKDSGVQESS
HFLQGAKKNNLSLAILTLEMTGDQREVGSLGTSATNSVTYKKVENTVLPK
PDLPKTSGKVELLPKVHIYQKDLFPTETSNGSPGHLDLVEGSLLQGTEGA
IKWNEANRPGKVPFLRVATESSAKTPSKLLDPLAWDNHYGTQIPKEEWKS
QEKSPEKTAFKKKDTILSLNACESNHAIAAINEGQNKPEIEVTWAKQGRT
ERLCSQNPPVLKRHQREITRTTLQSDQEEIDYDDTISVEMKKEDFDIYDE
DENQSPRSFQKKTRHYFIAAVERLWDYGMSSSPHVLRNRAQSGSVPQFKK
VVFQEFTDGSFTQPLYRGELNEHLGLLGPYIRAEVEDNIMVTFRNQASRP
YSFYSSLISYEEDQRQGAEPRKNFVKPNETKTYFWKVQHHMAPTKDEFDC
KAWAYFSDVDLEKDVHSGLIGPLLVCHTNTLNPAHGRQVTVQEFALFFTI

TABLE 2-continued

Factor VIII-multi Tregitope (Tregitope(s) bold)

FDETKSWYFTENMERNCRAPSNIQMEDPTFKENYRFHAINGYIMDTLPGL
VMAQDQRIRWYLLSMGSNENIHSIHFSGHVFTVRKKEEYKMALYNLYPGV
FETVEMLPSKAGIWRVECLIGEHLHAGMSTLFLVYSNKCQTPLGMASGHI
RDFQITASGQYGQWAPKLARLHYSGSINAWSTKEPFSWIKVDLLAPMIIH
GIKTQGARQKFSSLYISQFIIMYSLDGKKWQTYRGNSTGTLMVFFGNVDS
SGIKHNIFNPPIIARYIRLHPTHYSIRSTLRMELMGCDLNSCSMPLGMES
KAISDAQITASSYFTNMFATWSPSKARLHLQGRSNAWRPQVNNPKEWLQV
DFQKTMKVTGVTTQGVKSLLTSMYVKEFLISSSQDGHQWTLFFQNGKVKV
FQGNQDSFTPVVNSLDPPLLTRYLRIHPQSWVHQIALRMEVLGCEAQDLY
EEQYNSTYRVVSVLTVLHQDWEEQYNSTYRVVSVLTVLHQDWEEQYNSTY
RVVSVLTVLHQDWEEQYNSTYRVVSVLTVLHQDW

Example 8

Generation of an Enhanced Vaccine Delivery Vehicle

Fc binding to Fc receptors enhance uptake in antigen presenting cells presentation to T and B lymphocytes. Tregitope-289, located in the Fc domain of IgG molecules acts to deliver suppressive signals. The modification of Fc so that Tregitope-289 no longer binds to MHC molecules and regulatory T cells allows for efficient targeting of vaccine candidates while avoiding suppressive effects. Modifications to decrease binding of Tregitopes to MHC molecules are useful. FIG. 22 illustrates such a modification. Chimeric constructs comprised of various proteins or epitope pseudoproteins of interest and a Tregitope modified mIgG Fc are designed (Sambrook et al., Molecular Cloning: A Laboratory Manual, 2 ed., Cold Spring Harbor Laboratory Press, (1989)). Briefly, the protein or epitope pseudo-protein of interest is generated by annealing overlapping oligos and sub-cloned into a Tregitope modified Fc fusion expression plasmid. The plasmids are transfected into DG44 CHO cells and stable transfectants selected. The chimeric protein homodimers are purified over a protein A column and evaluated for immunogenicity. FIG. 22 illustrates one embodiment of a chimeric protein where the pseudo-protein of interest is a string of immunogenic T cell epitopes derived from the Epstein Barr Virus (EBV) fused to a modified Fc protein in which the Tregitope has been modified to no longer bind MHC class II molecules and can not stimulate natural regulatory T cells. EBV-Tregitope modified Fc SEQUENCE (Kb SIGNAL SEQUENCE) in FIG. 22 is designated as underlined text. The Tregitope is designated as bold text. The Tregitope modified amino acids are designated as shaded text. The human Fc region is designated as italicized text.

REFERENCES

Ahlers, J. et al., *J. Clin. Invest.*, 108:1677-1685, 2001.
Bischof, F. et al., *Proc. Natl. Acad. Sci. USA*, 98:12168-73, 2001. Epub. 2001 Oct. 2.
Cobbold, S. et al., *Immunol Rev.*, 213:239-55, 2006.
D'Ambrosio, D. et al., J. Immunol., 161:5111-5, 1998.
De Groot, A. and Berzofsky, J., *Methods*, 34:425-428, 2004.
De Groot, A. et al., *Immunol. Cell Biol.*, 80:255-269, 2002.
Durinovic-Bello, I. et al., *Proc. Natl. Acad. Sci. USA*, 103:11683-11688, 2006.
El-Amine, M. et al., *J. Immunol.*, 165:5631-5636, 2000.
El-Amine, M. et al., *Int. Immunol.*, 14:761-766, 2002.
Feng, I. et al., *J Biomed Sci.*, 14:43-57, 2006.
Hjelm, F. et al., *Scand. J. Immunol.*, 64:177-184, 2006.

Hochweller, K. et al., *Curr. Mol. Med.*, 6:631-43, 2006.
Huang, X. et al., *J. Immunol.*, 175:4283-4291, 2005.
Jordan, S. et al., *Am. J. Transplant.*, 6:459-66, 2006.
Karlsson M. et al., *Proc. Natl. Acad. Sci. USA*, 96:2244-2249, 1999.
Klee, L. and Zand, R., *Neuroinformatics*, 2:59-70, 2004.
Monneaux, F. et al., *J. Immunol.*, 175:5839-5847, 2005.
Mudd, P. et al., *Scand. J. Immunol.*, 64:211-8, 2006.
Nagata, K. et al., *J. Immunol.*, 162:1278-86, 1999.
Nguyen, V. et al., Biol. Blood Marrow Transplant, 12:995-1009, 2006.
Phillips, W. et al., *Int. Rev. Immunol.*, 24:501-17, 2005.
Reijonen, H. and Kwok W., *Methods*, 29:282-288, 2003.
Reitan, S. and Hannestad, K., *Proc. Natl. Acad. Sci. USA*, 99:7588-7593, 2002.
Shevach, E. et al., *Immunol. Rev.*, 212:60-73, 2006.
Shioji, K. et al., *Circ. Res.*, 89:540-546, 2001.
Southwood, S. et al., *J. Immunol.*, 160:3363-3373, 1998.
St. Clair, E. et al., *Annu. Rev. Med.*, 58:329-346, 2006.
Stock, P. et al., *Curr. Opin. Allergy Clin. Immunol.*, 6:12-16, 2006.
Sumida, T. et al., *Arthritis Rheum.*, 40:2271-2273, 1997.
Tang, Q. and Bluestone, *J. Immunol. Rev.*, 212:217-37, 2006.
Wing, K. and Sakaguchi, S., *Curr. Opin. Allergy Clin. Immunol.*, 6:482-488, 2006.
Wohlleben, G. and Erb, K., *Curr. Pharm. Des.*, 12:3281-92, 2006.
Zambidis, E. and Scott, D., *Proc. Natl. Acad. Sci. USA*, 93:5019-5024, 1996.

EQUIVALENTS

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A method of inducing regulatory T-cells to suppress immune response in a subject comprising administrating to the subject a therapeutically effective amount of a T-cell epitope composition, wherein the T-cell epitope composition comprises one or more isolated T-cell epitope polypeptides, wherein at least one isolated T-cell epitope polypeptide consists of the amino acid sequence of SEQ ID NO: 7.

2. The method of claim 1, wherein the T-cell epitope composition further comprises at least one isolated T-cell epitope polypeptide consisting of an amino acid sequence selected from the group consisting of SEQ ID NOS: 6 and 8-58.

3. The method of claim 1, wherein the T-cell epitope composition further comprises at least one isolated T-cell epitope polypeptide consisting of an amino acid sequence selected from the group consisting of SEQ ID NOS: 6, 10, 12 14, 15, 23, 24, 25 or 31.

4. The method of claim 1, wherein the T-cell epitope composition further comprises an effective amount of one or more antigens and/or allergens.

5. The method of claim 1, wherein the immune suppressive effect is mediated by natural regulatory Tcells.

6. The method of claim 1, wherein the immune suppressive effect is mediated by adaptive regulatory T-cells.

7. The method of claim 1, wherein the T-cell epitope composition suppresses an effector T-cell response.

8. The method of claim 7, wherein the T-cell epitope composition suppresses a cytokine secretion of effector T-cells.

9. The method of claim 1, wherein the T-cell epitope composition suppresses a helper T-cell response.

10. The method of claim 1, wherein the T-cell epitope composition suppresses a B-cell response.

* * * * *